US012779046B2

(12) United States Patent
Matsuno et al.

(10) Patent No.: US 12,779,046 B2
(45) Date of Patent: Nov. 3, 2026

(54) HETEROBIFUNCTIONAL MONODISPERSED POLYETHYLENE GLYCOL HAVING PEPTIDE LINKER

(71) Applicant: NOF CORPORATION, Tokyo (JP)

(72) Inventors: Yuki Matsuno, Kawasaki (JP); Hiroki Yoshioka, Kawasaki (JP); Akira Suzuki, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 1262 days.

(21) Appl. No.: 17/762,719

(22) PCT Filed: Sep. 25, 2020

(86) PCT No.: PCT/JP2020/036195
§ 371 (c)(1),
(2) Date: Mar. 22, 2022

(87) PCT Pub. No.: WO2021/060439
PCT Pub. Date: Apr. 1, 2021

(65) Prior Publication Data

US 2022/0362397 A1 Nov. 17, 2022

(30) Foreign Application Priority Data

Sep. 26, 2019 (JP) ................................ 2019-176066

(51) Int. Cl.
*A61K 47/68* (2017.01)
*A61K 47/60* (2017.01)
*C07K 5/06* (2006.01)

(52) U.S. Cl.
CPC .......... *A61K 47/6889* (2017.08); *A61K 47/60* (2017.08); *C07K 5/06* (2013.01)

(58) Field of Classification Search
CPC ................................................ A61K 47/6889
See application file for complete search history.

(56) References Cited

U.S. PATENT DOCUMENTS

2007/0123465 A1 5/2007 Adermann et al.
2012/0077988 A1 3/2012 Yamamoto et al.
(Continued)

FOREIGN PATENT DOCUMENTS

CN 1221447 A * 4/1997
CN 1706865 A 12/2005
(Continued)

OTHER PUBLICATIONS

Machine Translation of CN1221447A (Year: 2026).*
(Continued)

*Primary Examiner* — Paul W Dickinson
(74) *Attorney, Agent, or Firm* — Leydig, Voit & Mayer, Ltd.

(57) ABSTRACT

A heterobifunctional monodisperse polyethylene glycol with two adjacent monodisperse polyethylene glycol side chains, in which a peptide linker is degraded by intracellular enzymes to release a drug slowly and effectively mask the hydrophobicity of the drug, and an antibody-drug conjugate in which the antibody and the drug are bound using same is provided. A heterobifunctional monodisperse polyethylene glycol represented by the formula (1):

(1)

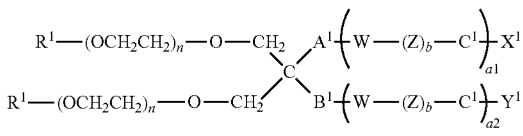

wherein each symbol in the formula (1) is as defined in the DESCRIPTION.

6 Claims, 12 Drawing Sheets

(56) References Cited

U.S. PATENT DOCUMENTS

| | | | | |
|---|---|---|---|---|
| 2016/0082123 | A1 * | 3/2016 | Rau | A61K 47/60 514/11.2 |
| 2016/0193355 | A1 | 7/2016 | Qin et al. | |
| 2016/0271116 | A1 | 9/2016 | Jia et al. | |
| 2017/0313656 | A1 | 11/2017 | Davis et al. | |
| 2020/0000933 | A1 | 1/2020 | Tsubusaki et al. | |
| 2021/0047465 | A1 | 2/2021 | Yoshimura et al. | |

FOREIGN PATENT DOCUMENTS

| | | | |
|---|---|---|---|
| CN | 101168594 | A | 4/2008 |
| CN | 104109235 | A | 10/2014 |
| CN | 108530617 | A | 9/2018 |
| EP | 1877101 | B1 | 11/2016 |
| WO | WO 2005/108463 | A2 | 11/2005 |
| WO | WO 2015/057699 | A2 | 4/2015 |
| WO | WO 2016/063006 | A1 | 4/2016 |
| WO | WO 2018/181059 | A1 | 10/2018 |
| WO | WO 2019/176875 | A1 | 9/2019 |

OTHER PUBLICATIONS

Lyon et al. "Reducing Hydrophobicity of Homogeneous Antibody-Drug Conjugates Improves Pharmacokinetics and Therapeutic Index," *Nature Biotechnology*, 33(7): 733-735 (2015).

Japan Patent Office, International Search Report in International Patent Application No. PCT/JP2020/036195 (Dec. 15, 2020).

* cited by examiner

HETEROBIFUNCTIONAL MONODISPERSED POLYETHYLENE GLYCOL HAVING PEPTIDE LINKER

TECHNICAL FIELD

The present invention relates to a heterobifunctional monodisperse polyethylene glycol having a peptide linker and two different chemically reactive functional groups. More particularly, it relates to a heterobifunctional monodisperse polyethylene glycol having a peptide linker and two different chemically reactive functional groups, which is used to modify biofunctional molecules such as physiologically active proteins, peptides, antibodies, nucleic acids and small molecule drugs, drug carriers in drug delivery systems, or diagnostic materials and medical devices, and is particularly useful for modifying antibody drugs.

BACKGROUND ART

Antibody-Drug Conjugate (ADC) is an antibody drug that aims to bind a drug to an antibody and actively transport the drug to the diseased site by utilizing the antigen specificity of the antibody, and is one of the technologies that have grown most rapidly in recent years in the field of cancer treatment. ADC consists of an antibody, a drug, and a linker that binds the antibody to the drug.

Many of the drugs used for ADC are hydrophobic. When a plurality of such hydrophobic drugs are bound to an antibody to prepare an ADC, the generation of aggregates due to the hydrophobicity of the drug and a decrease in the stability of the antibody in blood pose problems. Therefore, the number of drugs that can be loaded per antibody is limited, and as a result, the efficacy of the ADC may not be sufficiently achieved.

One of the solutions considered for this problem is the use of hydrophilic linkers. Polyethylene glycol, hydrophilic peptides, sugar chains, and the like are used as hydrophilic linkers. In particular, polyethylene glycol has low antigenicity and high biocompatibility, and therefore, it is currently used in multiple ADCs in clinical trials and preclinical trials.

In the field of ADC, compounds containing 90% or more of components having a specific ethylene glycol chain length are used for the purpose of ensuring the uniformity of ADC and facilitating purification, analysis, and application for drug approval. Such compounds are referred to as monodisperse polyethylene glycol.

When monodisperse polyethylene glycol is used as a linker for ADC, heterobifunctional monodisperse polyethylene glycol having two different chemically reactive functional groups is utilized because it is necessary to distinguish and bind the antibody and the drug. Generally, ADC is prepared using compounds having different chemically reactive functional groups at both ends of a monodisperse polyethylene glycol chain.

On the contrary, in recent years, ADCs have been reported in which monodisperse polyethylene glycol is introduced as a side chain into a branched linker that connects an antibody and a drug, instead of using monodisperse polyethylene glycol as a linker main chain that connects an antibody and a drug.

In Non Patent Literature 1, pharmacokinetics and therapeutic effects were compared between ADC using monodisperse polyethylene glycol as the linker main chain that connects an antibody and a drug, and ADC using monodisperse polyethylene glycol as a side chain of a branched linker that connects an antibody and a drug, and it has been reported that the latter has a higher masking effect on the hydrophobicity of the drug and exhibits superior pharmacokinetics and therapeutic effects.

In addition, Patent Literature 1 and Patent Literature 2 disclose various types of ADCs having monodisperse polyethylene glycol as a side chain of a branched linker and intermediates for preparing them.

Also, Patent Literature 3 discloses heterobifunctional monodisperse polyethylene glycol having two monodisperse polyethylene glycols bonded to a quaternary carbon atom in a four-branched skeleton and having two types of functional groups at two ends of the branch, and ADCs using same.

CITATION LIST

Patent Literatures

[PTL 1]
WO 2015/057699
[PTL 2]
WO 2016/063006
[PTL 3]
WO 2018/181059

Non Patent Literature

[NPL 1]
Nature Biotechnology, 2015, 33, 733-735

DISCLOSURE OF THE INVENTION

Technical Problem

Patent Literature 1 and Patent Literature 2 also disclose ADC with two or more monodisperse polyethylene glycols in the side chain of a branched linker. However, the bonding positions of the respective monodisperse polyethylene glycol side chains are separated, and the masking effect of the "umbrella-like" structure (Biomaterials 2001, 22(5), 405-417), which is the characteristic of branched polyethylene glycol having multiple polyethylene glycol chains, is small on hydrophobic drugs. Thus, the advantage of having a plurality of monodisperse polyethylene glycol side chains cannot be utilized effectively.

In addition, Non Patent Literature 1 and Patent Literature 3 disclose branched monodisperse polyethylene glycol having monodisperse polyethylene glycol in the side chain of a branched linker, and ADCs using the same for binding an antibody and a drug. However, after the ADC is taken up into the cell, the antibody is degraded by intracellular enzymes, but the monodisperse polyethylene glycol binds to the drug to possibly reduce the activity of the drug, which is not preferable.

The present invention relates to an antibody-drug conjugate in which an antibody and a drug are linked with a peptide linker and a linker having a monodisperse polyethylene glycol side chain. That is, the problem of the present invention is to provide a heterobifunctional monodisperse polyethylene glycol with two adjacent monodisperse polyethylene glycol side chains, in which a peptide linker is degraded by intracellular enzymes to release a drug slowly and effectively mask the hydrophobicity of the drug, and an antibody-drug conjugate in which the antibody and the drug are bound using same.

Solution to Problem

The present inventors have conducted intensive studies in an attempt to solve the above-mentioned problems and developed a heterobifunctional monodisperse polyethylene glycol which is a heterobifunctional compound having a peptide linker to be degraded by intracellular enzymes and two closely-bonded monodisperse polyethylene glycol side chains, and an antibody-drug conjugate in which an antibody and a drug are bound using same.

Furthermore, the heterobifunctional monodisperse polyethylene glycol of the present invention is characterized in that it is not easily decomposed into single-chain monodisperse polyethylene glycol in the chemical conversion process of the structure of the heterobifunctional monodisperse polyethylene glycol, because two monodisperse polyethylene glycol side chains are bonded to the quaternary carbon atom of the branched portion by a stable ether bond.

In addition, the heterobifunctional monodisperse polyethylene glycol of the present invention is characterized in that the peptide linker it has that is degraded by intracellular enzymes allows effective sustained release of a drug in the cell and the activity of the drug in the cell is not affected.

Accordingly, the present invention provides the following.

[1] A heterobifunctional monodisperse polyethylene glycol represented by the formula (1):

(1)

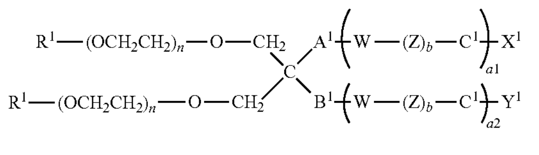

(in the formula (1), $X^1$ and $Y^1$ are each an atomic group containing at least a functional group that reacts with a functional group present in a biofunctional molecule to form a covalent bond, and the aforementioned functional group contained in the atomic group $X^1$ and the aforementioned functional group contained in the atomic group $Y^1$ are different from each other;

$R^1$ is a hydrocarbon group having 1-7 carbon atoms or a hydrogen atom;

n is an integer of 3-72;

$A^1$ is $-L^1-(CH_2)_{m1}-L^2-$, $-L^1-(CH_2)_{m1}-L^2-(CH_2)_{m2}-$, an amide bond, a urethane bond, a secondary amino group, or a single bond, and m1 and m2 are each independently an integer of 1-5;

$B^1$ is $-CH_2-L^3-$, $-CH_2-L^3-(CH_2)_{m3}-L^4-$ or $-CH_2-L^3-(CH_2)_{m3}-L^4-(CH_2)_{m4}-$, and m3 and m4 are each independently an integer of 1-5;

W is an oligopeptide with 2 to 4 residues;

Z is a spacer with a bifunctional para-aminobenzyl alcohol group that binds to the C-terminal of peptide;

when a1=1, a2=0, and when a1=0, a2=1;

b is 0 or 1;

$C^1$ is $-L^5-(CH_2)_{m5}-$, $-L^5-(CH_2)_{m5}-L^6-(CH_2)_{m6}-$, an amide bond, or a single bond, and m5 and m6 are each independently an integer of 1-5; and $L^1$-$L^6$ are each independently an ether bond, a urethane bond, an amide bond, a secondary amino group, a carbonyl group, or a single bond.)

[2] The heterobifunctional monodisperse polyethylene glycol of [1], wherein W is an oligopeptide with 2 to 4 residues and containing at least one of hydrophobic neutral amino acids of phenylalanine, leucine, valine, and isoleucine, and the other amino acids consist of neutral amino acids other than cysteine.

[3] The heterobifunctional monodisperse polyethylene glycol of [1], wherein W is an oligopeptide with 2 to 4 residues and containing at least one of hydrophobic neutral amino acids of phenylalanine, leucine, valine, and isoleucine, and the other amino acids contain at least one of alanine, glycine, citrulline, proline, serine, and asparagine.

[4] The heterobifunctional monodisperse polyethylene glycol of [1], wherein W is an oligopeptide whose C-terminal amino acid is glycine.

[5] The heterobifunctional monodisperse polyethylene glycol of [1], wherein W is dipeptide.

[6] The heterobifunctional monodisperse polyethylene glycol of any one of [1]-[5], wherein $X^1$ and $Y^1$ in the formula (1) are each independently selected from the group consisting of the formula (a), the formula (b1), the formula (b2), the formula (c), the formula (d1), the formula (d2), the formula (e), the formula (f), the formula (g), the formula (h), the formula (i), the formula (j), the formula (k), the formula (l), the formula (m), the formula (n), and the formula (o):

(a)

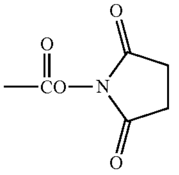

(b1)

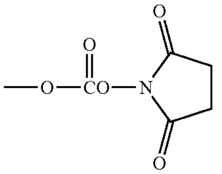

(b2)

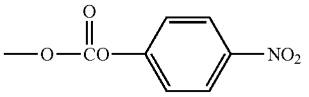

(c)

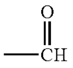

(d1)

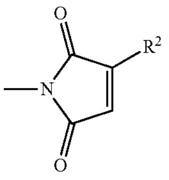

(d2)

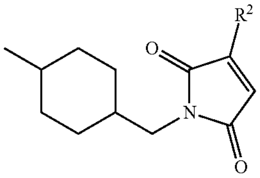

(e)

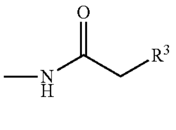

-continued (f)

$—COOH$ (g)

$—SH$ (h)

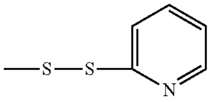

(i)

$—NH_2$ (j)

$—O—NH_2$ (k)

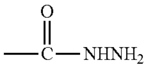

(l)

$—C≡C—R^4$ (m)

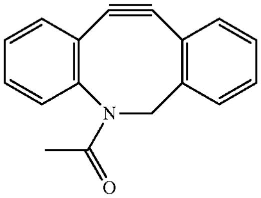

(n)

$—N_3$ (o)

$—OH$ (in the formulas (d1) and (d2), $R^2$ is a hydrogen atom or a hydrocarbon group having 1-5 carbon atoms; in the formula (e), $R^3$ is a halogen atom selected from a chlorine atom, a bromine atom, and an iodine atom; and in the formula (l), $R^4$ is a hydrogen atom or a hydrocarbon group having 1-5 carbon atoms.)

[7] An antibody-drug conjugate represented by the formula (2), comprising a heterobifunctional monodisperse polyethylene glycol:

(2)

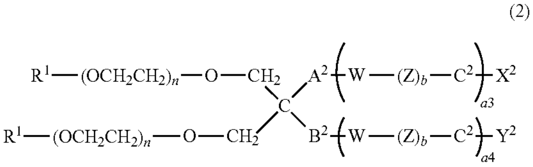

(in the formula (2), one of $X^2$ and $Y^2$ is an antibody and the other is a drug;

$R^1$ is a hydrocarbon group having 1-7 carbon atoms or a hydrogen atom;

n is an integer of 3-72;

$A^2$ is $-L^1-(CH_2)_{m1}-L^7-$, $-L^1-(CH_2)_{m1}-L^8-$, $-L^1-(CH_2)_{m1}-L^2-(CH_2)_{m2}-L^8-$ or $-L^8-$, and m1 and m2 are each independently an integer of 1-5;

$B^2$ is $—CH_2-L^9-$, $—CH_2-L^9-(CH_2)_{m3}-L^{10}-$, $—CH_2-L^9-(CH_2)_{m3}-L^{10}-(CH_2)_{m4}-L^1-$, $—CH_2-L^{12}-$, $—CH_2-L^9-(CH_2)_{m3}-L^{12}-$ or $—CH_2-L^9-(CH_2)_{m3}-L^{10}-(CH_2)_{m4}-L^{12}-$, and m3 and m4 are each independently an integer of 1-5;

$L^1$ and $L^2$ are each independently an ether bond, a urethane bond, an amide bond, a secondary amino group or a single bond;

$L^7$, $L^9$, $L^{10}$ and $L^{11}$ are each independently an ether bond, a urethane bond, an amide bond, a secondary amino group or a carbonyl group;

$L^8$ and $L^2$ are each an amide bond, a urethane bond, a bond of maleimide and thiol, a thioether bond, a disulfide bond, a carbonate bond, an ester bond, an ether bond, a 1H-1,2,3-triazole-1,4-diyl structure, a secondary amino group, a hydrazide group, an oxyamide group, a hydrocarbon group containing these, or a single bond;

W is an oligopeptide with 2 to 4 residues;

Z is a spacer with a bifunctional para-aminobenzyl alcohol group that binds to the C-terminal of peptide;

a3 and a4: when $X^2$ is a drug, a3=1 and a4=0, and when $Y^2$ is a drug, a3=0 and a4=1;

b is 0 or 1; and $C^2$ is an amide bond, a urethane bond, a bond of maleimide and thiol, a thioether bond, a disulfide bond, a carbonate bond, an ester bond, an ether bond, a 1H-1,2,3-triazole-1,4-diyl structure, a secondary amino group, a hydrazide group, an oxyamide group, or a hydrocarbon group containing these.)

[8] The antibody-drug conjugate of [7], wherein W is an oligopeptide with 2 to 4 residues and containing at least one of hydrophobic neutral amino acids of phenylalanine, leucine, valine, and isoleucine, and the other amino acids consist of neutral amino acids other than cysteine.

[9] The antibody-drug conjugate of [7], wherein W is an oligopeptide with 2 to 4 residues and containing at least one of hydrophobic neutral amino acids of phenylalanine, leucine, valine, and isoleucine, and the other amino acids contain at least one of alanine, glycine, citrulline, proline, serine, and asparagine.

[10] The antibody-drug conjugate of [7], wherein W is an oligopeptide whose C-terminal amino acid is glycine.

[11] The antibody-drug conjugate of [7], wherein W is dipeptide.

Advantageous Effects of Invention

The heterobifunctional monodisperse polyethylene glycol of the present invention has two monodisperse polyethylene glycol side chains bonded to the quaternary carbon atom of the branched portion by a stable ether bond, due to which it is not easily decomposed into single-chain monodisperse polyethylene glycol in the chemical conversion process. Accordingly, a highly homogeneous antibody-drug conjugate can be obtained by binding an antibody to a drug by using the heterobifunctional monodisperse polyethylene glycol.

Furthermore, the heterobifunctional monodisperse polyethylene glycol has two monodisperse polyethylene glycol side chains which are bonded near. When an antibody-drug conjugate is prepared, therefore, a high hydrophobic drug-masking effect is obtained, and the generation of aggregation due to the hydrophobicity of the drug and a decrease in the blood stability of the antibody can be suppressed.

Furthermore, since the heterobifunctional monodisperse polyethylene glycol contains a peptide linker that is degraded by intracellular enzymes, the linker part is cleaved from the drug in the cell, and the drug can be effectively released in a sustained manner in the cell.

DESCRIPTION OF EMBODIMENTS

Figure 1:
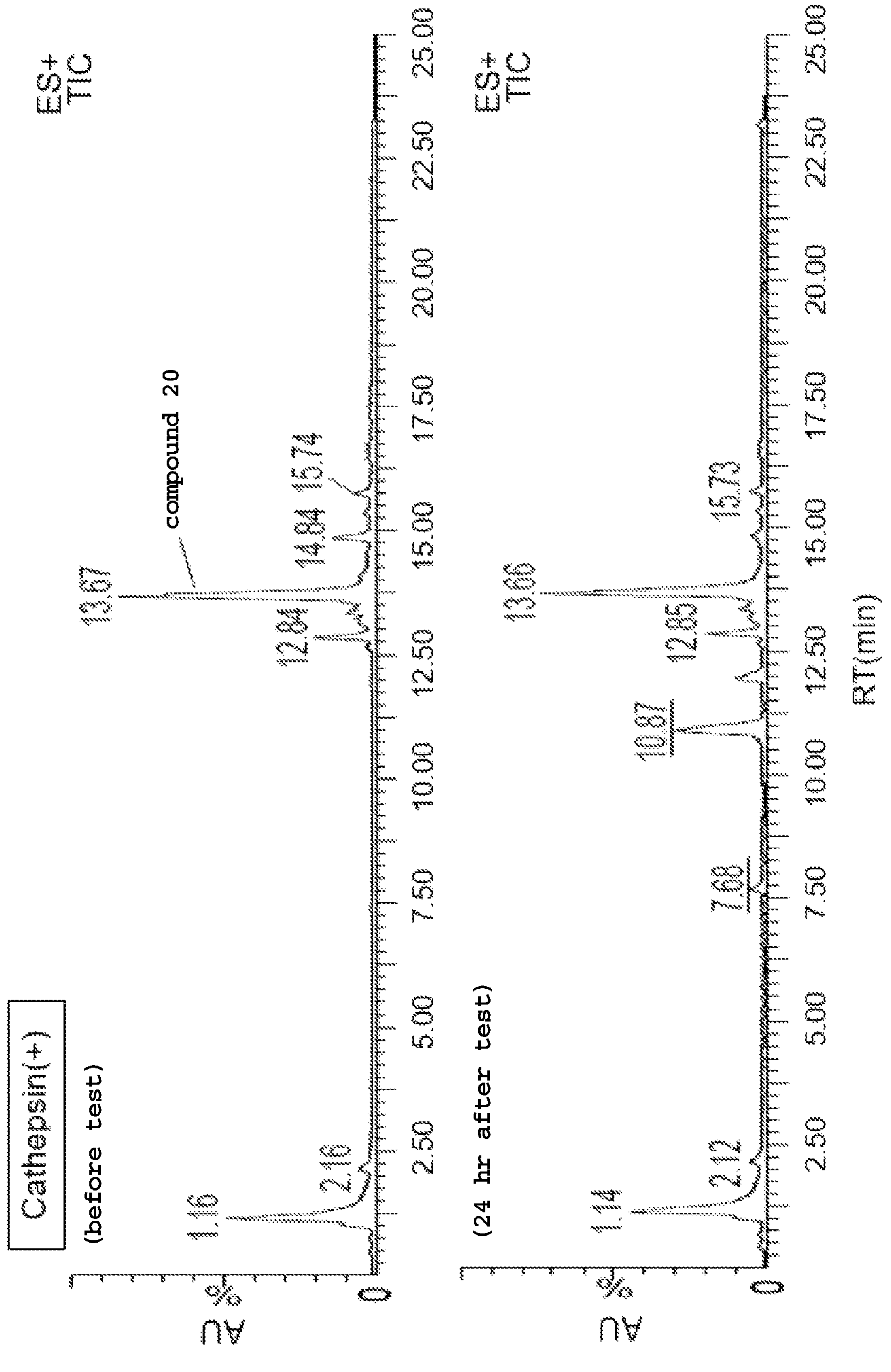
FIG. 1 shows the HPLC measurement results of the compound of the formula (20) of Example 10, before and after the degradability test in Example 37.

The present invention is explained in detail below.

In the present specification, the "heterobifunctional" means having two different chemically reactive functional groups, the "monodisperse polyethylene glycol" means a compound containing not less than 90% of components having a specific ethylene glycol chain length, and the "linker" is a chemical site that covalently binds an antibody to a drug or contains a carbon chain.

The heterobifunctional monodisperse polyethylene glycol of the present invention is represented by the formula (1):

(1)

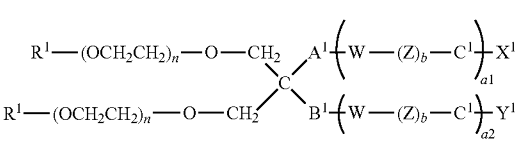

$R^1$ in the formula (1) of the present invention is a hydrocarbon group having 1-7 carbon atoms or a hydrogen atom, and a specific hydrocarbon group includes, for example, a methyl group, an ethyl group, a propyl group, an isopropyl group, a t-butyl group, a phenyl group and a benzyl group. A preferred embodiment of $R^1$ is a methyl group or a hydrogen atom, and a methyl group is further preferred.

In the formula (1) of the present invention, n is an integer of 3-72, preferably 4-48, further preferably 6-36, particularly preferably 8-24, which shows a repeat unit number of the monodisperse polyethylene glycol.

In the present specification, the atomic groups $X^1$ and $Y^1$ in the formula (1) are different from each other, and are not particularly limited as long as each is an atomic group containing at least a functional group that reacts with a functional group present in biofunctional molecules (physiologically active protein, peptide, antibody, nucleic acid and low-molecular drug and the like) to be modified with the heterobifunctional monodisperse polyethylene glycol, and forms a covalent bond. Examples of the aforementioned functional group include the functional groups described in "Hermanson, G. T. Bioconjugate Techniques, 2nd ed.; Academic Press: San Diego, CA, 2008", "Harris, J. M. Poly (Ethylene Glycol) Chemistry; Plenum Press: New York, 1992", and "PEGylated Protein Drugs: Basic Science and Clinical Applications; Veronese, F. M., Ed.; Birkhauser: Basel, Switzerland 2009".

Among those, the functional groups for $X^1$ or $Y^1$ are preferably each independently a functional group capable of reacting under mild reaction conditions and with high reaction efficiency with a functional group (amino group, thiol group, aldehyde group, carboxy group, etc.) existing in natural biofunctional molecules represented by proteins, and a functional group (maleimide group, ketone group, azide group, alkynyl group, etc.) that can be artificially introduced into the aforementioned biofunctional molecule. More specifically, an active ester group, an active carbonate group, an aldehyde group, an isocyanate group, an isothiocyanate group, an epoxy group, a maleimide group, a vinylsulfone group, an acrylic group, a sulfonyloxy group, a carboxy group, a thiol group, a 2-pyridyldithio group, an α-haloacetyl group, a hydroxy group, an alkynyl group, an allyl group, a vinyl group, an amino group, an oxyamino group, a hydrazide group, an azide group, and a dibenzocyclooctyne (DBCO) group are preferred. In consideration of the reaction efficiency, an active ester group, an active carbonate group, a maleimide group, an α-haloacetyl group, an alkynyl group, an azide group and a dibenzocyclooctyne (DBCO) group are preferred, and an active ester group, an active carbonate group and a maleimide group are more preferred.

Further specifically, the functional groups for $X^1$ or $Y^1$ are each independently an active ester group, an active carbonate group, an aldehyde group, an isocyanate group, an isothiocyanate group, an epoxy group, a maleimide group, a vinylsulfone group, an acrylic group, a sulfonyloxy group or a carboxy group when the functional group existing in biofunctional molecules to be modified is an amino group; an active ester group, an active carbonate group, an aldehyde group, an isocyanate group, an isothiocyanate group, an epoxy group, a maleimide group, a vinylsulfone group, an acrylic group, a sulfonyloxy group, a carboxy group, a thiol group, a 2-pyridyldithio group, an α-haloacetyl group, an alkynyl group, an allyl group or a vinyl group when the functional group existing in biofunctional molecules to be modified is a thiol group; a thiol group, a hydroxy group, an amino group, an oxyamino group or a hydrazide group when the functional group existing in biofunctional molecules to be modified is an aldehyde group or a carboxy group; a thiol group or an azide group when the functional group existing in biofunctional molecules to be modified is an alkynyl group; an alkynyl group or a dibenzocyclooctyne group when the functional group existing in biofunctional molecules to be modified is an azide group; and a thiol group, a hydroxy group or an amino group when the functional group existing in biofunctional molecules to be modified is a halogenated alkyl group, an alkylsulfonic acid ester or an arylsulfonic acid ester.

As used herein, the "active ester group" is an activated carboxy group represented by formula: —C(═O)-E wherein E is a leaving group. As the leaving group for E, a succinimidyloxy group, a phthalimidyloxy group, a 4-nitrophenoxy group, a 1-imidazolyl group, a pentafluorophenoxy group, a benzotriazol-1-yloxy group and a 7-azabenzotriazol-1-yloxy group can be mentioned, and a succinimidyloxy group and a 4-nitrophenoxy group are preferred. The "active carbonate group" is an activated carbonate group represented by formula: —O—C(═O)-E, wherein E is a leaving group which is the same as the above.

In a preferred embodiment of the present invention, $X^1$ and $Y^1$ are each independently a group represented by group (I), group (II), group (III), group (IV), group (V) or group (VI). group (I): a functional group capable of reacting with an amino group of a biofunctional molecule to form a covalent bond (a), (b1), (b2), (c), (d1), (d2), (e) and (f) below group (II): a functional group capable of reacting with a thiol group of a biofunctional molecule to form a covalent bond (a), (b1), (b2), (c), (d1), (d2), (e), (f), (g), (h) and (1) below group (III): a functional group capable of reacting with an aldehyde group or a carboxy group of a biofunctional molecule to form a covalent bond (g), (i), (j), (k) and (o) below group (IV): a functional group capable of reacting with an alkynyl group of a biofunctional molecule to form a covalent bond (g), (i), (j), (k) and (n) below group (V): a functional group capable of reacting with an azide group of a biofunctional molecule to form a covalent bond (l) and (m) below group (VI): a functional group capable of reacting with a halogenated alkyl group, alkylsulfonic acid ester or arylsulfonic acid ester of a biofunctional molecule to form a covalent bond (g), (i) and (o) below (a)

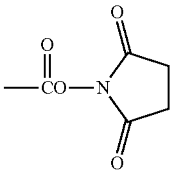

(b1)

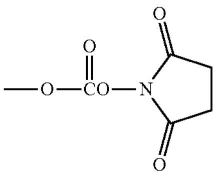

(b2)

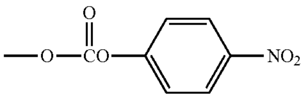

(c)

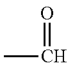

-continued (d1)

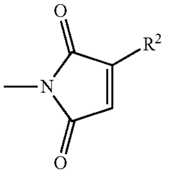

(d2)

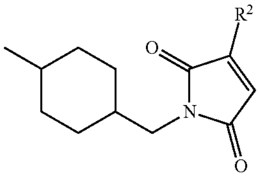

(e)

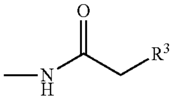

(f)

—COOH (g)

—SH (h)

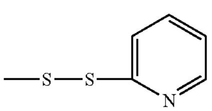

(i)

$-NH_2$ (j)

$-O-NH_2$ (k)

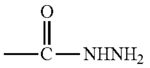

(l)

$-C\equiv C-R^4$ (m)

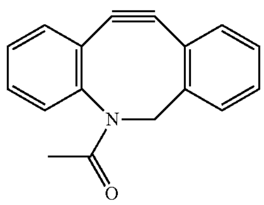

(n)

$-N_3$ (o)

—OH wherein, $R^2$ and $R^4$ are each a hydrogen atom or a hydrocarbon group having 1-5 carbon atoms, and specific hydrocarbon group includes, for example, a methyl group, an ethyl group, a propyl group, an isopropyl group, a butyl group, a t-butyl group, and a pentyl group. $R^3$ is a halogen atom selected from a chlorine atom, a bromine atom, and an iodine atom.

As preferable combinations of the functional groups for the atomic groups $X^1$ and $Y^1$ in the formula (1), the functional group for $Y^1$ is a group selected from a maleimide group, a vinylsulfone group, an α-haloacetyl group, an alkynyl group and an azide group when the functional group for $X^1$ is an active ester group or an active carbonate group; the functional group for $Y^1$ is a group selected from a maleimide group, a vinylsulfone group, an alkynyl group and an azide group when the functional group for $X^1$ is an aldehyde group; the functional group for $Y^1$ is a group selected from an active ester group, an active carbonate group, an alkynyl group, an azide group when the functional group for $X^1$ is a maleimide group, a vinylsulfone group or an $\alpha$-haloacetyl group; the functional group for $Y^1$ is a group selected from a maleimide group, a vinylsulfone group, an $\alpha$-haloacetyl group, an active ester group, an active carbonate group, an amino group, an oxyamino group and a hydroxy group when the functional group for $X^1$ is an alkynyl group or an azide group; the functional group for $Y^1$ is an alkynyl group, an azide group, a thiol group, a hydroxy group or a carboxy group when the functional group for $X^1$ is an amino group or an oxyamino group; and $Y^1$ is a group selected from an amino group, an oxyamino group, an azide group and a carboxy group when the functional group for $X^1$ is a thiol group, a 2-pyridyldithio group or a hydroxy group. More preferably, the functional group for $Y^1$ is a group selected from a maleimide group, an $\alpha$-haloacetyl group, an alkynyl group and an azide group when the functional group for $X^1$ is an active ester group or an active carbonate group; the functional group for $Y^1$ is a group selected from a maleimide group, an $\alpha$-haloacetyl group, an alkynyl group and an azide group when the functional group for $X^1$ is an aldehyde group; the functional group for $Y^1$ is a group selected from an active ester group, an active carbonate group, an alkynyl group, an azide group when the functional group for $X^1$ is a maleimide group or an $\alpha$-haloacetyl group; the functional group for $Y^1$ is a group selected from a maleimide group, an $\alpha$-haloacetyl group, an active ester group, an active carbonate group, an amino group, an oxyamino group and a hydroxy group when the functional group for $X^1$ is an alkynyl group or an azide group; the functional group for $Y^1$ is an alkynyl group, an azide group, a hydroxy group or a thiol group when the functional group for $X^1$ is an amino group or an oxyamino group; and the functional group for $Y^1$ is a group selected from an amino group, an oxyamino group and an azide group when the functional group for $X^1$ is a thiol group, a 2-pyridyldithio group or a hydroxy group.

In the formula (1), W is a degradable linker that is specifically cleaved by intracellular lysosomal enzymes. Such linker is, for example, a structure based on peptide. Degradable peptide linkers generally have good blood stability because lysosomal enzymes are activated only in the low pH environment of intracellular lysosomes. The release of a drug from an antibody is specifically caused by the action of lysosomal enzymes such as cathepsin and plasmin. These enzymes may be present at high levels in certain tumor tissues. In certain embodiments, the linker can be cleaved by a lysosomal enzyme, and examples of the lysosomal enzyme include cathepsin B and the like.

W in the formula (1) is not particularly limited as long as it is an oligopeptide having 2 to 4 residues that is stable in the blood in a living body and degraded by an intracellular enzyme. In order to maximize masking of the hydrophobicity of a drug during the preparation of an antibody-drug conjugate and suppress the aggregation caused by the hydrophobicity of the drug, it is preferable to use an oligopeptide containing an amino acid with higher hydrophilicity. In certain embodiments, dipeptides are more preferred than longer peptides because longer peptides are hydrophobic.

On the other hand, cathepsin B, which is a lysosomal enzyme, has the property of efficiently hydrolyzing oligopeptides having highly hydrophobic amino acids (Vieira Portaro, F. C. et al. Biochem. J. 2000, 347:123-129, Cezari, M. H. S. et al. Biochem. J. 2002, 368:365-369). Therefore, W in the formula (1) is preferably an oligopeptide with 2-4 residues and having at least one hydrophobic neutral amino acid having a hydropathy index of not less than 2.5, specifically, phenylalanine, leucine, valine, or isoleucine, and an oligopeptide with 2-4 residues and having valine or phenylalanine is further preferable. The hydropathy index, which was created by Kyte and Doolittle and quantitatively indicates the hydrophobicity of amino acids, shows that the higher the value, the more hydrophobic the amino acid is (Kyte J & Doolittle RF, 1982, J Mol Biol, 157:105-132.).

As an amino acid to be combined with the above-mentioned hydrophobic amino acid, W in the formula (1) is preferably an oligopeptide with 2 to 4 residues and having at least one neutral amino acid whose Log P value calculated by X Log P3 is smaller than −2.5, specifically, alanine, glycine, citrulline, proline, serine, asparagine, more preferably an oligopeptide with 2 to 4 residues and having at least one of alanine, glycine, citrulline. Here, "Log P" is defined as the logarithm of the partition coefficient of octanol/water, and is a value that becomes an index of hydrophobicity, where smaller values mean higher hydrophilicity. In addition, "X log P3" is a method created by Cheng et al. for calculating the Log P value (Cheng, T. et al. J Chem Inf Model. 2007, 47:2140-2148).

In the formula (1), moreover, W is preferably an oligopeptide with 2 to 4 residues having glycine as the C-terminal amino acid. When a C-terminal carboxyl group is reacted, it is basically necessary to activate the C-terminal carboxyl group with a condensing agent and the like. It is known that epimerization tends to occur in amino acids other than glycine and stereoisomer is by-produced in this activation step. By using an achiral glycine as the C-terminal amino acid of the oligopeptide, a highly pure target product free from by-production of stereoisomer can be obtained.

In the formula (1), W is preferably an oligopeptide with 2 to 4 residues composed of an amino acid not including amino acids having an amino group or a carboxyl group in the side chain, specifically, lysine, aspartic acid, or glutamic acid. In the synthesis of the heterobifunctional monodisperse polyethylene glycol of the formula (1) of the present invention, the N-terminal amino group or the C-terminal carboxyl group of oligopeptide is used for the reaction when introducing the oligopeptide into the polyethylene glycol part. However, when an amino acid having an amino group or a carboxyl group in the side chain is contained in the oligopeptide, impurity in which the polyethylene glycol part is introduced into not only the intended N-terminal amino group or C-terminal carboxyl group, but also amino group or carboxyl group in the side chain are generated. Since this impurity is difficult to remove by a purification step such as general extraction or crystallization, to obtain the desired product with high purity, it is desirable to use an oligopeptide composed of amino acids having no amino group or carboxyl group in the side chain. The amino acids to be used here are $\alpha$-amino acids and are basically in the L form.

Cysteine, which is a neutral amino acid, has a thiol group and forms a disulfide bond with other thiol groups. Thus, in the formula (1), W is desirably an oligopeptide composed of amino acids not including cysteine.

W in the formula (1) is not particularly limited as long as it is stable in blood in a living body, degraded by intracellular enzymes, and is an oligopeptide with 2-4 residues composed of neutral amino acids excluding cysteine. Specific examples thereof include glycine-phenylalanine-leucine-glycine, glycine-glycine-phenylalanine-glycine, glycine-phenylalanine-glycine, glycine-leucine-glycine, valine-citrulline-glycine, valine-alanine-glycine, valine-citrulline, valine-alanine, phenylalanine-glycine and the like, of which preferred are glycine-phenylalanine-leucine-glycine, glycine-glycine-phenylalanine-glycine, valine-citrulline-glycine, valine-alanine-glycine, valine-citrulline, valine-alanine, phenylalanine-glycine, more preferably valine-citrulline, valine-alanine, and phenylalanine-glycine, and more preferred is valine-citrulline.

Z in the formula (1) is a self degradable spacer that further separates a drug from the site where the peptide linker for W is enzymatically cleaved. When the drug and the peptide linker are directly bonded, the peptide linker part remains in the drug when the peptide linker is cleaved, which may then cause decreased activity of the drug. The use of a self degradable spacer allows the release of drugs not containing a peptide linker, during hydrolysis of the amide bond.

One self degradable spacer is a bifunctional para-aminobenzyl alcohol group. This group is linked to a peptide via an amino group to form an amide bond. A drug having an amino group or a hydroxyl group can be bonded to the benzyl alcohol group of the linker via a carbamate bond or a carbonate bond (to afford para-aminobenzylcarbamate or para-aminobenzylcarbonate). The obtained prodrug is activated upon cleavage of the amide bond between peptide linkers to cause a 1,6-elimination reaction, and releases the drug not containing a peptide linker, carbon dioxide, and the rest of the linker group. In addition, this group causes an elimination reaction only when the amide bond on the C-terminal side of the peptide linker is cleaved, and releases the drug not containing a peptide linker. Therefore, when the C-terminal of the peptide linker is on the monodisperse polyethylene glycol side and not on the drug side, this group is not always necessary. The following scheme illustrates fragmentation of para-amidobenzylcarbamate or para-amidobenzylcarbonate, and release of the drug:

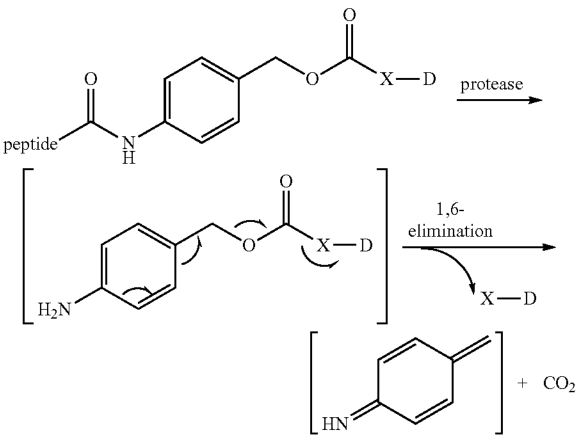

wherein X-D is a drug not containing a peptide linker.

In the formula (1), b is 0 or 1. When b is 0, the self degradable spacer for Z in the formula (1) is absent, and when b is 1, the self degradable spacer for Z in the formula (1) is present.

$A^1$ in the formula (1) of the present invention is a divalent spacer between the quaternary carbon atom of the branched portion, and W or $X^1$, $B^1$ in the formula (1) is a divalent spacer between the quaternary carbon atom of the branched portion, and W or $Y^1$, and $C^1$ in the formula (1) is a divalent spacer between Z, and $X^1$ or $Y^1$, each composed of a covalent bond.

To be specific, $A^1$ is $-L^1-(CH_2)_{m1}-L^2-$, $-L^1-(CH_2)_{m1}-L^2-(CH_2)_2—$, an amide bond, a urethane bond, a secondary amino group, or a single bond, preferably $-L^1-(CH_2)_{m1}-L^2-$, $-L^1-(CH_2)_{m1}-L^2-(CH_2)_{m2}—$, an amide bond, or a secondary amino group, further preferably $-L^1-(CH_2)_{m1}-L^2-(CH_2)_{m2}—$, an amide bond or a secondary amino group. In the formula, m1 and m2 are each independently an integer of 1-5.

$B^1$ is $—CH_2-L^3-$, $—CH_2-L^3-(CH_2)_{m3}-L^4-$ or $—CH_2-L^3-(CH_2)_{m3}-L^9-(CH_2)_{m4}—$, preferably $—CH_2-L^3-$ or $—CH_2-L^3-(CH_2)_{m3}-L^4-$. In the formula, m3 and m4 are each independently an integer of 1-5.

$C^1$ is $-L^5-(CH_2)_{m5}—$, $-L^5-(CH_2)_{m5}-L^6-(CH_2)_{m6}—$, an amide bond, or a single bond, preferably a single bond. In the formula, m5 and m6 are each independently an integer of 1-5.

In the aforementioned formula, $L^1$-$L^6$ are each independently a divalent spacer, specifically, an ether bond, a urethane bond, an amide bond, a secondary amino group, a carbonyl group, or a single bond.

$L^1$ and $L^2$ are preferably each independently a urethane bond, an amide bond, or a secondary amino group, $L^3$ is preferably an ether bond, a urethane bond, or a single bond, $L^4$ is preferably an amide bond, a urethane bond, a secondary amino group, a carbonyl group, or a single bond, $L^5$ is preferably a urethane bond, and $L^6$ is preferably an amide bond, a urethane bond, or a secondary amino group.

In the formula (1) of the present invention, a1 and a2 show the presence or absence of a spacer part represented by $—W—(Z)_b—C^1—$ in the formula (1). In a certain embodiment, a2=0 when a1=1, and in a certain other embodiment, a2=1 when a1=0.

A typical synthesis example of the heterobifunctional monodisperse polyethylene glycol of the formula (1) in a preferred embodiment of the present invention is described below; however, the present invention is not limited thereto.

(A) The heterobifunctional monodisperse polyethylene glycol of the formula (1) in a preferred embodiment of the present invention can be produced, for example, by the following steps.

(3)

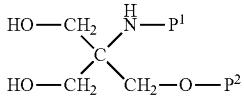

(in the formula (3), $P^1$ is an amino-protecting group; and $P^2$ is a hydroxy-protecting group.)

A compound represented by the aforementioned formula (3) is subjected to a nucleophilic substitution reaction with an alkyl or aryl sulfonic acid ester of monomethyl monodisperse polyethylene glycol, or a halide of monomethyl monodisperse polyethylene glycol in an anhydrous solvent in the presence of a strong base to obtain a compound represented by the following formula (4).

As used herein, the "protecting group" is a component that prevents or inhibits the reaction of a particular functional group in a molecule under certain reaction conditions. Protecting groups vary depending on the kind of the functional group to be protected, the conditions to be used and the presence of other functional group or protecting group in the molecule. Specific examples of the protecting group can be found in many general books, and they are described in, for example, "Wuts, P. G. M.; Greene, T. W. Protective Groups in Organic Synthesis, 4th ed.; Wiley-Interscience: New York, 2007". The functional group protected by a protecting group can be deprotected, that is, chemically reacted, using a reaction condition suitable for each protecting group, whereby the original functional group can be regenerated. Representative deprotection conditions for protecting groups are described in the aforementioned literature.

A preferred combination of a functional group to be protected and a protecting group is, for example, an acyl-based protecting group and a carbamate-based protecting group when the functional group to be protected is an amino group. Specific examples thereof include a trifluoroacetyl group, a 9-fluorenylmethyloxycarbonyl group, a t-butyloxycarbonyl group, and a 2-(trimethylsilyl)ethyloxycarbonyl group. When the functional group to be protected is a hydroxy group, for example, a silyl-based protecting group and an acyl-based protecting group can be mentioned, specifically, a t-butyldiphenylsilyl group, a t-butyldimethylsilyl group, a triisopropylsilyl group, an acetyl group, and a pivaloyl group.

When the functional group to be protected is carboxy group, for example, an alkyl ester-based protecting group and a silyl ester-based protecting group can be mentioned, specifically a methyl group, a 9-fluorenylmethyl group, and a t-butyldimethylsilyl group. When the functional group to be protected is a sulfanyl group, for example, a thioether-based protecting group, a thiocarbonate-based protecting group, and a disulfide-based protecting group can be mentioned, specifically an S-2,4-dinitrophenyl group, an S-9-fluorenylmethyloxycarbonyl group, and an S-t-butyl disulfide group. In addition, a bifunctional protecting group capable of simultaneously protecting two functional groups of the same type or different types may also be used. As a preferred combination of a functional group to be protected and a protecting group, when the functional groups to be protected are two hydroxy groups, for example, a cyclic acetal-based protecting group and a cyclic silyl-based protecting group can be mentioned, specifically a 2,2-dimethyl-1,3-dioxolane group, a 2,2-dimethyl-1,3-dioxane group, a 2-phenyl-1,3-dioxolane group, a 2-phenyl-1,3-dioxane group, and a di-t-butylsilylene group. when the functional groups to be protected are an amino group and a hydroxy group, for example, an oxazoline-based protecting group can be mentioned, specifically a 2-phenyloxazoline group.

Typical deprotection conditions for protecting groups are described in the aforementioned literatures, and reaction conditions suitable for each protecting group can be selected. However, when the functional group contained in the structure does not inhibit chemical reactions of other functional groups even though it is not protected with a protecting group, it is not necessary to use a protecting group.

(4)

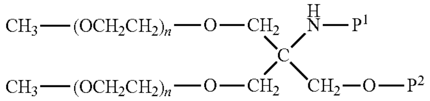

After deprotecting the protecting group $P^1$ of the compound represented by the aforementioned formula (4), an oligopeptide in which the N-terminal amino group is protected by a protecting group $P^3$ is reacted in the presence of a condensing agent to obtain a compound represented by the following formula (5). Here, when the reaction conditions in which a hydroxy group does not react with a reaction reagent of an amino group are selected, the protecting group $P^2$ may also be deprotected at the same time as the protecting group $P^1$. Peptide in the following formula (5) is the same oligopeptide as the aforementioned W.

(5)

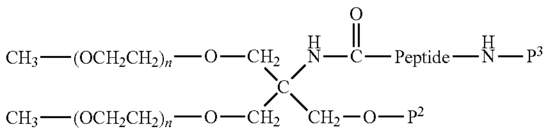

After deprotecting the protecting group $P^2$ of the compound represented by the aforementioned formula (5), active carbonation is performed using an active carbonation reagent in the presence of a base, and the active carbonate is further reacted with a carboxylic acid having an amino group, whereby a compound represented by the following formula (6) is obtained.

The active carbonation reagent is not particularly limited, and examples thereof include p-nitrophenyl chloroformate and di(N-succinimidyl) carbonate. In the following formula (6), m3 is as defined above.

(6)

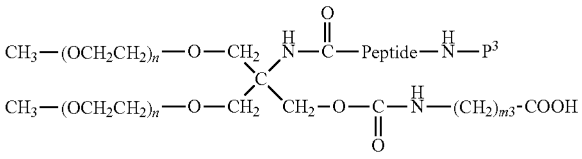

Further, by deprotecting the protecting group $P^3$ of the compound represented by the aforementioned formula (6), a compound represented by the following formula (7) is obtained.

(7)

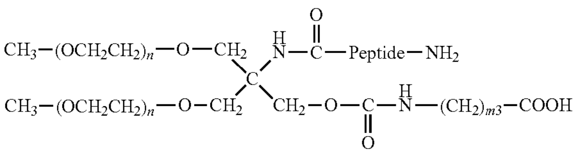

In another preferred embodiment of this step, after deprotecting the protecting group $P^2$ of the compound represented by the aforementioned formula (5), an acrylic acid ester in which a carboxylic acid is protected is reacted in the presence of a strong base, and further, the protecting group $P^3$ and a carboxylic acid-protecting group are deprotected, whereby a compound represented by the following formula (8) is obtained. In the following formula (8), m3 is as defined above, and the acrylic acid ester used in the reaction is not particularly limited as long as the number of carbon atoms satisfies m3; specifically, t-butyl acrylate or the like is used.

(8)

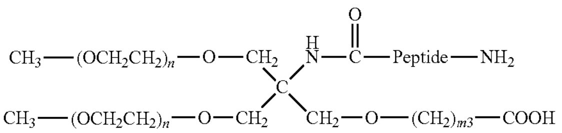

(B) In another preferred embodiment of the present invention, the heterobifunctional monodisperse polyethylene glycol of the formula (1) can be produced, for example, by the following steps.

After deprotecting the protecting group $P^2$ of the compound represented by the aforementioned formula (4), a carboxylic acid in which an amino group is protected by a protecting group $P^4$ is reacted in the presence of a condensing agent, whereby a compound represented by the following formula (9) is obtained. In the following formula (9), m1 and m3 are as defined above.

(9)

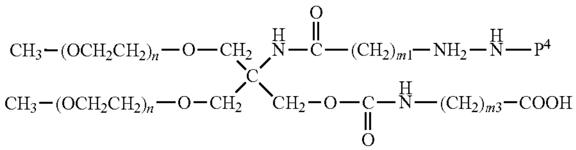

The compound represented by the aforementioned formula (9) is reacted, in the presence of a condensing agent, with an oligopeptide derivative in which the N-terminal amino group is unprotected and the C-terminal is condensed with para-aminobenzyl alcohol, and the protecting group $P^4$ is deprotected, whereby a compound represented by the following formula (10) is obtained. In the following formula (10), Peptide is as defined above.

(10)

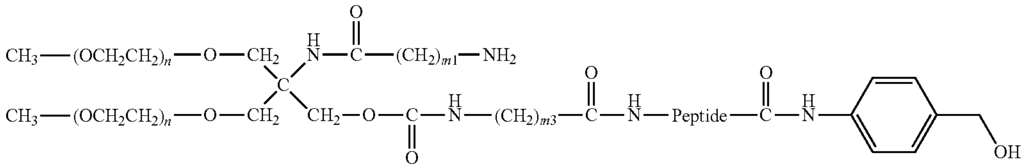

The compounds represented by the aforementioned formulas (7), (8) and (10) each have one amino group. Utilizing this, conversion to the aforementioned functional group for $X^1$ is possible.

The step of converting the terminal amino group of the aforementioned heterobifunctional monodisperse polyethylene glycol into another functional group is not particularly limited. Basically, conversion to various functional groups can be performed using a compound having an active ester group capable of reacting with an amino group, or a general reaction reagent such as acid anhydride, acid chloride, or the like.

For example, when conversion of the terminal amino group of the aforementioned heterobifunctional monodisperse polyethylene glycol to a maleimide group is desired, the desired product can be obtained by reacting with the following reagents.

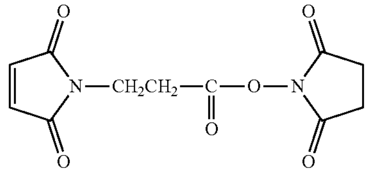

For example, when conversion of the terminal amino group of the aforementioned heterobifunctional monodisperse polyethylene glycol to a carboxyl group is desired, the desired product can be obtained by reacting with succinic anhydride or glutaric anhydride.

For example, when conversion of the terminal amino group of the aforementioned heterobifunctional monodisperse polyethylene glycol to a hydroxyl group is desired, the desired product can be obtained by condensation reacting with a ring-opening product of cyclic ester such as caprolactone and the like.

The compounds represented by the aforementioned formulas (6), (7), (8), and (9) all have one carboxylic acid, and the compound represented by the aforementioned formula (10) has one hydroxyl group. Utilizing this, conversion to the aforementioned functional group for $Y^1$ is possible.

The step of converting the carboxylic acid at the terminal of the aforementioned heterobifunctional monodisperse polyethylene glycol to other functional group is not particularly limited. For example, it can be converted to various functional groups by reacting a compound capable of converting carboxylic acid to an active ester group, specifically, a reagent such as N-hydroxysuccinimide in the presence of a condensing agent.

The step of converting the hydroxyl group at the terminal of the aforementioned heterobifunctional monodisperse polyethylene glycol to other functional group is not particularly limited. For example, it can be converted to various functional groups by using a compound capable of converting hydroxyl group to an active carbonate group, specifically, an active carbonation reagent such as p-nitrophenyl chloroformate and di(N-succinimidyl) carbonate.

In another embodiment of the present invention, an antibody-drug conjugate represented by the formula (2), containing a heterobifunctional monodisperse polyethylene glycol is provided.

(2)

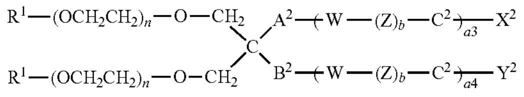

$R^1$ in the formula (2) of the present invention is a hydrocarbon group having 1-7 carbon atoms or a hydrogen atom, and a specific hydrocarbon group includes, for example, a methyl group, an ethyl group, a propyl group, an isopropyl group, a t-butyl group, a phenyl group and a benzyl group. A preferred embodiment of $R^1$ is a methyl group or a hydrogen atom, and a methyl group is further preferred. In the formula (2), $R^1$ is as defined above.

In the formula (2) of the present invention, n is an integer of 3-72, preferably 4-48, further preferably 6-36, particularly preferably 8-24, which shows a repeat unit number of the monodisperse polyethylene glycol.

In the formula (2), n is as defined above.

In the present specification, one of $X^2$ and $Y^2$ in the formula (2) is an antibody, and the other is a drug.

W, Z, and b in the formula (2) of the present invention mean the same as W, Z and b in the aforementioned formula (1).

$A^2$, $B^2$ and $C^2$ in the formula (2) of the present invention are divalent spacers, and each is composed of a covalent bond.

Specifically, $A^2$ is $-L^1-(CH_2)_{m1}-L^1-$, $-L^1-(CH_2)_{m1}-L^8-$, $-L^1-(CH_2)_{m1}-L^2-(CH_2)_{m2}-L^8-$, or $-L^8-$, preferably $-L^1-(CH_2)_{m1}-L^8-$, $-L^1-(CH_2)_{m1}-L^2-(CH_2)_{m2}-L^8-$, or $-L^8-$. In the formulas, $L^1$, $L^2$, m1, and m2 are as defined above.

$B^2$ is $—CH_2-L^9-$, $—CH_2-L^9-(CH_2)_{m3}-L^{10}-$, $—CH_2-L^9-(CH_2)_{m3}-L^{10}-(CH_2)_{m4}-L^{11}-$, $—CH_2-L^{12}-$, $—CH_2-L^9-(CH_2)_{m3}-L^{12}$, or $—CH_2-L^9-(CH_2)_{m3}-L^1-(CH_2)_{m4}-L^{12}-$, preferably $—CH_2-L^9-(CH_2)_{m3}-L^{10}-$, $—CH_2-L^9-(CH_2)_{m3}-L^{12}-$ or $—CH_2-L^9-(CH_2)_{m3}-L^{10}-(CH_2)_{m4}-L^{12}$, further preferably $—CH_2-L^9-(CH_2)_{m3}-L^{10}-$ or $—CH_2-L^9-(CH_2)_{m3}-L^{12}-$. In the formulas, m3 and m4 are as defined above.

In the aforementioned formulas, $L^7$, $L^9$, $L^{10}$, and $L^{11}$ are each independently an ether bond, a urethane bond, an amide bond, a secondary amino group, or a carbonyl group.

$L^7$ and $L^{11}$ are each a bond formed with W in the aforementioned formula (1), and are preferably each independently an amide bond or a secondary amino group, $L^9$ is preferably an ether bond or a urethane bond, and $L^{10}$ is preferably a urethane bond, an amide bond, or a secondary amino group.

$L^8$ and $L^{12}$ in the aforementioned formulas, when a3=0 and a4=0, respectively, are atomic groups that can be formed between a functional group contained in $X^1$ or $Y^1$ of the heterobifunctional monodisperse polyethylene glycol represented by the aforementioned formula (1), and a functional group present in the antibody for $X^2$ or $Y^2$, specifically an amide bond, a urethane bond, a bond of maleimide and thiol, a thioether bond, a disulfide bond, a carbonate bond, an ester bond, an ether bond, a 1H-1,2,3-triazole-1,4-diyl structure, a secondary amino group, a hydrazide group, an oxyamide group, a hydrocarbon group containing these, or a single bond.

$C^2$ is an atomic group that can be formed between a functional group contained in $X^1$ or $Y^1$ of the heterobifunctional monodisperse polyethylene glycol represented by the aforementioned formula (1), and a functional group present in an antibody or a drug in the presence of a peptide linker for W, specifically an amide bond, a urethane bond, a bond of maleimide and thiol, a thioether bond, a disulfide bond, a carbonate bond, an ester bond, an ether bond, a 1H-1,2,3-triazole-1,4-diyl structure, a secondary amino group, a hydrazide group, an oxyamide group, or a hydrocarbon group containing these.

In the formula (2) of the present invention, a3 and a4 show the presence or absence of a spacer part represented by $—W—(Z)_b—C^2—$ in the formula (2). When $X^2$ is a drug, a3=1 and a4=0, and when $Y^2$ is a drug, a3=0 and a4=1.

In a specific embodiment of the present invention, the antibody-drug conjugate (ADC) is a compound represented by the following formula (I) or a salt thereof, wherein Ab is an antibody, D is a drug, L is a linker composed of a heterobifunctional monodisperse polyethylene glycol represented by the aforementioned formula (1), and k is the number of the linker-drug conjugate (D-L) units to be bonded to the antibody.

$$(D—L)_k—Ab \qquad (I)$$

Specific embodiments of the antibody (Ab), drug (D), linker (L), and the binding mode of linker-drug conjugate (D-L) in the present invention, and the number of drugs bound to the ADC are described below.

The term "antibody" in the present specification is used in its broadest sense and specifically covers monoclonal antibodies, polyclonal antibodies, dimers, multimers, multispecific antibodies (e.g., bispecific antibodies), and antibody fragments as long as they exhibit the desired biological activity (Miller, K. et al. J. Immunol. 2003, 170, 4854-4861).

Antibodies may be derived from mouse antibodies, human antibodies, humanized antibodies, chimeric antibodies, or other species. Antibodies are proteins produced by the immune system and capable of recognizing and binding to specific antigens (Janeway, C.; Travers, P.; Walport, M.; Shlomchik, M. Immunobiology, 5th ed.; Garlan Publishing: New York, 2001). The target antigen generally has a number of binding sites (also called epitopes) recognized by the CDRs on multiple antibodies. Antibodies that specifically bind to different epitopes have different structures. Therefore, one antigen may have more than one corresponding antibodies. An antibody encompasses a full-length immunoglobulin molecule, or an immunologically active portion of a full-length immunoglobulin molecule (i.e., a molecule containing an antigen of interest or an antigen-binding site that immunospecifically binds to that portion). Such targets include, but are not limited to, cancer cells, and cells that produce autoimmune antibodies associated with autoimmune diseases. The immunoglobulins disclosed in the present specification may be immunoglobulin molecules of any type (e.g., IgG, IgE, IgM, IgD, and IgA), class (e.g., IgG1, IgG2, IgG3, IgG4, IgA1, and IgA2), or subclass. The above-mentioned immunoglobulins may be derived from any species. However, in one embodiment, the above-mentioned immunoglobulin is of human origin, mouse origin, or rabbit origin.

Polyclonal antibodies are heterogeneous populations of antibody molecules, such as those derived from the serum of immunized animals. Polyclonal antibodies against the antigen of interest may be generated using various procedures known in the art. For example, to produce polyclonal antibodies, target antigens or derivatives thereof may be injected to immunize a variety of host animals, including but not limited to rabbits, mice, rats and guinea pigs. Depending on the host species, various adjuvants may be used to increase the immune response, including but not limited to Freund's (complete and incomplete) adjuvants, mineral gels such as aluminum hydroxide, surfactants such as lysolecithin, pluronic polyols, polyanions, peptides, oil emulsions, keyhole limpet hemocyanin, dinitrophenol, and potentially useful human adjuvants such as BCG (bacille Calmett-Guerin) and *Corynebacterium parvum*. Such adjuvants are also known in the art.

Monoclonal antibody is a uniform population of antibodies against a particular antigenic determinant (e.g., cellular antigens (cancer or autoimmune cell antigen), viral antigens, microbial antigens, proteins, peptides, carbohydrates, chemical substances, nucleic acids or antigen binding fragments thereof). Monoclonal antibody (mAb) to the antigen of interest may be prepared using any technique known in the art. Such technique includes, but are not limited to, the hybridoma technique first described by Kohler, G; Milstein, C. Nature 1975, 256, 495-497), human B cell hybridoma technique (Kozbor, D. et al. Immunol. Today 1983, 4, 72-79) and the EBV-hybridoma technique (Cole, S. P. C. et al. Monoclonal Antibodies and Cancer Therapy; Alan R. Liss: New York, 1985, pp. 77-96). Such antibodies may be of any immunoglobulin type including IgG, IgM, IgE, IgA and IgD or any subspecies thereof. Hybridomas that produce monoclonal antibodies in the present invention may be cultured in vitro or in vivo.

Monoclonal antibodies include, but are not limited to, human monoclonal antibodies, humanized monoclonal antibodies, chimeric monoclonal antibodies, and antibody fragments. Human monoclonal antibodies may be made by any of many techniques known in the art (e.g., Teng, N. N. et al. Proc. Natl. Acad. Sci. USA. 1983, 80, 7308-7312, Kozbor, D. et al. Immunology Today 1983, 4, 72-79, Olsson, L. et al. Meth. Enzymol. 1982, 92, 3-16, and U.S. Pat. Nos. 5,939,598 and 5,770,429). Recombinant antibodies such as chimeric monoclonal antibodies and humanized monoclonal antibodies can be made using standard recombinant DNA techniques known in the art (e.g., U.S. Pat. Nos. 4,816,567 and 4,816,397).

The immunogenicity of an antibody can also be reduced by a surface reconstruction (resurfacing) treatment of the antibody (U.S. Pat. No. 5,225,539, EP-B-0239400, EP-B-0519596, EP-B-0592106).

In one embodiment of the invention, the antibody may be a bispecific antibody. Methods for making bispecific antibodies are known in the art. Conventional methods of producing full length bispecific antibodies utilize simultaneous expression of two immunoglobulin heavy chain-light chain pairs when the two chains have different specificities (see Milstein, C et al. Nature 1983, 305, 537-539). As another method, bispecific antibodies can also be produced by fusing antibody variable domain with the desired binding specificity (antibody-antigen binding site) with immunoglobulin constant domain sequence.

Other useful antibodies include, but are not limited to, antibody fragments such as F(ab')2 fragment, Fab' fragment, Fab fragment, Fvs, single-chain antibody (SCA) (e.g., described in U.S. Pat. No. 4,946,778, Bird, R. E. et al. Science 1988, 242, 423-442, Huston, J. S. et al. Proc. Natl. Acad. Sot USA 1988, 85, 5879-5883 and Ward, E. S. et al. Nature 1989, 334, 544-554), scFv, sc-Fv-Fc, FvdsFv, minibody, diabody, triabody, tetrabody, and CDR, and any other molecules with the same specificity as that of the antibody such as domain antibody and the like.

In a preferred embodiment of the present invention, known antibodies for the treatment or prophylaxis of cancer may be used. All target proteins can be targeted by the antibody, including any target protein whose expression correlates with the expression of cancer, cell proliferation disorder, or tumor on the cells.

In a preferred embodiment of the present invention, the antibody is useful in the treatment of cancer. Examples of antibodies available for the treatment of cancer include, but are not limited to, Rituxan (registered trade mark) (Genentech Inc.) which is a chimeric anti-CD20 monoclonal antibody for the treatment of patients with non-Hodgkin's lymphoma, Ovarex (AltaRex Corp.) which is a mouse antibody for the treatment of ovarian cancer, Panorex (Glaxo Wellcome Plc) which is a mouse IgG2a antibody for the treatment of colorectal cancer, cetuximab erbitux (ImClone Systems incorporated) which is an anti-EGFR IgG chimeric antibody for the treatment of epithelial cell growth factor positive cancer such as head cancer and neck cancer, Vitaxin (MedImmune Limited) which is a humanized antibody for the treatment of sarcoma, Campath I/H (Leukosite Inc.) which is a humanized IgG1 antibody for the treatment of chronic lymphocyte leukemia (CLL), Smart M195 (Protein Design Labs, Inc.) which is a humanized anti-CD33 IgG antibody for the treatment of acute myelogenous leukemia (AML), Lymphocide (Immunomedics, Inc.) which is a humanized anti-CD22 IgG antibody for the treatment of non-Hodgkin lymphoma, Smart ID10 (Protein Design Labs, Inc.) which is a humanized anti-HLA-DR antibody for the treatment of non-Hodgkin lymphoma, Oncolym (Techniclone Corp.) which is a radiolabeled mouse anti-HLA-Dr10 antibody for the treatment of non-Hodgkin lymphoma, Allomune (Biotransplant Inc.) which is a humanized anti-CD2 mAb for the treatment of Hodgkin's disease or non-Hodgkin lymphoma, avastin (Genentech Inc.) which is a anti-VEGF humanized antibody for the treatment of lung cancer and colorectal cancer, Epratuzamab (Immunomedics, Inc. and Amgen Inc.) which is an anti-CD22 antibody for the treatment of non-Hodgkin lymphoma, and CEAcide (Immunomedics, Inc.) which is a humanized anti-CEA antibody for the treatment of colorectal cancer.

In a preferred embodiment of the present invention, the antibody is an antibody against the following antigens. CA125, CA15-3, CA19-9, L6, Lewis Y, Lewis X, alfa fetoprotein, CA242, placenta alkali phosphatase, prostate-specific membrane antigen, EphB2, TMEFF2, prostatic acid phosphatase, epithelial growth factor, MAGE-1, MAGE-2, MAGE-3, MAGE-4, antitransferrin receptor, p97, MUC1-KLH, CEA, gp100, MART1, prostate-specific antigen, IL-2 receptor, CD20, CD52, CD33, CD22, human chorionic gonadotropin, CD38, CD40, mucin, P21, MPG and Neu cancer gene product. Some specific useful antibodies include, but are not limited to, mAbs against CD40 antigens such as BR96 mAb (Trail, P. A. et al. Science 1993, 261, 212-215), BR64 (Trail, P. A. et al. Cancer Research 1997, 57, 100-105), S2C6 mAb (Francisco, J. A. et al. Cancer Res. 2000, 60, 3225-3231) and the like, other anti-CD40 antibodies disclosed in US-A-2003/0211100 and US-A-2002/0142358, mAbs against CD70 antigen such as 1F6 mAb and 2F2 mAb, and mAbs against CD30 antigens such as AC10 (Bowen, M. A. et al. J. Immunol. 1993, 151, 5896-5906, Wahl, A. F. et al. Cancer Res. 2002, 62(13), 3736-42) or MDX-0060 (US-A-2004/0006215) and the like.

Drugs that can be used in the present invention include chemotherapeutic agents. Chemotherapeutic agents are compounds useful in the treatment of cancer. Examples of the chemotherapeutic agent include:

alkylating agents, for example, thiotepa and cyclophosphamide (CYTOXAN (trade mark)); alkylsulfonates, for example, busulfan, improsulfan, and piposulfan; aziridines including, for example, benzodopa, carboquone, meturedopa, and uredopa; ethyleneimines and methylamelamines including altretamine, triethylenemelamine, trietylenephosphoramide, triethylenethiophosphoramide, and trimethylolomelamine; acetogenins (particularly bullatacin and bullatacinone); camptothecin (including synthesis analog topotecan); bryostatin; callystatin; CC-1065 (including adozelesin, carzelesin and bizelesin as synthesis analogs thereof); cryptophycins (particularly, cryptophycin 1 and cryptophycin 8); dolastatin; duocarmycin (including synthesis analogs thereof KW-2189 and CBI-TMI); eleutherobin; pancratistatin; sarcodictyin; spongistatin; nitrogen mustard, for example, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas, for example, carmustine, chlorozotocin, fotemustine, lomustine, nimustine, ranimustine; antibiotics, for example, enediyne antibiotic (e.g., calicheamicin, particularly, calicheamicin gamma 1 and calicheamicin theta I, see, for example, Angew Chem Intl. Ed. Engl. 33:183-186 (1994); dynemicin, including dynemicin A; esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; antimetabolites, for example, methotrexate and 5-fluorouracil (5-FU); folic acid analogs, for example, denopterin, methotrexate, pteropterin, trimetrexate; purine analogs, for example, fludarabine, 6-mercaptopurine, thiamiprine, thioguanine; pyrimidine analogs, for example, ancitabine, azacytidine, 6-azauridine, carmofour, cytarabine, dideoxyuridine, doxifluridine, enocitabine, Floxuridine, 5-FU; androgens, for example, calusterone, dromostanolone propionate, epitiostanol, mepitiostane, testrolactone; anti-adrenals, for example, aminoglutethimide, mitotane, trilostane; folic acid supplements, for example, frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; epothilone; etoglucid; gallium nitrate; hydroxyurea; lentinan; lonidamine; maytansinoids, for example, maytansine and ansamitocins; mitoguazone; mitoxantrone; mopidamol; nitracrine; pentostatin; phenamet; pirarubicin; podophyllinic acid; 2-ethylhydrazide; procarbazine; PSK (registered trade mark); razoxane; rhizoxin; sizofiran; spirogermanium; tenuazonic acid; triaziquone; 2,2',2"-trichlorotriethylamine; trichothecenes, (particularly T-2 toxin, verracurin A, roridin A, and anguidine); urethane; vindesine; dacarbazine; mannomustine; mitobronitol; mitolactol; pipobroman; gacytosine; arabinoside (“Ara-C”); cyclophosphamide; thiotepa; taxoids, for example, paclitaxel (TAXOL (registered trade mark), Bristol-Myers Squibb Oncology) and doxetaxel (TAXOTERE (registered trade mark), Rhone-Poulenc Rorer); chlorambucil; gemcitabine; 6-thioguanine; mercaptopurine; methotrexate; platinum analogs, for example, cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterine; xeloda; ibandronate; CPT-11; topoisomerase inhibitor RFS2000; difluoromethylomithine (DMFO); retinoic acid; capecitabine; and pharmaceutically acceptable salts, acids, or derivatives of any of those mentioned above.

Anti-hormonal agents that act to regulate or inhibit the action of hormones on tumors, for example, the following are also included in this definition: for example, anti-estrogen drugs containing tamoxifen, raloxifene, 4 (5)-imidazoles that inhibit aromatase, 4-hydroxytamoxifen, trioxifene, keoxifene, LY117018, onapristone, and toremifene (Fareston); as well as anti-androgen drugs, for example, flutamide, nilutamide, bicalutamide, leuprolide, and goserelin; siRNA and pharmaceutically acceptable salts, acids, or derivatives of any of those mentioned above. Other chemotherapeutic agents that can be used with the present invention are disclosed in US-A-2008/0171040 and US-A-2008/0305044, which are incorporated herein by reference.

In a preferred embodiment of the present invention, the chemotherapeutic agent is a low-molecular drug. The low-molecular drug preferably has a molecular weight of 100-1500, more preferably 120-1200, further preferably 200-1000. Typically, it is widely used to refer to organic, inorganic, or organometallic compounds having a molecular weight of less than about 1000. The low-molecular drug of the present invention includes oligopeptides and other biomolecules having a molecular weight of less than about 1000. The low-molecular drugs are well characterized in the art in, for example, WO 05/058367, EP-A-85901495 and EP-A-8590319, and U.S. Pat. No. 4,956,303, which are incorporated herein by reference.

A preferred low-molecular drug of the present invention is a low-molecular drug that can be linked to an antibody. The present invention includes known drugs and drugs that may become known. Particularly preferred low-molecular drugs include cytotoxic drugs.

Preferred cytotoxic drugs are maytansinoids, CC-1065 analogs, morpholinos, doxorubicins, taxanes, cryptophycins, epothilones, calicheamicins, auristatins, and pyrrolobenzodiazepine dimers.

The antibody-drug conjugate containing the heterobifunctional monodisperse polyethylene glycol represented by the formula (2) of the present invention can be prepared by binding a drug to an antibody by using the heterobifunctional monodisperse polyethylene glycol represented by the formula (1). As a method for preparing an antibody-drug conjugate represented by the aforementioned formula (2), it may be prepared by binding a drug to a heterobifunctional monodisperse polyethylene glycol represented by the aforementioned formula (1) and then binding an antibody thereto, or prepared by binding a heterobifunctional monodisperse polyethylene glycol represented by the aforementioned formula (1) to an antibody and then binding a drug thereto. In addition, purification may be performed after binding either one of the antibody or the drug, or purification may be performed after binding both the antibody and the drug.

The compound in which a heterobifunctional monodisperse polyethylene glycol represented by the aforementioned formula (1) is bound to a drug can be purified by a purification means such as column chromatography, extraction, recrystallization, adsorbent treatment, reprecipitation, supercritical extraction, and the like. In addition, the compound in which a heterobifunctional monodisperse polyethylene glycol represented by the aforementioned formula (1) is bound to an antibody and an antibody-drug conjugate in which both an antibody and a drug are bound can be purified by a purification means such as column chromatography, extraction, adsorbent treatment, and the like.

A linker-drug conjugate in which a heterobifunctional monodisperse polyethylene glycol represented by the aforementioned formula (1) is bound to a drug can be prepared using a standard conjugation technique known in the art (e.g., U.S. Pat. Nos. 8,163,888, 7,659,241, 7,498,298, WO 2011/023883, WO 2005/112919).

A conjugate of an antibody, and a heterobifunctional monodisperse polyethylene glycol represented by the aforementioned formula (1) or a linker-drug conjugate composed of the linker and a drug can be synthesized under conditions where a functional group contained in the atomic group $X^1$ or Y in the formula (1) reacts with a functional group in the antibody to form a covalent bond. Generally, the chemical reactions used cannot alter the integrity of the antibody, for example, the target-binding ability of the antibody. Preferably, the binding properties of the conjugated antibody are similar to those of the non-conjugated antibody.

A conjugate in which a heterobifunctional monodisperse polyethylene glycol represented by the aforementioned formula (1) or a linker-drug conjugate composed of the linker and a drug is bonded to an antibody can be made using chemical reactions and techniques known in the art (e.g., "Arnon, R. et al.; Monoclonal antibodies as carriers for immunotargeting of drugs; Monoclonal antibodies for cancer detection and therapy. Academic Press; Baldwin, R. W. et al. eds.; London, 1985, 367-382", "Hellstrom, K. E. et al.; Antibodies for drug delivery; Controlled Drug Delivery; Robinson, J. R. et al. eds.; Marcel Dekker, Inc.; New York; 1987, 623-653", "Thorpe, P. E. et al. Monoclonal antibodies, 1985, 84: 475-506", "Order, S. E.; Analysis, results, and future prospective of the therapeutic use of radiolabeled antibody in cancer therapy; Monoclonal antibodies for cancer detection and therapy. Academic Press; Baldwin, R. W. et al. eds.: London, 1985", "Thorpe, P. E et al. Immunol Rev. 1982, 62:119-158" and WO 89/12624).

A linker-drug conjugate composed of a drug, and a heterobifunctional monodisperse polyethylene glycol represented by the aforementioned formula (1) or the linker can be bound to the side chain of the amino acid residue of the antibody. For example, it is a primary amino group of available lysine residues, or a free thiol group of available cysteine residues. In one embodiment of the present invention, the bond formed by reaction with the antibody is a bond formed with the amino group of the antibody and is, for example, an amide bond, a thioether bond, or a thiourea bond, preferably an amide bond. In certain embodiments, the bond formed by reaction with the antibody is a bond formed with the thiol group of the antibody and is, for example, an amide bond, a bond of maleimide and thiol, a thioether bond, or a thiourea bond, preferably a bond of maleimide and thiol or a thioether bond.

In a preferred embodiment of the invention, the binding of the heterobifunctional monodisperse polyethylene glycol or a linker-drug conjugate of the invention, to the antibody is the binding of maleimide to thiol or a thioether bond which results from a reaction with an interchain cysteine residue of the antibody. In order to obtain a more homogeneous ADC, it is desirable that an average of 8 drugs are bound to an antibody by reaction with the cysteine residue generated by reducing 4 pairs of interchain disulfide bonds of the antibody.

A functional group for linking a heterobifunctional monodisperse polyethylene glycol represented by the aforementioned formula (1) or a linker-drug conjugate consisting of the linker and a drug to a primary amino group of an available lysine residue is known, and is not particularly limited. For example, an NHS-ester group, an N-succinimidyl carbonate group, and a p-nitrophenyl carbonate group can be mentioned.

A functional group for linking a heterobifunctional monodisperse polyethylene glycol represented by the aforementioned formula (1) or a linker-drug conjugate consisting of the linker and a drug to a free thiol group of an available cysteine residue is known, and is not particularly limited. For example, an α-haloacetyl group and a maleimide group can be mentioned.

However, a functional group of an antibody that reacts with a heterobifunctional monodisperse polyethylene glycol represented by the aforementioned formula (1) or a linker-drug conjugate composed of a drug and the linker is not limited to the side chain group of the naturally occurring amino acid, and can be converted to another useful functional group by reacting the amino acid side chain of the antibody with a suitable small molecule. For example, a side chain of an amino acid, such as an amino group, can be converted to another useful functional group, such as a hydroxy group, by reacting a suitable small molecule with the amino group.

As for the functional group of the antibody for conjugation, an amino acid may be introduced at any position of the antibody by genetic engineering operation, and the amino acid to be introduced may be either a natural type or a non-natural type. A genetic engineering technique for introducing amino acid residues into antibodies is described in, for example, "Axup, J. Y. et al. Proc Natl Acad Sci. 2012, 109:16101-16106" and "Tian, F. et al. Proc Natl Acad Sci. 2014, 111:1766-1771".

A heterobifunctional monodisperse polyethylene glycol represented by the aforementioned formula (1) or a linker-drug conjugate composed of a drug and the linker may be bound to an antibody site-nonspecifically or site-specifically. A site-specific conjugation is preferred.

An antibody-drug conjugate (ADC) represented by the formula (2) of the present invention, containing a heterobifunctional monodisperse polyethylene glycol can be prepared by a standard method similar to the methods described in "Hamblett, K. J. et al. Clin. Cancer Res. 2004, 10:7063-7070", "Doronina, S. O. et al. Nat Biotechnol. 2003, 21:778-784", "Francisco, J. A. et al. Blood, 2003, 102:1458-1465", "Chari, R. V. J. et al. Cancer Res. 1992, 52:127-131", and "Tumey, L. N. et al. ACS Med. Chem. Lett. 2016, 7:977-982". For example, an ADC having eight drugs per antibody, in which the linker-drug conjugate of the invention binds to an interchain cysteine residue of the antibody can be obtained by partially reducing the antibody at 37° C. for 1 hr with an excess amount of a reducing reagent such as dithiothreitol (DTT) or tris(2-carboxyethyl)phosphine (TCEP), then adding an excess amount, for example, 15 equivalents, of a linker-drug conjugate composed of a heterobifunctional monodisperse polyethylene glycol represented by the aforementioned formula (1) and a drug at 20° C. for 1 hr, and adding an excess amount, for example, 50 equivalents, of N-acetyl-L-cysteine to quench the reaction. The obtained ADC mixture can be purified by gel filtration chromatography using NAP (registered trade mark)-5 equilibrated with PBS, by desalting and removing the unreacted linker-drug conjugate, and can be further purified by size-exclusion chromatography. Then, the obtained ADC may be sterilized and filtered using, for example, a 0.2 μm filter and lyophilized for storage.

The number of drugs per antibody in ADC can be determined by methods known to those of skill in the art, such as ultraviolet/visible spectroscopy, mass spectrometry method, ELISA method, electrophoresis, HPLC, and combinations thereof (e.g., described in "Chen, J. et al. Anal. Chem. 2013, 85:1699-1704", "Valliere-Douglass, J. F. et al. Anal. Chem. 2012, 84:2843-2849", "Birdsall, R. E. et al. mABs, 2015, 7:1036-1044" and "Zhao, R. Y. et al. J. Med. Chem. 2011, 54:3606-3623"). In one embodiment, the average number of drugs for one antibody in the ADC can be calculated by ultraviolet/visible spectroscopy. Specifically, it can be calculated by measuring the UV absorbance of an aqueous antibody-drug conjugate solution at two different wavelengths, for example, 280 nm and 495 nm, and then performing the following calculation. Since the total absorbance at a certain wavelength is equal to the sum of the absorbances of all the absorbed chemical species existing in the system [absorbance additivity], assuming that there is no change in the molar absorption coefficients of the antibody and drug before and after the conjugation reaction of the antibody and the drug, the antibody concentration and the drug concentration in the antibody-drug conjugate are represented by the following relational formulas.

$$A280=\varepsilon D,280CD+\varepsilon A,280CA \quad \text{formula (i)}$$

$$A495=\varepsilon D,495CD+\varepsilon A,495CA \quad \text{formula (ii)}$$

$$DAR=CD/CA \quad \text{formula (iii)}$$

A280 indicates the absorbance of the aqueous antibody-drug conjugate solution at 280 nm, A495 indicates the absorbance of the aqueous antibody-drug conjugate solution at 495 nm, εA, 280 indicates the molar absorption coefficient of the antibody at 280 nm, εA, 495 indicates the molar absorption coefficient of the antibody at 495 nm, εD, 280 indicates the molar absorption coefficient of the linker-drug conjugate at 280 nm, εD, 495 indicates the molar absorption coefficient of the linker-drug conjugate at 495 nm, CA indicates the antibody concentration of the antibody-drug conjugate, and CD indicates the drug concentration of the antibody-drug conjugate. Assumed values are used for εA, 280 and εA, 495, and εA, 495 is generally 0. εD, 280 and εD, 495 can be obtained by measuring the absorbance of a solution in which the linker-drug conjugate to be used was dissolved at any molar concentration, and using the Lambert-Beer law (absorbance=mol concentration×molar absorption coefficient×cell optical path length). CA and CD can be obtained by measuring A280 and A495 of an aqueous antibody-drug conjugate solution, substituting these values into the formulas (i) and (ii) to solve the simultaneous equations. Furthermore, the average number of drugs bound per antibody can be obtained by dividing CD by CA.

The number of drugs bound to an antibody via the heterobifunctional monodisperse polyethylene glycol represented by the formula (1) of the present invention, which is shown by k in the aforementioned formula (I), can be defined, for example, by the average number of drugs per antibody. In the reaction of an antibody with a heterobifunctional monodisperse polyethylene glycol represented by the formula (1) of the present invention or linker-drug conjugate, the number of bindings can be determined by the number of reactive sites on the antibody with which the linker or linker-drug conjugate reacts. The reactive sites on the antibody may not be blocked completely, and conjugates with different numbers of drugs bound to the antibody may be mixed in the ADC after preparation. However, by controlling and purifying the reactive site, conjugates having a single number of drugs bound to the antibody can also be obtained. Therefore, while the number of drugs that bind to one antibody may be either an average value of distribution or a single value, a single value is preferred because the physical properties of ADC are stabilized when the distribution is small or absent. Thus, k in the aforementioned formula (I) is a certain number of distribution that is not an integer, or an integer.

In the embodiment of the present invention, the number of drugs bound per antibody is preferably 1-20, more preferably 2-16, further preferably 3-12, particularly preferably 4-8, most preferably 8.

The heterobifunctional monodisperse polyethylene glycol of the present invention is required to have the property of being specifically degraded in the cell and effectively releasing a drug in a sustained manner. To properly evaluate the property, for example, the following test is performed, based on which the intracellular degradability of the aforementioned heterobifunctional monodisperse polyethylene glycol, and the intracellular activity of the linker-bound drug can be evaluated.

The test method for evaluating the degradability of the aforementioned heterobifunctional monodisperse polyethylene glycol by enzymes in the cell is not particularly limited. For example, a test for confirming the degradation of a model compound or a drug, to which the linker is bound, by using a lysosomal enzyme which is an intracellular enzyme can be mentioned. Specifically, when the lysosomal enzyme is cathepsin B, a solution containing a model compound or a drug to which the aforementioned heterobifunctional monodisperse polyethylene glycol is bound is added to a cathepsin B/DTT solution prepared by adding a reducing agent DTT to cathepsin B, the mixture is incubated at 37° C., HPLC measurement of the sampled solution is performed, and the charts before and after the test are compared, whereby the degradability can be confirmed. Furthermore, when a new peak is found, the cleavage site of the linker and the structure of the released model compound or drug can be confirmed by confirming the mass chromatogram.

While the model compound to be used in the test is not particularly limited, when the aforementioned heterobifunctional monodisperse polyethylene glycol has a maleimide group as a functional group, it is preferable to use a model compound that reacts with a maleimide group since the cysteine residue of catepsin B reacts with the maleimide group to inhibit the enzyme reaction. Examples thereof include a compound having a thiol group, specifically, glutathione and the like.

The drug used in the test is not particularly limited as long as it is the drug shown above, and examples thereof include a drug having an amino group, specifically, doxorubicin and the like.

Furthermore, a test method for evaluating the intracellular pharmacological activity of the drug-linker compound to which the aforementioned heterobifunctional monodisperse polyethylene glycol is bound is not particularly limited. Examples thereof include a cytotoxicity test in which cells are cultured using a medium containing the drug-linker compound and the cell survival rate is calculated, and the like.

When the peptide linker introduced into the heterobifunctional monodisperse polyethylene glycol of the present invention is not degraded in cells, it is possible that the binding to the drug is not degraded in cells and the activity of the drug becomes low. It is shown that higher cell viability means lower activity of the drug. Therefore, the activity of the drug in cells by the use of the heterobifunctional monodisperse polyethylene glycol of the present invention can be evaluated by calculating the cell survival rate by this test and comparing with the cell survival rate of a control drug-linker compound not containing the peptide linker.

The cells and medium used here are not particularly limited. Specifically, the cell survival rate can be calculated by dissolving the drug-linker compound in medium RPMI-1640, culturing HeLa cells at 37° C., performing a color reaction by using a viable cell count measurement kit, and further measuring the absorbance. The cell survival rate is calculated by dividing the absorbance of the sample minus the absorbance of the blank, by the absorbance of only the cells that do not contain the sample.

In addition, the oligopeptide to be introduced into the heterobifunctional monodisperse polyethylene glycol of the present invention is required to have more hydrophilic property that does not interfere with the hydrophobic drug-masking effect of the linker. To properly evaluate the property, for example, the following test is performed, based on which the hydrophilicity of the aforementioned heterobifunctional monodisperse polyethylene glycol can be evaluated.

The test method for evaluating the hydrophilicity of peptide in the aforementioned heterobifunctional monodisperse polyethylene glycol is not particularly limited, and can be evaluated by methods known to those of skill in the art, such as HPLC by size-exclusion chromatography (SEC), ion exchange chromatography (IEC), reverse-phase (RP) chromatography and hydrophobic interaction chromatography (HIC) (e.g., "Mant, C. T. et al. Methods Mol Biol. 2007, 386:3-55"). In an exemplary embodiment, the hydrophilicity of the peptide can be evaluated by measuring the target compound under the same conditions using reverse-phase HPLC and comparing the retention times of the peak tops. In the case of reverse-phase HPLC, a shorter retention time is detected when the hydrophilicity of the target compound is higher.

EXAMPLE

The present invention is explained in more detail in the following by referring to Examples; however, the present invention is not limited thereto.

For $^1$H-NMR analysis, JNM-ECP400 or JNM-ECA600 manufactured by JEOL Datum Co., Ltd. was used. A 95 mm tube was used for the measurement, and when the deuterated solvent was $CDCl_3$, $CD_2Cl_2$, or DMSO-d6, tetramethylsilane (TMS) was used as the internal standard substance.

Example 1 Synthesis of Compound 11

Trishydroxymethylaminomethane (30.3 g, 250 mmol), sodium carbonate (5.30 g, 50 mmol), dehydrated methanol (237 g), and benzonitrile (5.15 g, 50 mmol) were charged in a 500 mL four-necked flask equipped with a thermometer, a nitrogen inlet tube, a stirrer, a Dean-stark tube, and a cooling tube, and reacted at 65° C. for 24 hr. After filtration, the solvent was evaporated under reduced pressure, the residue was dissolved by adding isopropyl alcohol and dichloromethane, and washed with 10 wt % brine. The organic layer was dried over anhydrous sodium sulfate, and filtered. The solvent was evaporated under reduced pressure. The residue was dissolved in tetrahydrofuran, hexane was added to perform crystallization, and filtration was performed to give the compound of the formula (11).

$^1$H-NMR ($CDCl_3$, internal standard TMS); δ(ppm): 3.06 (2H, brs, —O$\underline{H}$), 3.65-3.81 (4H, dd, >C(C$\underline{H}_2$OH)$_2$), 4.38 (2H, s, —CNO—C$\underline{H}_2$—), 7.32-7.83 (5H, m, $\underline{\text{arom. H}}$)

(11)

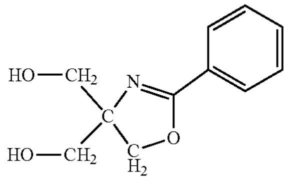

Example 2 Synthesis of Compound 12

Dodecaethylene glycol monomethyl ether (10.4 g, 18.5 mmol), toluene (52.0 g), triethylamine (2.44 g, 24.1 mmol), and methanesulfonyl chloride (2.34 g, 20.4 mmol) were charged in a 100 mL three-necked flask equipped with a thermometer, a nitrogen inlet tube, a stirrer, a Dean-stark tube, and a cooling tube, and reacted at 40° C. for 3 hr. The mixture was diluted with dichloromethane, washed with water, and the organic layer was dried over anhydrous magnesium sulfate. It was filtered and the solvent was evaporated under reduced pressure to give a compound of the formula (12).

$^1$H-NMR ($CDCl_3$, internal standard TMS); δ(ppm): 3.08 (3H, s, —O—$SO_2$—C$\underline{H}_3$), 3.38 (3H, s, —O—C$\underline{H}_3$), 3.45-3.85 (46H, m, $CH_3$—O—(C$\underline{H}_2$C$\underline{H}_2$O)$_{11}$—C$\underline{H}_2$CH$_2$—O—$SO_2$—$CH_3$), 4.38 (2H, m, —C$\underline{H}_2$—O—$SO_2$—$CH_3$)

(12)

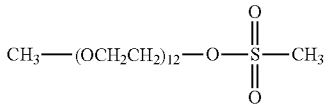

Example 3 Synthesis of Compound 13

A compound of the formula (11) (0.21 g, 1.01 mmol), dehydrated tetrahydrofuran (7.70 g), a compound of the formula (12) (2.46 g, 3.84 mmol), and 1M potassium tert-butoxide/tetrahydrofuran solution (3.72 g, 4.04 mmol) were charged in a 50 mL three-necked flask equipped with a thermometer, a nitrogen inlet tube, a stirrer, a Dean-stark tube, and a cooling tube, and reacted at 50° C. for 4 hr. Dichloromethane and 25 wt % brine were added and the mixture was washed with water. The organic layer was dried over anhydrous sodium sulfate, filtered and the solvent was evaporated under reduced pressure to give a compound of the formula (13).

$^1$H-NMR ($CDCl_3$, internal standard TMS); δ(ppm): 3.38 (6H, s, —O—C$\underline{H}_3$), 3.40-3.75 (100H, m, >C(C$\underline{H}_2$O)$_2$—, —O—(C$\underline{H}_2$C$\underline{H}_2$O)$_{12}$—, —CNO—C$\underline{H}_2$—), 4.36 (2H, s, —CNO—C$\underline{H}_2$—), 7.37-7.94 (5H, m, $\underline{\text{arom.H}}$)

(13)

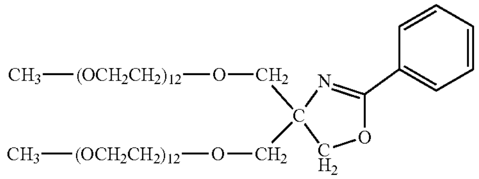

Example 4 Synthesis of Compound 14

A compound of the formula (13) (1.13 g, 0.877/mmol) and distilled water (31.1 g) were added to a 100 mL three-necked flask equipped with a thermometer, a nitrogen inlet tube, a stirrer, a Dean-stark tube, and a cooling tube and dissolved therein. 85% Phosphoric acid (0.43 ml) was added to adjust the pH to 1.5, and a reaction was performed at 50° C. for 3 hr. Then, 400 g/L aqueous sodium hydroxide solution (5.58 ml) was added while cooling, and a reaction was performed at 50° C. for 6 hr. Successively, 6N hydrochloric acid was added to adjust the pH to 2.0, and the mixture was washed with toluene and chloroform. Sodium chloride was added to the aqueous layer to make 25 wt % brine, and the pH was adjusted to 12.5 with 400 g/L aqueous sodium hydroxide solution. The mixture was extracted with toluene, dried over anhydrous sodium sulfate, and filtered. The solvent was evaporated under reduced pressure to give a compound of the formula (14).

$^1$H-NMR ($CDCl_3$, internal standard TMS); δ(ppm): 3.08 (1H, brs, —OH), 3.38 (6H, s, —O—$CH_3$), 3.40-3.80 (102H, m, >C($CH_2$O)$_2$—, —O—($CH_2CH_2$O)$_{12}$—, >$CNH_2$—$CH_2$—OH)

(14)

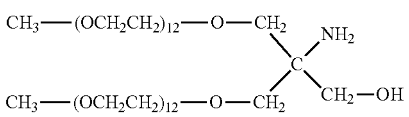

Example 5 Synthesis of Compound 15

A compound of the formula (14) (1.80 g, 1.49 mmol), L-phenylalanine-glycine with N terminal protected by a 9-fluorenylmethyloxycarbonyl group (Fmoc group) (Fmoc-Phe-Gly) (0.862 g, 1.94 mmol, manufactured by WATANABE CHEMICAL INDUSTRIES, LTD.), 4-(4,6-dimethoxy-1,3,5-triazin-2-yl)-4-methylmorpholinium chloride (DMT-MM) (0.670 g, 1.94 mmol), acetonitrile (18.0 g), and N,N-diisopropylethylamine (0.263 g, 2.04 mmol) were charged in a 50 mL three-necked flask equipped with a thermometer, a nitrogen inlet tube, a stirrer, a Dean-stark tube, and a cooling tube, and reacted at 25° C. for 7 hr. A 5 wt % aqueous sodium dihydrogen phosphate solution (10.8 g) was added, acetonitrile was evaporated under reduced pressure, and the aqueous layer was washed with toluene and hexane. The aqueous layer was extracted with toluene and chloroform, and the extract was washed with water using 5 wt % aqueous sodium dihydrogen phosphate solution and 20 wt % sodium chloride-containing 5 wt % aqueous disodium hydrogen phosphate solution. The organic layer was washed with 20 wt % brine, dried over anhydrous magnesium sulfate, and filtered. The solvent was evaporated under reduced pressure to give a compound of the formula (15).

$^1$H-NMR ($CD_2Cl_2$, internal standard TMS); δ(ppm): 2.99-3.26 (2H, m, —CH—$CH_2$-phenyl), 3.38 (6H, s, —O—$CH_3$), 3.45-3.90 (104H, m, >C($CH_2$O)$_2$—, —O—($CH_2CH_2$O)$_{12}$—, —CH—$CH_2$-phenyl, >$CCH_2$—NHCO—$CH_2$—NHCO—CH—, —NH—C(O)O—$CH_2$-Fmoc(1H)) 3.94-4.46 (6H, m, >CNH—$CH_2$—OH, >$CCH_2$—NHCO—$CH_2$—NHCO—CH—, >CNH—$CH_2$—OH, —NH—C(O)O—$CH_2$-Fmoc (1H), —NH—C(O)O—$CH_2$—Fmoc(CH)), 5.63 (1H, d, —NH—C(O)O—$CH_2$-Fmoc), 6.74 (1H, brs, >$CCH_2$—NHCO—$CH_2$—), 7.09-7.76 (13H, m, arom.H)

(15)

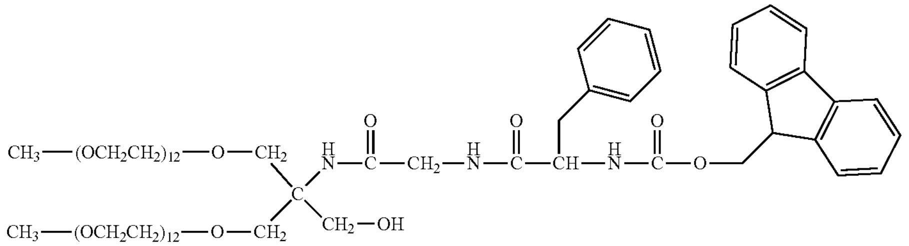

Example 6 Synthesis of Compound 16

A compound of the formula (15) (1.80 g, 1.10 mmol), N-phenylmorpholine (0.449 g, 3.85 mmol), p-nitrophenyl chloroformate (0.621 g, 3.08 mmol), and dichloromethane (17.9 g) were added to a 20 mL screw tube with a stirrer, and reacted at 25° C. for 2 hr. Furthermore, the mixture was diluted with 6.7 wt % aqueous β alanine solution (11.8 g), and dichloromethane was evaporated under reduced pressure. A 400 g/L aqueous sodium hydroxide solution (0.869 g, 6.60 mmol) was added, and the mixture was reacted at 25° C. for 1 hr. The reaction mixture was washed with toluene and dichloromethane, sodium chloride was dissolved in the aqueous layer to give 15 wt % brine and extracted with dichloromethane. Acetonitrile was added to the organic layer, and the mixture was washed with water using 15 wt % sodium chloride-containing 5 wt % aqueous sodium carbonate solution and further washed with water using 20 wt % sodium chloride-containing 0.2M hydrochloric acid. The organic layer was dried over anhydrous sodium sulfate, and filtered. The solvent was evaporated under reduced pressure to give a compound of the formula (16).

$^1$H-NMR ($CDCl_3$, internal standard TMS); δ(ppm): 2.47-2.52 (2H, m, >CNH—$CH_2$—OC(O)—NH—$CH_2$—$CH_2$—COOH), 2.95-3.24 (2H, m, —CH—$CH_2$-phenyl), 3.38 (6H, s, —O—$CH_3$), 3.45-3.90 (106H, m, >C($CH_2$O)$_2$—, —O—($CH_2CH_2$O)$_{12}$—, —CH—$CH_2$-phenyl, >$CCH_2$—NHCO—$CH_2$—NHCO—CH—, —NH—C(O)O—$CH_2$-Fmoc (1H), >CNH—$CH_2$—OC(O)—NH—$CH_2$—$CH_2$—COOH), 3.94-4.55 (5H, m, >CNH—$CH_2$—OC(O)—NH—, —NH—C(O)O—$CH_2$—Fmoc(CH), >$CCH_2$—NHCO—$CH_2$—NHCO—CH—, —NH—C(O)O—$CH_2$-Fmoc(1H)), 5.72 (1H, brs, >CNH—$CH_2$—OC(O)—NH—$CH_2$—$CH_2$—COOH), 5.81 (1H, d, —NH—C(O)O—$CH_2$-Fmoc), 6.71 (1H, brs, >$CCH_2$—NHCO—$CH_2$—), 7.10-7.80 (13H, m, arom.H)

(16)

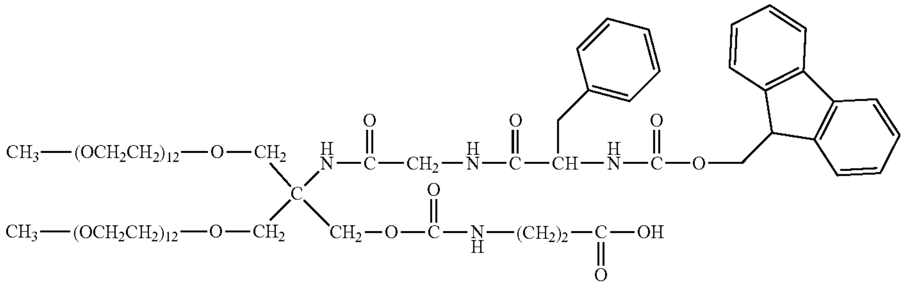

Example 7 Synthesis of Compound 17

A compound of the formula (16) (0.935 g, 0.535 mmol), piperidine (0.846 g, 10.7 mmol), and chloroform (6.55 g) were added to a 50 mL screw tube with a stirrer, and reacted at 25° C. for 2 hr. The reaction mixture was washed with water using 20 wt % sodium chloride-containing 0.2M hydrochloric acid, the organic layer was diluted with toluene, and extracted with distilled water into the aqueous layer. The aqueous layer adjusted to pH 10 with 400 g/L aqueous sodium hydroxide solution was washed with toluene, and the aqueous layer was adjusted to pH 2.5 with 6N hydrochloric acid. Sodium chloride was dissolved in the aqueous layer to give 15 wt % brine, followed by extraction with chloroform. The organic layer was dried over anhydrous sodium sulfate, and filtered. The solvent was evaporated under reduced pressure to give a compound of the formula (17).

$^1$H-NMR ($CDCl_3$, internal standard TMS); δ(ppm): 2.58 (2H, m, >CNH—$CH_2$—OC(O)—NH—$CH_2$—$\underline{CH_2}$—COOH), 3.15-3.30 (1H, m, —NHCO—$\underline{CH}$—$NH_2$), 3.38 (6H, s, —O—$\underline{CH_3}$), 3.45-3.90 (106H, m, >C($\underline{CH_2}$O)$_2$—, —O—($\underline{CH_2}\underline{CH_2}$O)$_{12}$—, —CH—$\underline{CH_2}$-phenyl, >$CCH_2$—NHCO—$\underline{CH_2}$—NHCO—CH—, —OC(O)—NH—$\underline{CH_2}$—$CH_2$—COOH), 4.20-4.50 (2H, m, >CNH—$\underline{CH_2}$—OC(O)—NH—), 4.59 (1H, s, >$CCH_2$—NHCO—$CH_2$—N$\underline{H}$CO—CH—$NH_2$), 6.18 (1H, brs, —OC(O)—N$\underline{H}$—$CH_2$—$CH_2$—COOH), 6.65 (1H, brs, >$CCH_2$—N$\underline{H}$CO—$CH_2$—), 7.20-7.50 (5H, m, $\underline{\text{arom.H}}$), 8.77 (2H, s, —CH—N$\underline{H_2}$)

Example 8 Synthesis of Compound 18

A compound of the formula (17) (0.703 g, 0.450 mmol), N-succinimidyl 4-(N-maleimidomethyl)cyclohexane-1-carboxylate (0.181 g, 0.540 mmol), triethylamine (0.105 g, 1.04 mmol), 2,6-di-tert-butyl-p-cresol (0.21 mg), and chloroform (13.4 g) were added to a 30 mL screw tube with a stirrer, and reacted at 25° C. for 13 hr under shading. The reaction mixture was washed with water using 20 wt % sodium chloride-containing 0.2 M citrate phosphate buffer (pH 2.4). The organic layer was concentrated, and the residue was dissolved in 0.2 M citrate phosphate buffer (pH 3.0). The aqueous layer was washed with toluene, and extracted with toluene and chloroform into the organic layer. The organic layer was washed with water with 20 wt % brine, dried over anhydrous magnesium sulfate, and filtered. The solvent was evaporated under reduced pressure to give a compound of the formula (18).

$^1$H-NMR ($CDCl_3$, internal standard TMS); δ(ppm): 0.89-2.09 (10H, m, -$\underline{\text{cyclohexyl}}$-), 2.54 (2H, brs, —OC(O)—NH—$CH_2$—$\underline{CH_2}$—COOH), 2.93-3.20 (2H, m, -cyclohexyl-$\underline{CH_2}$-maleimide), 3.38 (6H, s, —O—$\underline{CH_3}$), 3.33-3.95 (106H, m, >C($\underline{CH_2}$O)$_2$—, —O—($\underline{CH_2}\underline{CH_2}$O)$_{12}$—, —CH—$\underline{CH_2}$-phenyl, >$CCH_2$—NHCO—$\underline{CH_2}$—NHCO—CH—, —OC(O)—NH—$\underline{CH_2}$—$CH_2$—COOH), 4.28-4.45 (2H, m, >CNH—$\underline{CH_2}$—OC(O)—NH—), 4.74-4.80 (1H, m, —NHCO—$\underline{CH}$—NHCO-cyclohexyl-), 5.63 (1H, brs, —OC(O)—N$\underline{H}$—$CH_2$—$CH_2$—COOH), 6.26 (1H, d, >$CCH_2$—NHCO—$CH_2$—N$\underline{H}$CO—CH—), 6.64 (1H, brs, >$CCH_2$—N$\underline{H}$CO—$CH_2$—), 6.69 (2H, s, -$\underline{\text{maleimide}}$), 7.07 (1H, brs, —N$\underline{H}$CO-cyclohexyl-), 7.16-7.26 (5H, m, $\underline{\text{arom.H}}$)

(17)

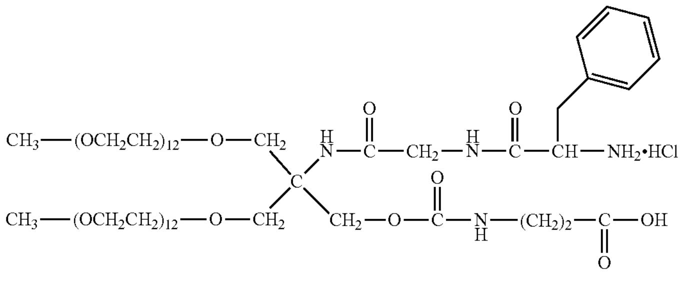

(18)

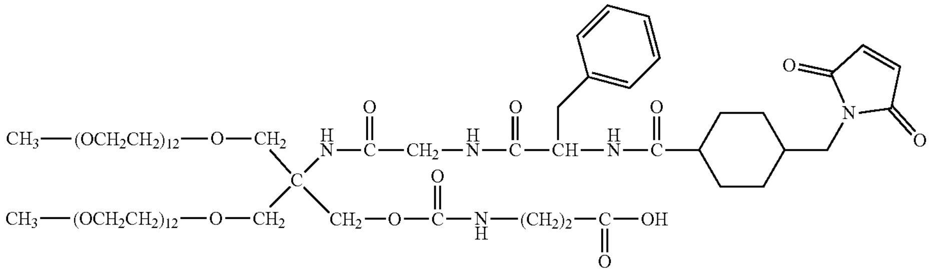

Example 9 Synthesis of Compound 19

A compound of the formula (18) (0.351 g, 0.201 mmol), N-hydroxysuccinimide (0.058 g, 0.503 mmol), dimethylaminopropylethylcarbodiimide hydrochloride (0.123 g, 0.643 mmol), and chloroform (2.08 g) were added to a 4 ml screw tube with a stirrer, and reacted at 25° C. for 4 hr under shading. The reaction mixture was washed with water using 5 wt % aqueous sodium dihydrogen phosphate solution, dried over anhydrous magnesium sulfate, and filtered. The solvent was evaporated under reduced pressure to give a compound of the formula (19).

$^1$H-NMR ($CDCl_3$, internal standard TMS); δ(ppm): 0.89-2.01 (10H, m, -cyclohexyl-), 2.81-2.90 (6H, m, >CNH—$CH_2$—OC(O)—NH—$CH_2$—$CH_2$—COO—, —N-succinimidyl), 2.90-3.25 (2H, m, -cyclohexyl-$CH_2$-maleimide), 3.38 (6H, s, —O—$CH_3$), 3.33-3.95 (106H, m, >C($CH_2$O)$_2$—, —O—($CH_2CH_2O$)$_{12}$—, —CH—$CH_2$-phenyl, >$CCH_2$—NHCO—$CH_2$—NHCO—, —OC(O)—NH—$CH_2$—$CH_2$—COO—), 4.28-4.45 (2H, m, >CNH—$CH_2$—OC(O)—NH—), 4.65-4.70 (1H, m, —NHCO—CH—NHCO-cyclohexyl-), 5.84 (1H, brs, —OC(O)—NH—$CH_2$—$CH_2$—COOH), 6.16 (1H, d, >$CCH_2$—NHCO—$CH_2$—NHCO—CH—), 6.55 (1H, brs, >$CCH_2$—NHCO—$CH_2$—), 6.69 (2H, s, -maleimide), 6.91 (1H, brs, —NHCO-cyclohexyl-), 7.15-7.28 (5H, m, arom.H)

(19)

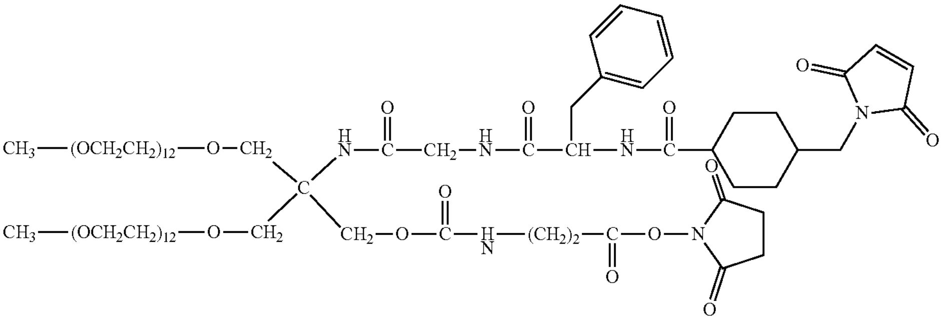

Example 10 Reaction of Compound 18 with Glutathione

A compound of the formula (18) (1 mg), and aqueous 10 mM glutathione/25 mM sodium acetate/1 mM disodium ethylenediaminetetraacetate dihydrate (EDTA) solution (1 ml) adjusted to pH 5 with acetic acid were charged in a 4 ml screw tube with a stirrer, and reacted at 25° C. for 3 hr under shading to give an aqueous solution containing a compound of the formula (20).

(20)

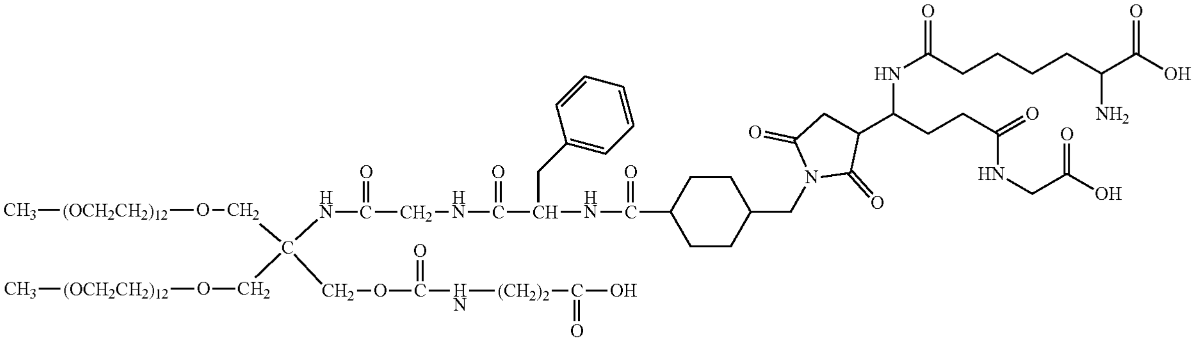

Example 11 Synthesis of Compound 21

A compound of the formula (14) (0.350 g, 0.290 mmol), L-valine-L-alanine-glycine with N terminal protected by a 9-fluorenylmethyloxycarbonyl group (Fmoc group) (Fmoc-Val-Ala-Gly) (0.154 g, 0.363 mmol, manufactured by GenScript), DMT-MM (0.130 g, 0.508 mmol), acetonitrile (3.50 g), and N,N-diisopropylethylamine (0.073 g, 0.566 mmol) were charged in a 30 ml screw tube with a stirrer, and reacted at 25° C. for 13 hr. A 5 wt % aqueous sodium dihydrogen phosphate solution (4.20 g) was added, acetonitrile was evaporated under reduced pressure, and the aqueous layer was washed with toluene and hexane. After extraction with toluene and chloroform, washing with water was performed using 5 wt % aqueous sodium dihydrogen phosphate solution, and 5 wt % aqueous disodium hydrogen phosphate solution. The organic layer was washed with 20 wt % brine, dried over anhydrous magnesium sulfate, and filtered. The solvent was evaporated under reduced pressure to give a compound of the formula (21).

$^1$H-NMR (DMSO-d6, internal standard TMS); δ(ppm): 0.78-0.93 (6H, m, >CH—CH($\underline{CH_3}$)$_2$), 1.22 (3H, d, >CH—$\underline{CH_3}$), 1.93-2.04 (1H, m, >CH—$\underline{CH}$($CH_3$)$_2$), 3.24 (6H, s, —O—$\underline{CH_3}$), 3.38-3.76 (102H, m, >C($\underline{CH_2}$O)$_2$—, —O—($\underline{CH_2}\underline{CH_2}$O)$_{12}$—, >CNHCO—$\underline{CH_2}$—NHCO—), 3.83-3.94 (1H, m, —$CH_2$—$\underline{Fmoc(CH)}$), 4.16-4.42 (6H, m, >$\underline{CH}$—$CH_3$, >$\underline{CH}$—CH($CH_3$)$_2$, —$\underline{CH_2}$-Fmoc, >CNH—$\underline{CH_2}$—OH), 4.66 (1H, t, >CNH—$CH_2$—$\underline{OH}$), 7.09 (1H, s, —$\underline{NH}$—C(O)O—$CH_2$-Fmoc), 7.28-7.43 (5H, m, $\underline{arom.H}$, >CN$\underline{H}$CO—$CH_2$—NHCO—), 7.70-7.92 (4H, m, $\underline{arom.H}$), 8.00-8.11 (2H, m, —N$\underline{H}$CO—CH—NHCO—CH—, —NHCO—CH—N$\underline{H}$CO—CH—)

(21)

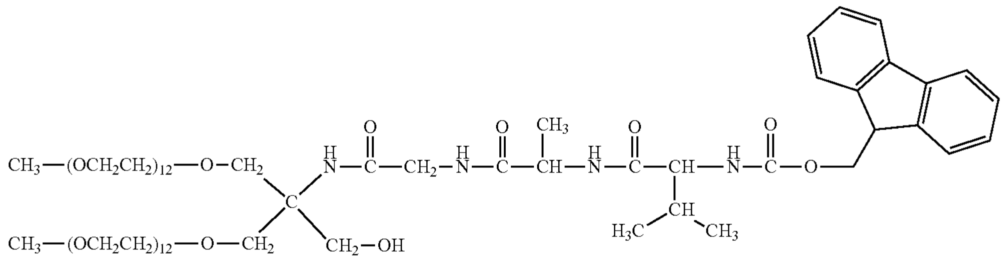

Example 12 Synthesis of Compound 22

A compound of the formula (21) (0.306 g, 0.185 mmol), N-phenylmorpholine (0.106 g, 0.648 mmol), p-nitrophenyl chloroformate (0.104 g, 0.518 mmol), and dichloromethane (2.40 g) were added to a 6 mL screw tube with a stirrer, and reacted at 25° C. for 9 hr. The mixture was diluted with 6.7 wt % aqueous β alanine solution (2.00 g), and dichloromethane was evaporated under reduced pressure. A 400 g/L aqueous sodium hydroxide solution (0.150 g, 1.11 mmol) was added, and the mixture was reacted at 25° C. for 1 hr. The reaction mixture was washed with toluene and dichloromethane, and extracted with dichloromethane. After washing with water using 15 wt % sodium chloride-containing 5 wt % aqueous sodium carbonate solution, the reaction mixture was washed with water using 20 wt % sodium chloride-containing 0.2 M hydrochloric acid. The organic layer was dried over anhydrous sodium sulfate, and filtered. The solvent was evaporated under reduced pressure to give a compound of the formula (22).

$^1$H-NMR (DMSO-d6, internal standard TMS); δ(ppm): 0.78-0.92 (6H, m, >CH—CH($\underline{CH_3}$)$_2$), 1.22 (3H, d, >CH—$\underline{CH_3}$), 1.92-2.03 (1H, m, >CH—$\underline{CH}$($CH_3$)$_2$), 2.38 (2H, t, >C$CH_2$—OC(O)—NH—$CH_2$—$\underline{CH_2}$—COOH), 3.12-3.21 (2H, m, >C$CH_2$—OC(O)—NH—$\underline{CH_2}$—$CH_2$—COOH), 3.24 (6H, s, —O—$\underline{CH_3}$), 3.38-3.78 (102H, m, >C($\underline{CH_2}$O)$_2$—, —O—($\underline{CH_2}\underline{CH_2}$O)$_{12}$—, >CNHCO—$\underline{CH_2}$—NHCO—), 3.88 (1H, t, —$CH_2$—$\underline{Fmoc(CH)}$), 4.12-4.40 (6H, m, >$\underline{CH}$—$CH_3$, >$\underline{CH}$—CH($CH_3$)$_2$, —$\underline{CH_2}$-Fmoc, >C$\underline{CH_2}$—OC(O)—NH—), 7.09-7.28 (2H, m, —$\underline{NH}$—C(O)O—$CH_2$-Fmoc, >C$CH_2$—OC(O)—N$\underline{H}$—), 7.29-7.45 (5H, m, $\underline{arom.H}$, >CN$\underline{H}$CO—$CH_2$—NHCO—), 7.70-7.94 (4H, m, $\underline{arom.H}$), 7.96-8.10 (2H, m, —N$\underline{H}$CO—CH—NHCO—CH—, —NHCO—CH—N$\underline{H}$CO—CH—)

(22)

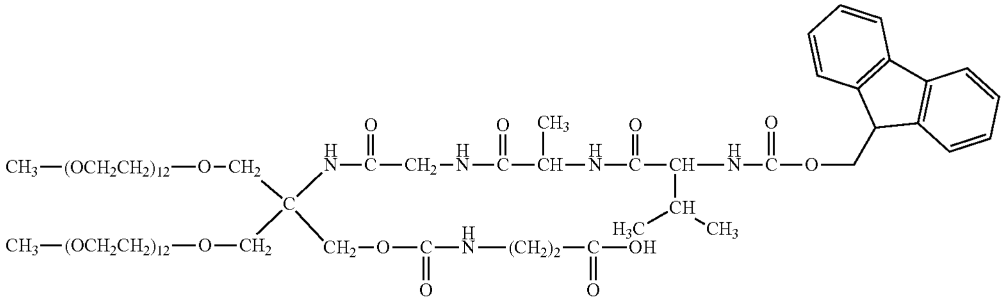

Example 13 Synthesis of Compound 23

A compound of the formula (22) (0.177 g, 0.100 mmol), piperidine (0.158 g, 2.00 mmol), and chloroform (2.50 g) were added to a 9 mL screw tube with a stirrer, and reacted at 25° C. for 2 hr. The reaction mixture was washed with water using 20 wt % sodium chloride-containing 0.2 M hydrochloric acid, the organic layer was diluted with toluene and extracted with distilled water into an aqueous layer. An aqueous layer adjusted to pH 10 with 400 g/L aqueous sodium hydroxide solution was washed with toluene and chloroform, and adjusted to pH 2.5 with 6N hydrochloric acid. Sodium chloride was dissolved in the aqueous layer to give 10 wt % brine and the aqueous layer was extracted with chloroform. The organic layer was dried over anhydrous sodium sulfate, and filtered. The solvent was evaporated under reduced pressure to give a compound of the formula (23).

$^1$H-NMR (DMSO-d6, internal standard TMS); δ(ppm): 0.71-0.92 (6H, m, >CH—CH($CH_3$)$_2$), 1.13-1.31 (3H, d, >CH—$CH_3$), 1.82-2.04 (3H, m, >CH—CH($CH_3$)$_2$, >$CCH_2$—OC(O)—NH—$CH_2$—$CH_2$—COOH), 2.87-3.13 (3H, m, >$CCH_2$—OC(O)—NH—$CH_2$—$CH_2$—COOH, >CH—CH($CH_3$)$_2$), 3.24 (6H, s, —O—$CH_3$), 3.40-3.85 (102H, m, >C($CH_2$O)$_2$—, —O—($CH_2CH_2$O)$_{12}$—, >CNHCO—$CH_2$—NHCO—), 4.03-4.42 (3H, m, >CH—$CH_3$, >$CCH_2$—OC(O)—NH—), 6.64 (1H, brs, >$CCH_2$—OC(O)—NH—), 6.95-7.32 (3H, m, >CNHCO—$CH_2$—NHCO—, —NHCO—CH—NHCO—CH—, —NHCO—CH—NHCO—CH—)

Example 14 Synthesis of Compound 24

A compound of the formula (23) (0.100 g, 0.0637 mmol), N-succinimidyl 4-(N-maleimidomethyl)cyclohexane-1-carboxylate (0.0788 g, 0.236 mmol), triethylamine (8.4 mg, 0.0828 mmol), 2,6-di-tert-butyl-p-cresol (0.03 mg), and chloroform (1.90 g) were added to a 9 mL screw tube with a stirrer, and reacted at 25° C. for 17 hr under shading. The reaction mixture was washed with water using 20 wt % sodium chloride-containing 0.2M citrate phosphate buffer (pH 2.4), the organic layer was concentrated, and the residue was dissolved in 0.2M citrate phosphate buffer (pH 3.0). The aqueous layer was washed with toluene and chloroform and extracted into an organic layer by using toluene and chloroform. The organic layer was washed with water using 20 wt % brine, dried over anhydrous magnesium sulfate, and filtered. The solvent was evaporated under reduced pressure to give a compound of the formula (24).

$^1$H-NMR ($CD_2Cl_2$, internal standard TMS); δ(ppm): 0.81-1.12 (8H, m, >CH—CH($CH_3$)$_2$, -cyclohexyl-), 1.31-1.48 (5H, d, >CH—$CH_3$, -cyclohexyl-), 1.71-2.18 (7H, m, >CH—CH($CH_3$)$_2$, -cyclohexyl-), 2.48-2.63 (2H, m, >$CCH_2$—OC(O)—NH—$CH_2$—$CH_2$—COOH), 3.34 (6H, s, —O—$CH_3$), 3.38-3.95 (106H, m, >C($CH_2$O)$_2$—, —O—($CH_2CH_2$O)$_{12}$—, >CNHCO—$CH_2$—NHCO—, >$CCH_2$—OC(O)—NH—$CH_2$—$CH_2$—COOH, -cyclohexyl-$CH_2$-maleimide), 4.16-4.38 (2H, m, >CH—$CH_3$, >CH—CH($CH_3$)$_2$), 4.42-4.52 (2H, m, >$CCH_2$—OC(O)—NH—), 6.17-6.32 (2H, m, >CNHCO—$CH_2$—NHCO—, >$CCH_2$—OC(O)—NH—), 6.50 (1H, brs, >CNHCO—$CH_2$—NHCO—CH—), 6.68 (2H, s, -maleimide), 7.20-7.43 (2H, m, >CNHCO—$CH_2$—NHCO—CH—NHCO—CH—, —NHCO-cyclohexyl-)

(23)

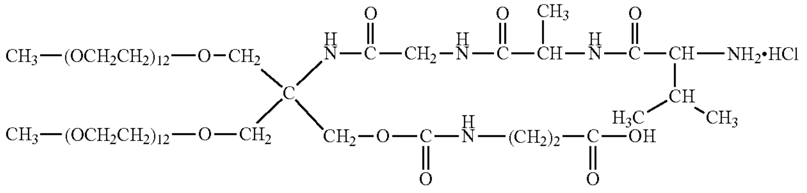

(24)

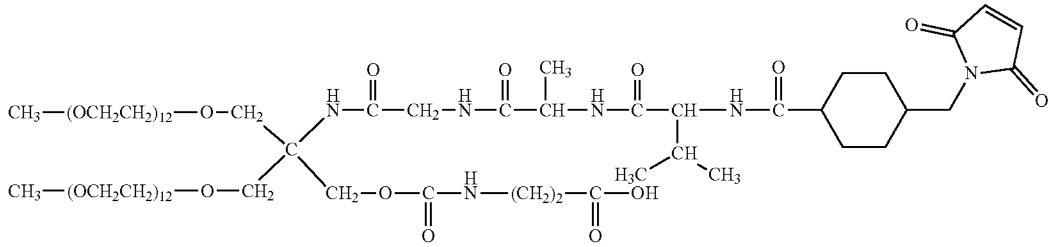

Example 15 Synthesis of Compound 25

A compound of the formula (24) (0.100 g, 0.0566 mmol), N-hydroxysuccinimide (9.8 mg, 0.0849 mmol), dimethylaminopropylethylcarbodiimide hydrochloride (0.0228 g, 0.119 mmol), and chloroform (0.800 g) were added to a 4 ml screw tube with a stirrer, and reacted at 25° C. for 4 hr under shading. The reaction mixture was washed with water using 5 wt % aqueous sodium dihydrogen phosphate solution, dried over anhydrous magnesium sulfate, and filtered. The solvent was evaporated under reduced pressure to give a compound of the formula (25).

$^1$H-NMR (DMSO-d6, internal standard TMS); δ(ppm): 0.75-0.97 (8H, m, >CH—CH(C$H_3$)$_2$, -cyclohexyl-), 1.17-1.33 (5H, d, >CH—C$H_3$, -cyclohexyl-), 1.48-1.75 (5H, m, -cyclohexyl-), 1.93-2.02 (1H, m, >CH—CH(CH$_3$)$_2$), 2.17-2.27 (1H, m, -cyclohexyl-), 2.81 (4H, s, —N-succinimidyl), 2.83-2.88 (2H, m, >CCH$_2$—OC(O)—NH—CH$_2$—CH$_2$—), 3.23 (6H, s, —O—CH$_3$), 3.42-3.75 (106H, m, >C(CH$_2$O)$_2$—, —O—(CH$_2$CH$_2$O)$_{12}$—, >CNHCO—CH$_2$—NHCO—, >CCH$_2$—OC(O)—NH—CH$_2$—CH$_2$—, -cyclohexyl-CH$_2$-maleimide), 4.08-4.33 (4H, m, >CH—CH$_3$, >CH—CH(CH$_3$)$_2$, >CCH$_2$—OC(O)—NH—), 7.01 (2H, s, -maleimide), 7.26-7.35 (2H, m, >CNHCO—CH$_2$—NHCO—, >CCH$_2$—OC(O)—NH—), 7.62-7.72 (1H, m, —NHCO-cyclohexyl-), 7.90-8.05 (2H, m, >CNHCO—CH$_2$—NHCO—CH—, >CNHCO—CH$_2$—NHCO—CH—NHCO—CH—)

Example 16 Synthesis of Compound 26

A compound of the formula (14) (2.00 g, 1.66 mmol), Fmoc-β alanine (0.568 g, 1.82 mmol), DMT-MM (0.631 g, 1.82 mmol), acetonitrile (18.0 g), and N,N-diisopropylethylamine (0.279 g, 2.16 mmol) were charged in a 50 ml screw tube with a stirrer, and reacted at 25° C. for 2 hr. A 5 wt % aqueous sodium dihydrogen phosphate solution (12.0 g) was added, acetonitrile was evaporated under reduced pressure, and the aqueous layer was washed with toluene. Thereafter, purification similar to that in Example 5 was performed to give a compound of the formula (26).

$^1$H-NMR (CDCl$_3$, internal standard TMS); δ(ppm): 2.99-3.26 (2H, m, >CCH$_2$—NHCO—CH$_2$—CH$_2$—NHCO—), 3.38 (6H, s, —O—CH$_3$), 3.45-3.90 (104H, m, >C(CH$_2$O)$_2$—, —O—(CH$_2$CH$_2$O)$_{12}$—, >CNH—CH$_2$—OH, >CCH$_2$—NHCO—CH$_2$—CH$_2$—NHCO—), 4.18-4.22 (1H, m, >CNH—CH$_2$—OH), 4.34 (1H, t, —NH—C(O)O—CH$_2$—Fmoc(CH)), 4.40 (2H, d, —NH—C(O)O—CH$_2$-Fmoc), 5.75-5.80 (1H, m, —NH—C(O)O—CH$_2$-Fmoc), 6.34 (1H, brs, >CCH$_2$—NHCO—CH$_2$—), 7.28-7.78 (8H, m, arom.H)

(25)

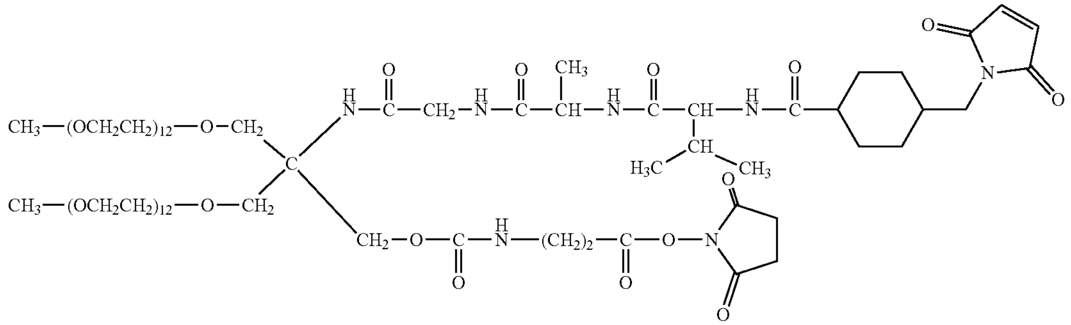

(26)

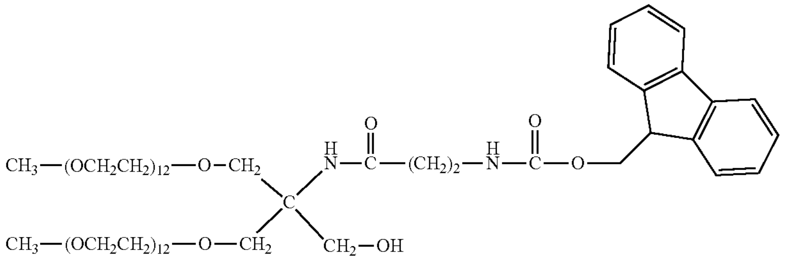

Example 17 Synthesis of Compound 27

A compound of the formula (26) (2.00 g, 1.33 mmol), N-phenylmorpholine (0.762 g, 4.00 mmol), p-nitrophenyl chloroformate (0.753 g, 3.20 mmol), and dichloromethane (19.3 g) were added to a 20 mL screw tube with a stirrer, and reacted at 25° C. for 6 hr. Further, the mixture was diluted with 6.7 wt % aqueous β alanine solution (14.3 g), dichloromethane was evaporated under reduced pressure, and the mixture was reacted at 25° C. for 1 hr. The reaction mixture was washed with toluene and dichloromethane, sodium chloride was dissolved in the aqueous layer to give 15 wt % brine and the aqueous layer was extracted with dichloromethane. Acetonitrile was added to the organic layer, and the mixture was washed with water using 15 wt % sodium chloride-containing 5 wt % aqueous sodium carbonate solution, and further washed with water using 20 wt % sodium chloride-containing 0.2 M hydrochloric acid. The organic layer was dried over anhydrous sodium sulfate, and filtered. The solvent was evaporated under reduced pressure to give a compound of the formula (27).

$^1$H-NMR ($CDCl_3$, internal standard TMS); δ(ppm): 2.38 (2H, brs, —OC(O)—NH—$CH_2$—$\underline{CH_2}$—COOH), 2.51 (2H, t, >$CCH_2$—NHCO—$\underline{CH_2}$—$CH_2$—), 3.38 (6H, s, —O—$\underline{CH_3}$), 3.40-3.90 (104H, m, >C($\underline{CH_2}$O)$_2$—, —O—($\underline{CH_2CH_2}$O)$_{12}$—, >$CCH_2$—NHCO—$CH_2$—$\underline{CH_2}$—NHCO—, —OC(O)—NH—$\underline{CH_2}$—$CH_2$—COOH), 4.19-4.23 (1H, m, —NH—C(O)O—$CH_2$—$\underline{\text{Fmoc(CH)}}$), 4.45-4.50 (4H, m, >CNH—$\underline{CH_2}$—OC(O)—NH—, —NH—C(O)O—$\underline{CH_2}$-Fmoc), 5.56 (1H, brs, >CNH—$CH_2$—OC(O)—$\underline{\text{NH}}$—), 5.93 (1H, brs, —$\underline{\text{NH}}$—C(O)O—$CH_2$-Fmoc), 6.33 (1H, brs, >$CCH_2$—N$\underline{\text{H}}$CO—$CH_2$—), 7.26-7.78 (8H, m, $\underline{\text{arom.H}}$)

Example 18 Synthesis of Compound 28

A compound of the formula (27) (0.500 g, 0.310 mmol), L-phenylalanine-glycine hydrochloride with C-terminal condensed with p-aminobenzyl alcohol (pAB) (H-Phe-Gly-pAB hydrochloride) (0.141 g, 0.387 mmol, manufactured by WATANABE CHEMICAL INDUSTRIES, LTD.), DMT-MM (0.134 g, 0.387 mmol), acetonitrile (5.00 g), and N,N-diisopropylethylamine (0.092 g, 0.712 mmol) were charged in a 20 mL screw tube with a stirrer, and reacted at 25° C. for 3 hr. A 5 wt % aqueous sodium dihydrogen phosphate solution (3.00 g) was added, acetonitrile was evaporated under reduced pressure, and the aqueous layer was washed with toluene and hexane. Thereafter, purification similar to that in Example 5 was performed to give a compound of the formula (28).

$^1$H-NMR ($CDCl_3$, internal standard TMS); δ(ppm): 2.20-2.45 (4H, m, >$CCH_2$—NHCO—$\underline{CH_2}$—$CH_2$—, —OC(O)—NH—$CH_2$—$\underline{CH_2}$—), 3.38 (6H, s, —O—$\underline{CH_3}$), 2.60-3.80 (108H, m, >C($\underline{CH_2}$O)$_2$—, —O—($\underline{CH_2CH_2}$O)$_{12}$—, —CH—$\underline{CH_2}$-phenyl, CNH—$CH_2$—OC(O)—NH—$\underline{CH_2}$—$CH_2$—, >$CCH_2$—NHCO—$CH_2$—$\underline{CH_2}$—NHCO—, —CONH—$\underline{CH_2}$—CONH-phenyl-$CH_2$—OH), 3.80-4.57 (9H, —NH—C(O)O—$\underline{CH_2}$-Fmoc, —CONH—phenyl-$\underline{CH_2}$—OH, —$CH_2$—$\underline{\text{Fmoc(CH)}}$, —($CH_2$)$_2$—CON$\underline{\text{H}}$—CH—CONH—$CH_2$—, —$CH_2$—O$\underline{\text{H}}$, —($CH_2$)$_2$—CON$\underline{\text{H}}$—CH—CONH—$CH_2$—, —($CH_2$)$_2$—CONH—C$\underline{\text{H}}$—CONH—$CH_2$—), 4.61 (2H, >CNH—$\underline{CH_2}$—OC(O)—NH—), 6.02-6.15 (2H, m, —N$\underline{\text{H}}$—C(O)O—$CH_2$-Fmoc, >CNH—$CH_2$—OC(O)—N$\underline{\text{H}}$—), 6.53 (1H, brs, >$CCH_2$—N$\underline{\text{H}}$CO—$CH_2$—$CH_2$—), 7.11-7.84 (17H, m, $\underline{\text{arom.H}}$), 8.89 (1H, brs, —CON$\underline{\text{H}}$-phenyl-$CH_2$—OH)

(27)

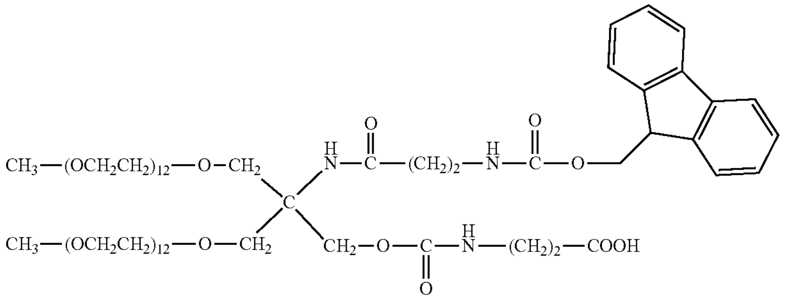

(28)

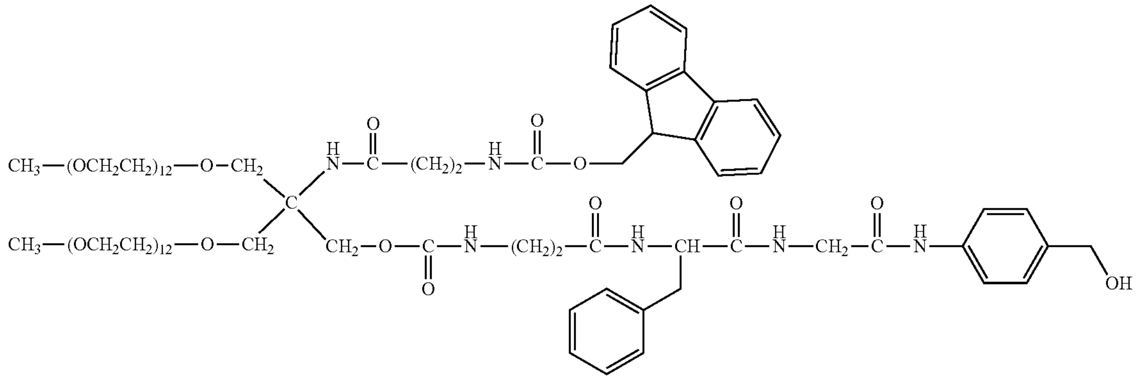

Example 19 Synthesis of Compound 29

A compound of the formula (28) (0.100 g, 0.052 mmol), piperidine (0.082 g, 1.04 mmol), and chloroform (0.700 g) were added to a 6 mL screw tube with a stirrer, and reacted at 25° C. for 2 hr. The reaction mixture was washed with water using 20 wt % sodium chloride-containing 0.2 M hydrochloric acid, the organic layer was diluted with toluene, and extracted with distilled water into an aqueous layer. The aqueous layer adjusted to pH 10 with 400 g/L aqueous sodium hydroxide solution was washed with toluene, and adjusted to pH 2.5 with 6N hydrochloric acid. Sodium chloride was dissolved in the aqueous layer to give 15 wt % brine and the aqueous layer was extracted with chloroform. The organic layer was dried over anhydrous sodium sulfate, and filtered. The solvent was evaporated under reduced pressure to give a compound of the formula (29).

$^1$H-NMR ($CDCl_3$, internal standard TMS); δ(ppm): 2.20-2.55 (6H, m, >$CCH_2$—NHCO—$CH_2$—, —OC(O)—NH—$CH_2$—$CH_2$—, —$CH_2$—$NH_2$), 3.38 (6H, s, —O—$CH_3$), 2.90-3.80 (106H, m, >C($CH_2$O)$_2$—, —O—($CH_2CH_2$O)$_{12}$—, —CH—$CH_2$-phenyl, >CNH—$CH_2$—OC(O)—NH—$CH_2$—$CH_2$—, —CONH—$CH_2$—CONH-phenyl-$CH_2$—OH), 3.80-4.57 (6H, —CONH-phenyl-$CH_2$—OH, —($CH_2$)$_2$—CONH—CH—CONH—$CH_2$—, —($CH_2$)$_2$—CONH—CH—CONH—$CH_2$—, —($CH_2$)$_2$—CONH—CH—CONH—$CH_2$—, —$CH_2$—OH), 4.61 (2H, >CNH—$CH_2$—OC(O)—NH—), 6.01 (1H, brs, >CNH—$CH_2$—OC(O)—NH—), 6.53 (1H, brs, >$CCH_2$—NHCO—$CH_2$—$CH_2$—), 7.20-7.80 (9H, m, arom.H), 8.70 (2H, brs, —$CH_2$—$NH_2$), 8.87 (1H, brs, —CONH-phenyl-$CH_2$—OH)

Example 20 Synthesis of Compound 30

A compound of the formula (29) (0.100 g, 0.058 mmol), 3-maleimidopropionic acid (0.012 g, 0.072 mmol), DMT-MM (0.020 g, 0.072 mmol), triethylamine (0.013 g, 0.132 mmol), and acetonitrile (1.00 g) were added to a 6 ml screw tube with a stirrer, and reacted at 25° C. for 2 hr under shading. 0.2 M Citrate phosphate buffer (pH3.0) (0.600 g) was added, acetonitrile was evaporated under reduced pressure, and the aqueous layer was washed with toluene. After extraction with toluene and chloroform, washing with water was performed using 20 wt % sodium chloride-containing 0.2 M citrate phosphate buffer (pH 2.4), and 20 wt % sodium chloride-containing 0.2M citrate phosphate buffer (pH 6.5). Furthermore, the organic layer was washed with 20 wt % brine, dried over anhydrous magnesium sulfate, and filtered. The solvent was evaporated under reduced pressure to give a compound of the formula (30).

$^1$H-NMR ($CDCl_3$, internal standard TMS); δ(ppm): 2.13-2.57 (6H, m, >$CCH_2$—NHCO—$CH_2$—, —OC(O)—NH—$CH_2$—$CH_2$—, —NHCO—$CH_2$—$CH_2$-maleimide), 3.38 (6H, s, —O—$CH_3$), 2.90-3.80 (111H, m, >C($CH_2$O)$_2$—, —O—($CH_2CH_2$O)$_{12}$—, —CH—$CH_2$-phenyl, >CNH—$CH_2$—OC(O)—NH—$CH_2$—$CH_2$—, —CONH—$CH_2$—CONH-phenyl-$CH_2$—OH, —$CH_2$-maleimide, >$CCH_2$—NHCO—$CH_2$—$CH_2$—NHCO—, —CH—$CH_2$-phenyl), 3.80-4.57 (6H, —CONH-phenyl-$CH_2$—OH, —($CH_2$)$_2$—CONH—CH—CONH—$CH_2$—, —($CH_2$)$_2$—CONH—CH—CONH—$CH_2$—, —($CH_2$)$_2$—CONH—CH—CONH—$CH_2$—, —$CH_2$—OH), 4.61 (2H, >CNH—$CH_2$—OC(O)—NH—), 6.01 (1H, brs, >CNH—$CH_2$—OC(O)—NH—), 6.53 (1H, brs, >$CCH_2$—NHCO—$CH_2$—$CH_2$—), (29)

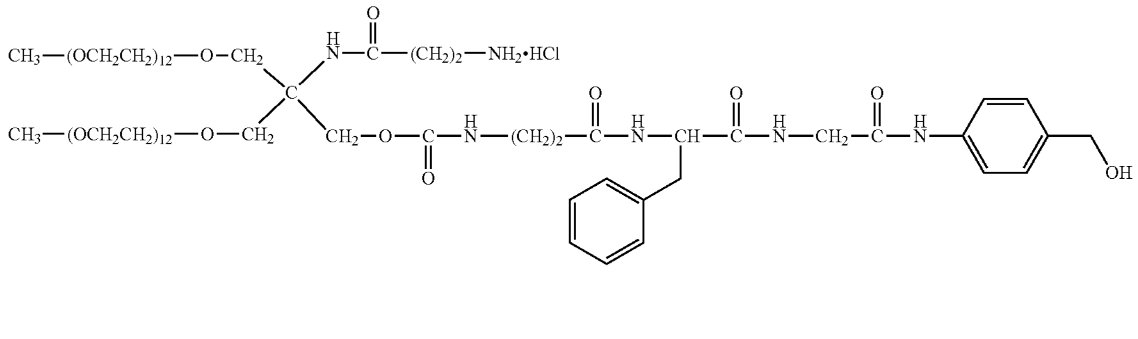

6.69 (2H, s, -maleimide), 7.20-7.80 (9H, m, arom.H), 8.87 (1H, brs, —CONH—phenyl-$CH_2$—OH)

-maleimide), 7.16-7.30 (5H, m, arom.H), 7.32 (1H, brs, >CNH—$CH_2$—OC(O)—NH—), 7.40 (2H, d, —CONH--

(30)

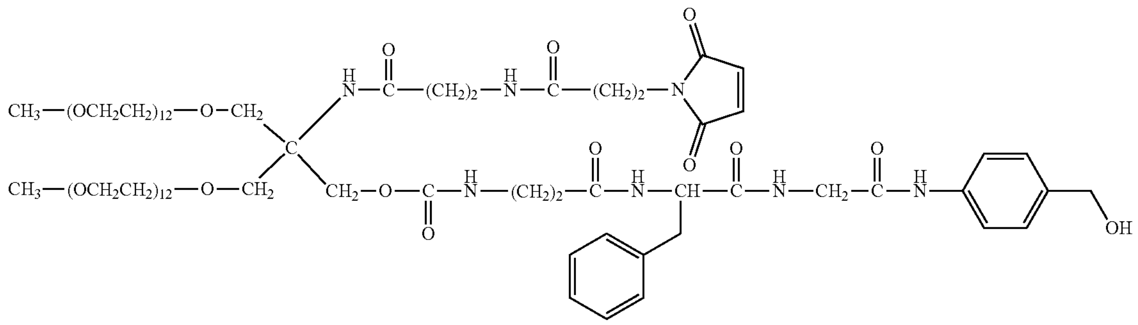

Example 21 Synthesis of Compound 31

A compound of the formula (30) (0.100 g, 0.054 mmol), di(N-succinimidyl) carbonate (0.058 g, 0.227 mmol), triethylamine (0.025 g, 0.243 mmol), and 2,6-di-tert-butyl-p-phenyl—$CH_2$—OC(O)O—), 7.65 (2H, d, —CONH—phenyl—$CH_2$—OC(O)O—), 7.83-7.92 (1H, brs, —NHCO—$CH_2$—$CH_2$-maleimide), 8.20-8.45 (2H, m, —CONH—CH—CONH—$CH_2$—, —CONH—CH—CONH—$CH_2$—), 9.91 (1H, brs, —CONH-phenyl-$CH_2$—OC(O) 0-)

(31)

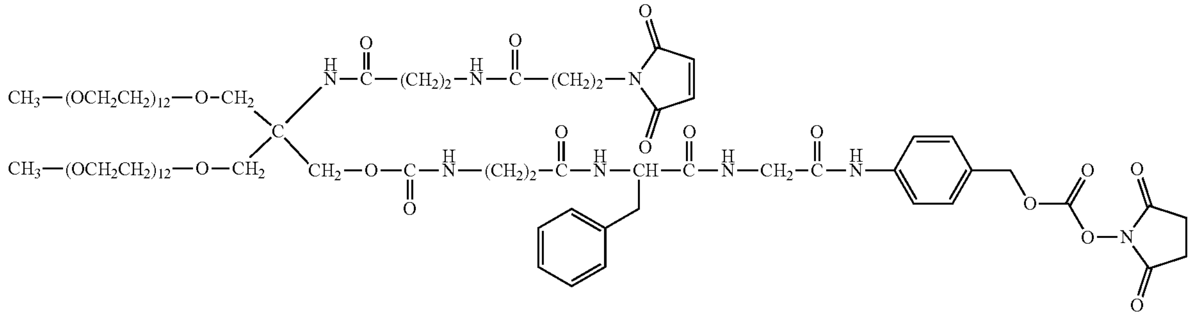

cresol (0.02 mg) were charged in a 6 ml screw tube with a stirrer, and reacted at 25° C. for 2 hr. The reaction mixture was washed with water using 15 wt % sodium chloride-containing 0.2 M citrate phosphate buffer (pH 2.4), acetonitrile, hexane, and 0.2M citrate phosphate buffer (pH 7.0) were charged and washing was performed. The organic layer was washed with 15 wt % sodium chloride-containing 0.2 M citrate phosphate buffer (pH 2.4), dried over anhydrous sodium sulfate, and filtered. The solvent was evaporated under reduced pressure to give a compound of the formula (31).

$^1$H-NMR (DMSO-d6, internal standard TMS); δ(ppm): 2.17-2.33 (6H, m, >CNHCO—$CH_2$—$CH_2$—, —NHCO—$CH_2$—$CH_2$-maleimide, —OC(O)—NH—$CH_2$—$CH_2$—), 2.61 (4H, s, —N-succinimidyl), 2.75-2.83 (1H, m, >CH—$CH_2$-phenyl), 3.04-3.18 (4H, m, >CNHCO—$CH_2$—$CH_2$—, >CNH—$CH_2$—OC(O)—NH—$CH_2$—$CH_2$—), 3.24 (6H, s, —O—$CH_3$), 3.41-3.70 (104H, m, >C($CH_2$O)$_2$—, —O—($CH_2CH_2O$)$_{12}$—, —CONH—$CH_2$—CONH-phenyl-$CH_2$—OC(O)—, —$CH_2$-maleimide), 3.80-4.00 (2H, m, >CH—$CH_2$-phenyl), 4.14 (2H, s, >CNH—$CH_2$—OC(O)—NH—), 4.45-4.57 (1H, m, >C$CH_2$—NHCO—$CH_2$—$CH_2$—), 4.94 (2H, s, —CONH-phenyl-$CH_2$—OC(O)O—), 6.99 (2H, s, Example 22 Synthesis of Compound 32

A compound of the formula (30) (0.100 g, 0.054 mmol), p-nitrophenyl chloroformate (0.026 g, 0.130 mmol), N-phenylmorpholine (0.026 g, 0.227 mmol), and dichloromethane (0.716 g) were charged in a 4 ml screw tube with a stirrer, and reacted at 25° C. for 12 hr. Distilled water (0.016 g, 0.0756 mmol) and N-phenylmorpholine (0.044 g, 0.270 mmol) were added to quench the reaction, and the mixture was diluted with hexane, and washed with 20 wt % sodium chloride-containing 0.2M hydrochloric acid. The organic layer was washed with 10 wt % sodium chloride-containing 0.15 M borate buffer (pH 10) and 10 wt % sodium chloride-containing 5 wt % aqueous sodium dihydrogen phosphate solution, dried over anhydrous sodium sulfate, and filtered. The solvent was evaporated under reduced pressure. The residue was dissolved in acetonitrile, and washed with hexane and t-butanol. The solvent was evaporated under reduced pressure to give a compound of the formula (32).

$^1$H-NMR (DMSO-d6, internal standard TMS); δ(ppm): 2.19-2.32 (6H, m, >CNHCO—$CH_2$—$CH_2$—, —NHCO—$CH_2$—$CH_2$-maleimide, —OC(O)—NH—$CH_2$—$CH_2$—), 2.72-2.82 (1H, m, >CH—$CH_2$-phenyl), 3.03-3.22 (4H, m, >CNHCO—$CH_2$—$CH_2$—, >CNH—$CH_2$—OC(O)—NH—$CH_2$—$CH_2$—), 3.23 (6H, s, —O—$CH_3$), 3.38-3.70 (104H, m, >$C(CH_2O)_2$—, —O—$(CH_2CH_2O)_{12}$—, —CONH—$CH_2$—CONH-phenyl-$CH_2$—OC(O)—, —$CH_2$-maleimide), 3.80-3.96 (2H, m, >CH—$CH_2$-phenyl), 4.15 (2H, s, >CNH—$CH_2$—OC(O)—NH—), 4.45-4.56 (1H, brs, >CNHCO—$CH_2$—$CH_2$—), 5.25 (2H, s, —CONH-phenyl-$CH_2$—OC(O)O—), 6.99 (2H, s, -maleimide), 7.14-7.35 (6H, m, arom.H, >CNH—$CH_2$—OC(O)—NH—), 7.42 (2H, d, —CONH—phenyl—$CH_2$—OC(O)O—), 7.54-7.60 (2H, m, arom.H(p-nitrophenyl)), 7.64-7.72 (2H, d, —CONH—phenyl—$CH_2$—OC(O)O—), 7.83-7.92 (1H, m, —NHCO—$CH_2$—$CH_2$-maleimide), 8.22-8.43 (4H, m, —CONH—CH—CONH—$CH_2$—, —CONH—CH—CONH—$CH_2$—, arom.H(p-nitrophenyl)), 9.90 (1H, brs, —CONH-phenyl-$CH_2$—OC(O)O—)

(32)

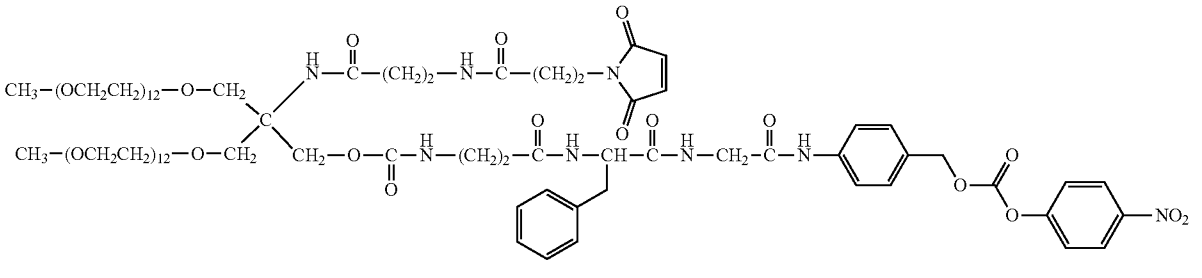

Example 23 Synthesis of Compound 33

A compound of the formula (28) (0.100 g, 0.052 mmol), di(N-succinimidyl) carbonate (0.056 g, 0.218 mmol), triethylamine (0.024 g, 0.234 mmol), and 2,6-di-tert-butyl-p-cresol (0.02 mg) were charged in a 6 ml screw tube with a stirrer, and reacted at 25° C. for 2 hr. Thereafter, purification similar to that in Example 16 was performed to give a compound of the formula (33).

$^1$H-NMR ($CDCl_3$, internal standard TMS); δ(ppm): 2.20-2.45 (4H, m, >$CCH_2$—NHCO—$CH_2$—$CH_2$—, —OC(O)—NH—$CH_2$—$CH_2$—), 2.82 (4H, s, —N-succinimidyl), 3.38 (6H, s, —O—$CH_3$), 2.90-3.80 (108H, m, >$C(CH_2O)_2$—, —O—$(CH_2CH_2O)_{12}$—, —CH—$CH_2$-phenyl, >CNH—$CH_2$—OC(O)—NH—$CH_2$—$CH_2$—, >$CCH_2$—NHCO—$CH_2$—$CH_2$—NHCO—, —CONH—$CH_2$—CONH-phenyl-$CH_2$—), 3.80-4.65 (8H, —NH—C(O)O—$CH_2$-Fmoc, >CNH—$CH_2$—OC(O)—NH—, —$CH_2$—Fmoc(CH), —$(CH_2)_2$—CONH—CH—CONH—$CH_2$—, —$(CH_2)_2$—CONH—CH—CONH—$CH_2$—, —$(CH_2)_2$—CONH—CH—CONH—$CH_2$—), 5.26 (2H, s, —CONH-phenyl-$CH_2$—OC(O)O—), 6.02-6.15 (2H, m, —NH—C(O)O—$CH_2$-Fmoc, >CNH—$CH_2$—OC(O)—NH—), 6.53 (1H, brs, >$CCH_2$—NHCO—$CH_2$—$CH_2$—), 7.11-7.84 (17H, m, arom.H), 8.89 (1H, brs, —CONH-phenyl-$CH_2$—OC(O)O—)

(33)

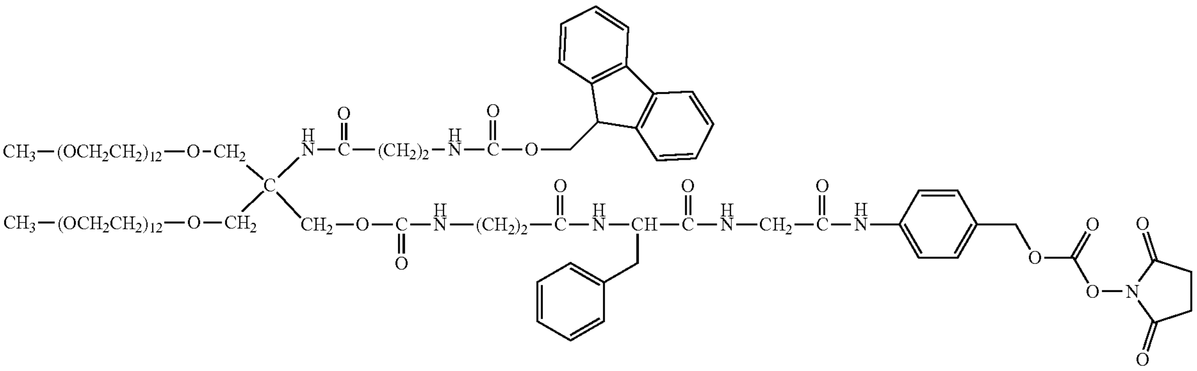

Example 24 Synthesis of Compound 34

A compound of the formula (27) (0.300 g, 0.186 mmol), L-valine-citrulline with C-terminal condensed with p-aminobenzyl alcohol (pAB) (H-Val-Cit-pAB) (0.088 g, 0.233 mmol, manufactured by WATANABE CHEMICAL INDUSTRIES, LTD.), DMT-MM (0.080 g, 0.233 mmol), acetonitrile (3.00 g), and N,N-diisopropylethylamine (0.031 g, 0.242 mmol) were charged in a 14 mL screw tube with a stirrer, and reacted at 25° C. for 2 hr. A 5 wt % aqueous sodium dihydrogen phosphate solution (1.80 g) was added, acetonitrile was evaporated under reduced pressure, and the aqueous layer was washed with toluene. Thereafter, purification similar to that in Example 5 was performed to give a compound of the formula (34).

$^1$H-NMR (DMSO-d6, internal standard TMS); δ(ppm): 0.76-0.92 (6H, m, >CH—CH(C$\underline{H_3}$)$_2$), 1.30-1.48 (2H, m, —CH$_2$—C$\underline{H_2}$—CH$_2$—NHCO—NH$_2$), 1.55-1.78 (2H, m, —C$\underline{H_2}$—CH$_2$—CH$_2$—NHCO—NH$_2$), 1.92-2.04 (1H, m, >CH—C$\underline{H}$(CH$_3$)$_2$), 2.22-2.44 (4H, m, >CNHCO—C$\underline{H_2}$—CH$_2$—NHCO—, >CCH$_2$—O—CONH—CH$_2$—C$\underline{H_2}$—), 2.87-3.10 (2H, m, —CH$_2$—CH$_2$—C$\underline{H_2}$—NHCO—NH$_2$), 3.23 (6H, s, —O—C$\underline{H_3}$), 3.40-3.72 (104H, m, >C(C$\underline{H_2}$O)$_2$—, —O—(C$\underline{H_2}$C$\underline{H_2}$O)$_{12}$—, >CNHCO—CH$_2$—C$\underline{H_2}$—NHCO—, >CCH$_2$—O—CONH—C$\underline{H_2}$—CH$_2$—), 4.15 (2H, brs, >CC$\underline{H_2}$—O—CONH—), 4.18-4.24 (2H, m, —CH$_2$—$\underline{\text{Fmoc(CH)}}$, >C$\underline{H}$—CH(CH$_3$)$_2$), 4.25-4.32 (2H, m, —C$\underline{H_2}$-Fmoc(CH)), 4.36-4.42 (1H, m, >C$\underline{H}$—CH$_2$—CH$_2$—CH$_2$—NHCO—NH$_2$), 4.42 (2H, d, —CONH-phenyl-C$\underline{H_2}$—OH), 5.08 (1H, t, —CONH-phenyl-CH$_2$—O$\underline{H}$), 5.40 (2H, brs, —CH$_2$—CH$_2$—CH$_2$—NHCO—N$\underline{H_2}$), 5.94-6.05 (1H, m, —CH$_2$—CH$_2$—CH$_2$—N$\underline{H}$CO—NH$_2$), 7.02-7.10 (1H, m, >CCH$_2$—O—CON$\underline{H}$—CH$_2$—CH$_2$—), 7.16-7.28 (3H, m, >CNHCO—CH$_2$—CH$_2$—N$\underline{H}$CO—, —CONH-$\underline{\text{phenyl}}$—CH$_2$—OH), 7.31-7.47 (5H, m, >CN$\underline{H}$CO—CH$_2$—CH$_2$—NHCO—, $\underline{\text{arom.H(Fmoc)}}$), 7.54 (2H, d, —CONH—$\underline{\text{phenyl}}$—CH$_2$—OH), 7.67 (2H, d, $\underline{\text{arom.H(Fmoc)}}$), 7.83-8.16 (4H, m, —(CH$_2$)$_2$—CON$\underline{H}$—CH—CONH—CH—, —(CH$_2$)$_2$—CONH—CH—CON$\underline{H}$—CH—, $\underline{\text{arom.H(Fmoc)}}$), 9.88 (1H, brs, —CON$\underline{H}$-phenyl-CH$_2$—OH)

Example 25 Synthesis of Compound 35

A compound of the formula (34) (0.150 g, 0.076 mmol), piperidine (0.120 g, 1.52 mmol), and chloroform (1.34 g) were added to a 9 mL screw tube with a stirrer, and reacted at 25° C. for 3 hr. The reaction mixture was washed with water using 20 wt % sodium chloride-containing 0.2 M hydrochloric acid, the organic layer was diluted with toluene, and extracted with distilled water into an aqueous layer. The aqueous layer adjusted to pH 10 with 400 g/L aqueous sodium hydroxide solution was washed with toluene and chloroform. Sodium chloride was dissolved in the aqueous layer to give 15 wt % brine and the aqueous layer was extracted with chloroform. The organic layer was dried over anhydrous sodium sulfate and filtered. The solvent was evaporated under reduced pressure to give a compound of the formula (35).

$^1$H-NMR (DMSO-d6, internal standard TMS); δ(ppm): 0.76-0.92 (6H, m, >CH—CH(C$\underline{H_3}$)$_2$), 1.30-1.50 (2H, m, —CH$_2$—C$\underline{H_2}$—CH$_2$—NHCO—NH$_2$), 1.52-1.75 (2H, m, —C$\underline{H_2}$—CH$_2$—CH$_2$—NHCO—NH$_2$), 1.92-2.02 (1H, m, >CH—C$\underline{H}$(CH$_3$)$_2$), 2.13-2.43 (4H, m, >CNHCO—C$\underline{H_2}$—CH$_2$—NH$_2$, >CCH$_2$—O—CONH—CH$_2$—C$\underline{H_2}$—), 2.68-2.80 (2H, m, >CNHCO—CH$_2$—C$\underline{H_2}$—NH$_2$), 2.87-3.08 (2H, m, —CH$_2$—CH$_2$—C$\underline{H_2}$—NHCO—NH$_2$), 3.24 (6H, s, —O—C$\underline{H_3}$), 3.15-3.70 (102H, m, >C(C$\underline{H_2}$O)$_2$—, —O—(C$\underline{H_2}$C$\underline{H_2}$O)$_{12}$—, >CCH$_2$—O—CONH—C$\underline{H_2}$—CH$_2$—), 4.16 (2H, brs, >CC$\underline{H_2}$—O—CONH—), 4.20 (1H, t, >C$\underline{H}$—CH(CH$_3$)$_2$), 4.36-4.41 (1H, m, >C$\underline{H}$—CH$_2$—CH$_2$—CH$_2$—NHCO—NH$_2$), 4.42 (2H, d, —CONH-phenyl-C$\underline{H_2}$—OH), 5.08 (1H, brs, —CONH-phenyl-CH$_2$—O$\underline{H}$), 5.41 (2H, brs, —CH$_2$—CH$_2$—CH$_2$—NHCO—N$\underline{H_2}$), 6.00 (1H, brs, —CH$_2$—CH$_2$—CH$_2$—N$\underline{H}$CO—NH$_2$), 7.04 (1H, brs, >CCH$_2$—O—CON$\underline{H}$—CH$_2$—CH$_2$—), 7.18-7.28 (2H, m, —CONH—$\underline{\text{phenyl}}$—CH$_2$—OH), 7.48-7.63 (3H, m, —CONH—$\underline{\text{phenyl}}$—CH$_2$—OH, >CN$\underline{H}$CO—CH$_2$—CH$_2$—NH$_2$), 7.89-8.20 (2H, m, —(CH$_2$)$_2$—CON$\underline{H}$—CH—CONH—CH—, —(CH$_2$)$_2$—CONH—CH—CON$\underline{H}$—CH—), 9.89 (1H, brs, —CON$\underline{H}$-phenyl-CH$_2$—OH)

(34)

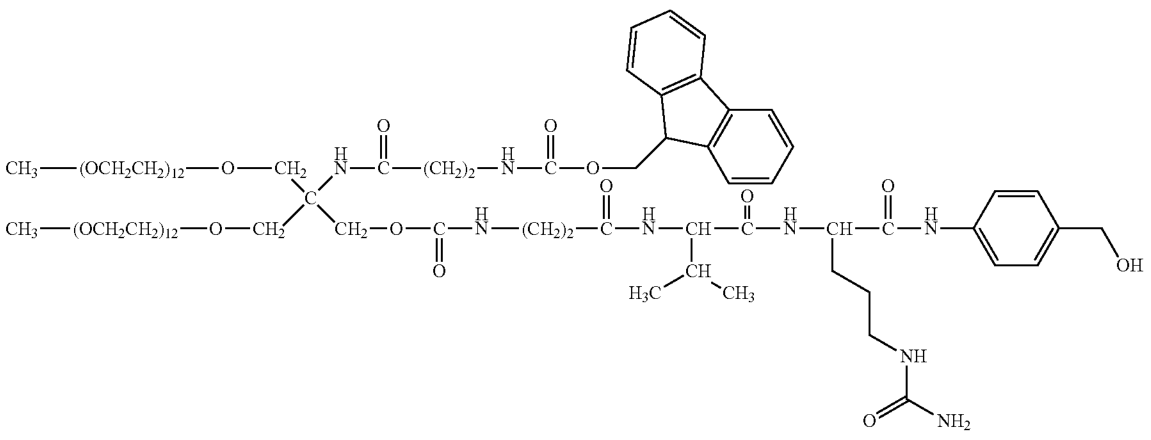

(35)

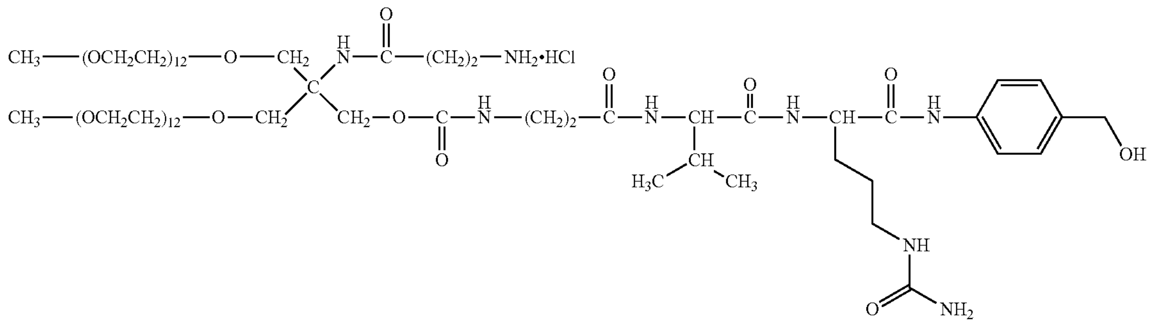

Example 26 Synthesis of Compound 36

A compound of the formula (35) (0.100 g, 0.057 mmol), 3-maleimidopropionic acid (0.011 g, 0.063 mmol), DMT-MM (0.022 g, 0.063 mmol), triethylamine (6.9 mg, 0.068 mmol), and acetonitrile (0.900 g) were added to a 6 ml screw tube with a stirrer, and reacted at 25° C. for 2 hr under (2H, s, -maleimide), 7.04 (1H, brs, >$CCH_2$—O—CONH—$CH_2$—$CH_2$—), 7.22-7.32 (3H, m, —CONH—phenyl—$CH_2$—OH, >CNHCO—$CH_2$—$CH_2$—), 7.54 (2H, d, —CONH-phenyl—$CH_2$—OH), 7.88-8.16 (3H, m, >CNHCO—$CH_2$—$CH_2$—NHCO—, —$(CH_2)_2$—CONH—CH—CONH—CH—, —$(CH_2)_2$—CONH—CH—CONH—CH—), 9.88 (1H, brs, —CONH-phenyl-$CH_2$—OH)

(36)

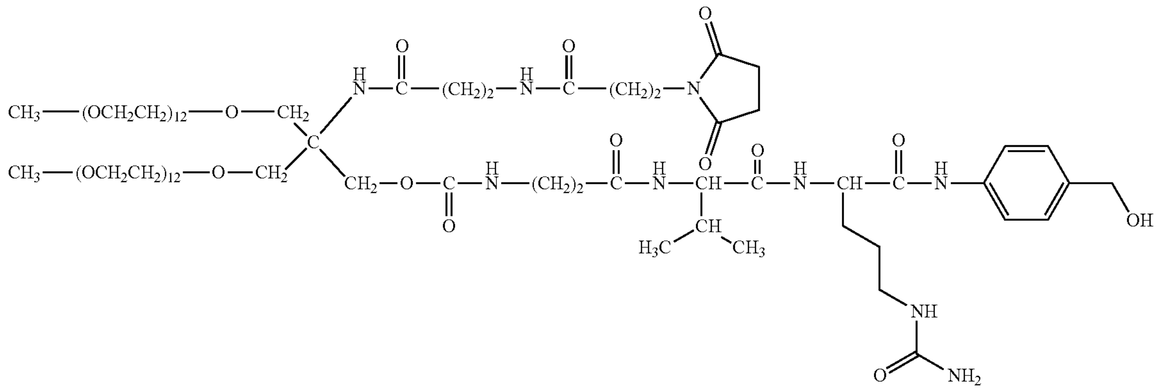

shading. a 0.2 M citrate phosphate buffer (pH 3.0) (1.20 g) was added, acetonitrile was evaporated under reduced pressure, and the aqueous layer was washed with toluene. Thereafter, purification similar to that in Example 20 was performed to give a compound of the formula (36).

$^1$H-NMR ($CDCl_3$, internal standard TMS); δ(ppm): 0.76-0.92 (6H, m, >CH—$CH(CH_3)_2$), 1.32-1.48 (2H, m, —$CH_2$—$CH_2$—$CH_2$—NHCO—$NH_2$), 1.52-1.77 (2H, m, —$CH_2$—$CH_2$—$CH_2$—NHCO—$NH_2$), 1.93-2.02 (1H, m, >CH—$CH(CH_3)_2$), 2.17-2.44 (6H, m, >CNHCO—$CH_2$—$CH_2$—NHCO—$CH_2$—$CH_2$—, >CNHCO—$CH_2$—$CH_2$—NHCO—$CH_2$—$CH_2$—, >$CCH_2$—O—CONH—$CH_2$—$CH_2$—), 2.87-3.08 (2H, m, —$CH_2$—$CH_2$—$CH_2$—NHCO—$NH_2$), 3.24 (6H, s, —O—$CH_3$), 3.13-3.74 (106H, m, >$C(CH_2O)_2$—, —O—$(CH_2CH_2O)_{12}$—, >CNHCO—$CH_2$—$CH_2$—NHCO—$CH_2$—$CH_2$—, >CNHCO—$CH_2$—$CH_2$—NHCO—$CH_2$—$CH_2$—, >$CCH_2$—O—CONH—$CH_2$—$CH_2$—), 4.15 (2H, brs, >$CCH_2$—O—CONH—), 4.16-4.23 (1H, m, >CH—$CH(CH_3)_2$), 4.34-4.41 (1H, m, >CH—$CH_2$—$CH_2$—$CH_2$—NHCO—$NH_2$), 4.42 (2H, d, —CONH-phenyl-$CH_2$—OH), 5.08 (1H, t, —CONH-phenyl-$CH_2$—OH), 5.40 (2H, brs, —$CH_2$—$CH_2$—$CH_2$—NHCO—$NH_2$), 5.99 (1H, brs, —$CH_2$—$CH_2$—$CH_2$—NHCO—$NH_2$), 7.00

Example 27 Synthesis of Compound 37

A compound of the formula (36) (0.100 g, 0.0483 mmol), bis(4-nitrophenyl) carbonate (0.029 g, 0.0966 mmol), N,N-diisopropylamine (0.0094 g, 0.0725 mmol), and dichloromethane (0.640 g) were charged in a 4 ml screw tube with a stirrer, and reacted at 25° C. for 3 hr. The reaction mixture was washed with 20 wt % sodium chloride-containing 0.2M hydrochloric acid. Furthermore, the organic layer was washed with 10 wt % sodium chloride-containing 0.15 M borate buffer (pH 10) and 20 wt % sodium chloride-containing 5 wt % aqueous sodium dihydrogen phosphate solution, dried over anhydrous sodium sulfate, and filtered. The solvent was evaporated under reduced pressure. The residue was dissolved in acetonitrile, and the mixture was washed with hexane and t-butanol. The solvent was evaporated under reduced pressure to give a compound of the formula (37).

$^1$H-NMR (DMSO-d6, internal standard TMS); δ(ppm): 0.78-0.92 (6H, m, >CH—$CH(CH_3)_2$), 1.32-1.52 (2H, m, —$CH_2$—$CH_2$—$CH_2$—NHCO—$NH_2$), 1.54-1.80 (2H, m, —$CH_2$—$CH_2$—$CH_2$—NHCO—$NH_2$), 1.93-2.02 (1H, m, >CH—$CH(CH_3)_2$), 2.16-2.42 (6H, m, >CNHCO—$CH_2$—

$CH_2$—NHCO—, >CNHCO—$CH_2$—$CH_2$—NHCO—$CH_2$—$CH_2$—, >$CCH_2$—O—CONH—$CH_2$—$CH_2$—), 2.90-3.08 (2H, m, —$CH_2$—$CH_2$—$CH_2$—NHCO—$NH_2$), 3.24 (6H, s, —O—$CH_3$), 3.13-3.75 (106H, m, >C($CH_2$O)$_2$—, —O—($CH_2CH_2O$)$_{12}$—, >CNHCO—$CH_2$—$CH_2$—NHCO—, >CNHCO—$CH_2$—$CH_2$—NHCO—$CH_2$—$CH_2$—, >$CCH_2$—O—CONH—$CH_2$—$CH_2$—), 4.15 (2H, brs, >$CCH_2$—O—CONH—), 4.20 (1H, t, >CH—CH($CH_3$)$_2$), 4.33-4.46 (1H, m, >CH—$CH_2$—$CH_2$—$CH_2$—NHCO—$NH_2$), 5.24 (2H, brs, —CONH-phenyl-$CH_2$—O—), 5.42 (2H, brs, —$CH_2$—$CH_2$—$CH_2$—NHCO—$NH_2$), 6.00 (1H, brs, —$CH_2$—$CH_2$—$CH_2$—NHCO—$NH_2$), 7.00 (2H, s, -maleimide), 7.05 (1H, brs, >$CCH_2$—O—CONH—$CH_2$—$CH_2$—), 7.32 (1H, brs, >CNHCO—$CH_2$—$CH_2$—NHCO—), 7.37-7.47 (2H, m, —CONH-phenyl—$CH_2$—O—), 7.57 (2H, d, arom.H(p-nitrophenyl)), 7.63-7.68 (2H, m, —CONH—phenyl—$CH_2$—O—), 7.80-8.18 (3H, m, >CNHCO—$CH_2$—$CH_2$—NHCO—, —($CH_2$)$_2$—CONH—CH—CONH—CH—, —($CH_2$)$_2$—CONH—CH—CONH—CH—), 8.31 (2H, d, arom.H(p-nitrophenyl)), 10.1 (1H, brs, —CONH-phenyl-$CH_2$—O—)

taining 5 wt % aqueous sodium dihydrogen phosphate solution, dried over anhydrous sodium sulfate, and filtered. The solvent was evaporated under reduced pressure. The residue was dissolved in acetonitrile, and washed with hexane and t-butanol. The solvent was evaporated under reduced pressure to give a compound of the formula (38). $^1$H-NMR (DMSO-d6, internal standard TMS); δ(ppm): 0.77-0.90 (6H, m, >CH—CH($CH_3$)$_2$), 1.33-1.51 (2H, m, —$CH_2$—$CH_2$—$CH_2$—NHCO—$NH_2$), 1.53-1.78 (2H, m, —$CH_2$—$CH_2$—$CH_2$—NHCO—$NH_2$), 1.93-2.03 (1H, m, >CH—CH($CH_3$)$_2$), 2.22-2.43 (4H, m, >CNHCO—$CH_2$—$CH_2$—NHCO—, >$CCH_2$—O—CONH—$CH_2$—$CH_2$—), 2.87-3.15 (2H, m, —$CH_2$—$CH_2$—$CH_2$—NHCO—$NH_2$), 3.23 (6H, s, —O—$CH_3$), 3.13-3.70 (104H, m, >C($CH_2$O)$_2$—, —O—($CH_2CH_2O$)$_{12}$—, >CNHCO—$CH_2$—$CH_2$—NHCO—, >$CCH_2$—O—CONH—$CH_2$—$CH_2$—), 4.13-4.23 (4H, m, >$CCH_2$—O—CONH—, —$CH_2$—Fmoc(CH), >CH—CH($CH_3$)$_2$), 4.24-4.29 (2H, m, —$CH_2$—Fmoc(CH)), 4.36-4.42 (1H, m, >CH—$CH_2$—$CH_2$—$CH_2$—NHCO—$NH_2$), 5.24 (2H, brs, —CONH-phenyl-$CH_2$—OH), 5.41 (2H, brs, —$CH_2$—$CH_2$—$CH_2$—NHCO—$NH_2$), 6.00 (1H, (37)

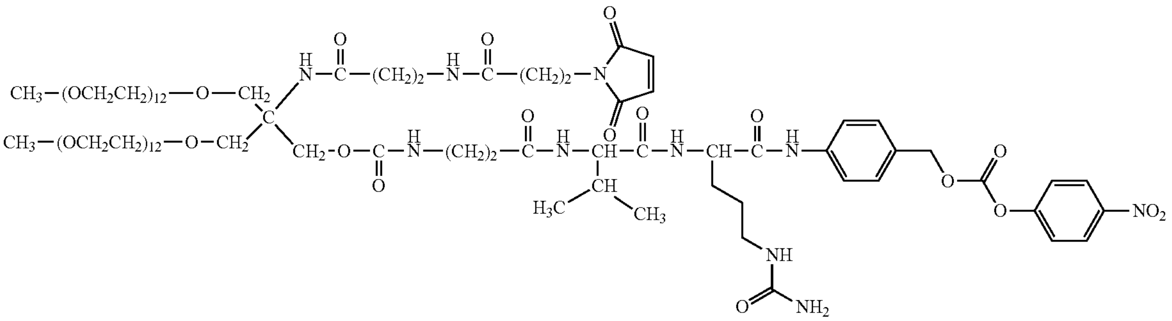

Example 28 Synthesis of Compound 38

A compound of the formula (34) (0.100 g, 0.0506 mmol), bis(4-nitrophenyl) carbonate (0.031 g, 0.101 mmol), N,N-diisopropylamine (0.0098 g, 0.0759 mmol), and dichloromethane (0.671 g) were charged in a 4 ml screw tube with a stirrer, and reacted at 25° C. for 3 hr. The reaction mixture was washed with 20 wt % sodium chloride-containing 0.2 M hydrochloric acid. Furthermore, the organic layer was washed with 10 wt % sodium chloride-containing 0.15 M borate buffer (pH 10) and 20 wt % sodium chloride-conbrs, —$CH_2$—$CH_2$—$CH_2$—NHCO—$NH_2$), 7.04 (1H, brs, >$CCH_2$—O—CONH—$CH_2$—$CH_2$—), 7.19 (1H, brs, >CNHCO—$CH_2$—$CH_2$—NHCO—), 7.31-7.38 (3H, m, >CNHCO—$CH_2$—$CH_2$—NHCO—, arom.H(Fmoc)), 7.38-7.46 (4H, m, —CONH—phenyl—$CH_2$—OH, arom.H (Fmoc)), 7.56-7.71 (6H, m, —CONH-phenyl—$CH_2$—OH, arom.H(Fmoc, p-nitrophenyl)), 7.87-8.20 (4H, m, —($CH_2$)$_2$—CONH—CH—CONH—CH—, —($CH_2$)$_2$—CONH—CH—CONH—CH—, arom.H(Fmoc)), 8.28-8.33 (2H, m, arom.H(p-nitrophenyl)), 10.1 (1H, brs, —CONH-phenyl-$CH_2$—OH)

(38)

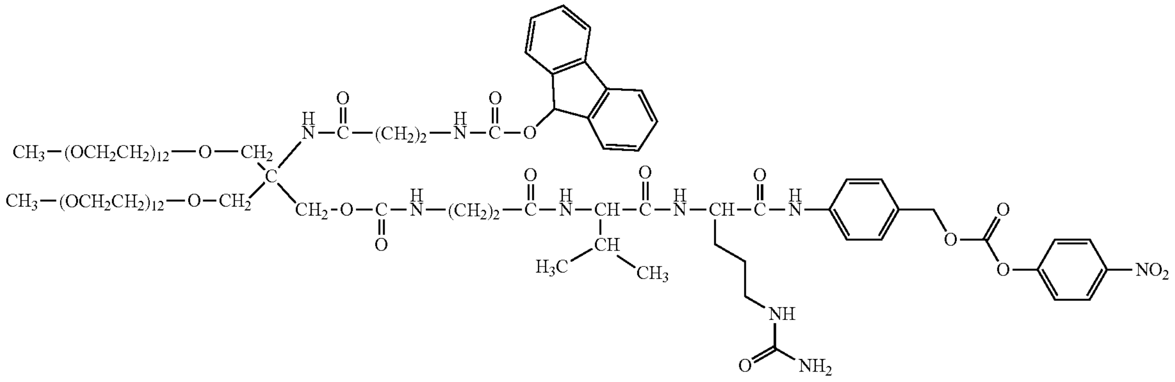

Example 29 Conjugate of Compound 31 and Doxorubicin

Doxorubicin hydrochloride (2.62 mg, 4.51 μmol), N,N-diisopropylamine (1.55 mg, 11.5 μmol), N,N-dimethylformamide, and a compound of the formula (31) (10.0 mg, 5.01 μmol) were charged in a 4 ml screw tube with a stirrer, and reacted at 25° C. for 4 hr. The reaction mixture was diluted with dichloromethane, and washed with water using 5 wt % aqueous sodium dihydrogen phosphate solution and ion exchange water. The organic layer was dried over anhydrous sodium sulfate, and filtered. The solvent was evaporated under reduced pressure to give a drug-linker compound of the formula (39).

Example 30 Conjugate of Compound 33 and Doxorubicin

Doxorubicin hydrochloride (2.53 mg, 4.36 μmol), N,N-diisopropylamine (1.50 mg, 11.1 μmol), N,N-dimethylformamide, and a compound of the formula (33) (10.0 mg, 4.84 μmol) were charged in a 4 ml screw tube with a stirrer, and reacted at 25° C. for 4 hr. Thereafter, purification similar to that in Example 29 was performed to give a drug-linker compound of the formula (40).

(39)

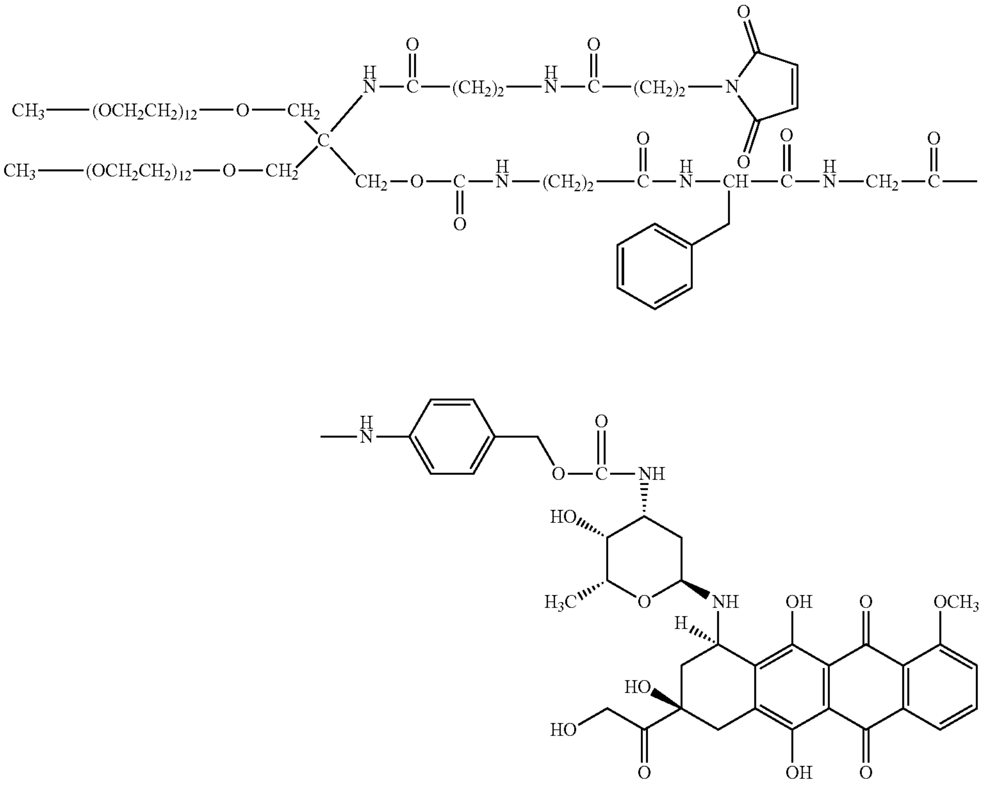

(40)

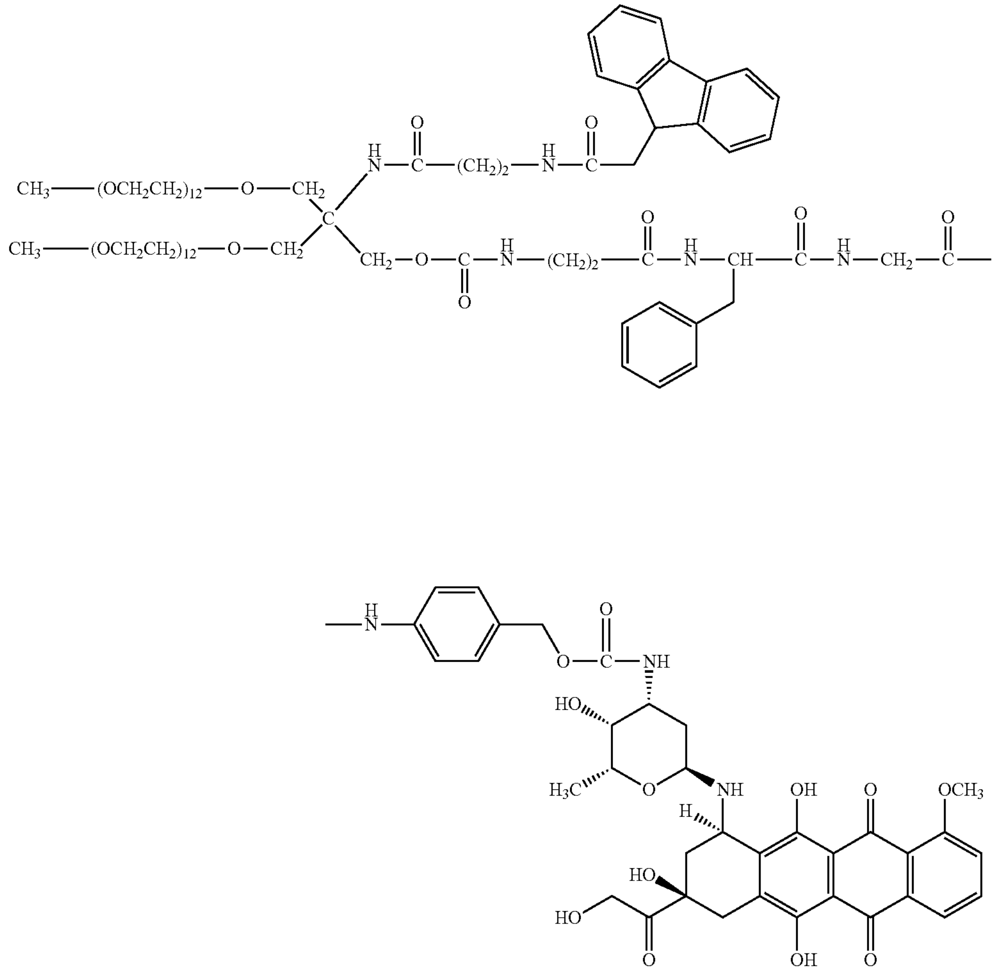

Example 31 Conjugate of Compound 37 and Doxorubicin

Doxorubicin hydrochloride (2.62 mg, 4.51 μmol), N,N-diisopropylamine (1.55 mg, 11.5 μmol), N,N-dimethylformamide, and a compound of the formula (37) (10.4 mg, 5.01 μmol) were charged in a 4 ml screw tube with a stirrer, and reacted at 25° C. for 4 hr. The reaction mixture was diluted with dichloromethane, and washed with water using 5 wt % aqueous sodium dihydrogen phosphate solution, 5 wt % aqueous disodium hydrogen phosphate solution, and ion exchange water. The organic layer was dried over anhydrous sodium sulfate, and filtered. The solvent was evaporated under reduced pressure to give a drug-linker compound of the formula (41).

(41)

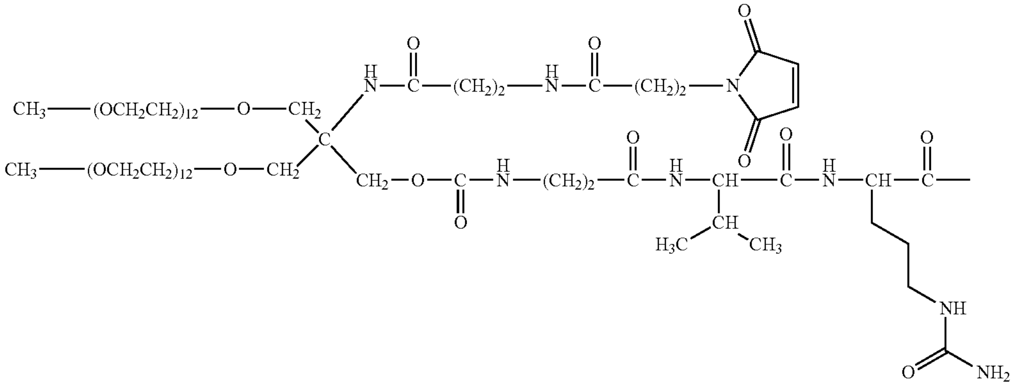

-continued

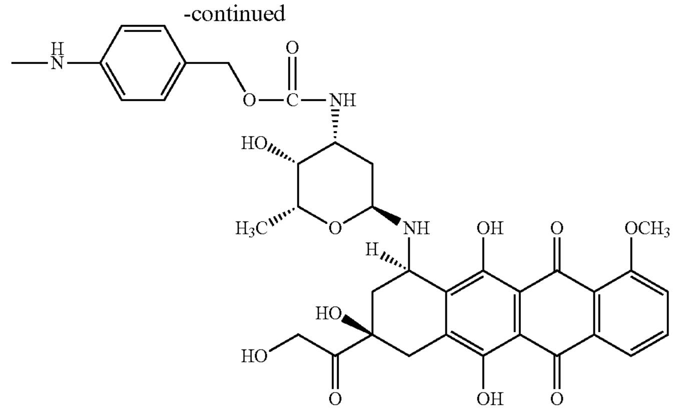

Example 32 Conjugate of Compound 38 and Doxorubicin

Doxorubicin hydrochloride (2.53 mg, 4.36 μmol), N,N-diisopropylamine (1.50 mg, 11.1 μmol), N,N-dimethylformamide, and a compound of the formula (38) (10.4 mg, 4.84 μmol) were charged in a 4 m1 screw tube with a stirrer, and reacted at 25° C. for 4 hr. Thereafter, purification similar to that in Example 31 was performed to give a drug-linker compound of the formula (42).

Example 33 Preparation of ADC Using Compound 39

A monoclonal anti-interleukin-1β antibody (0.500 mg, Sigma-Aldrich) produced in mouse was dissolved in phosphate buffered brine (PBS, 0.500 mL). This solution (0.048 mL) was placed in a 0.5 mL polypropylene tube, 50.0 mM ethylenediaminetetraacetic acid (EDTA, 0.006 mL), and 0.800 mM aqueous tris(2-carboxymethyl)phosphine hydrochloride (TCEP) solution (0.006 mL; 15 equivalents to antibody) were added thereto, and the mixture was shaken at 37° C. for 1 hr. To the above-mentioned solution was added (42)

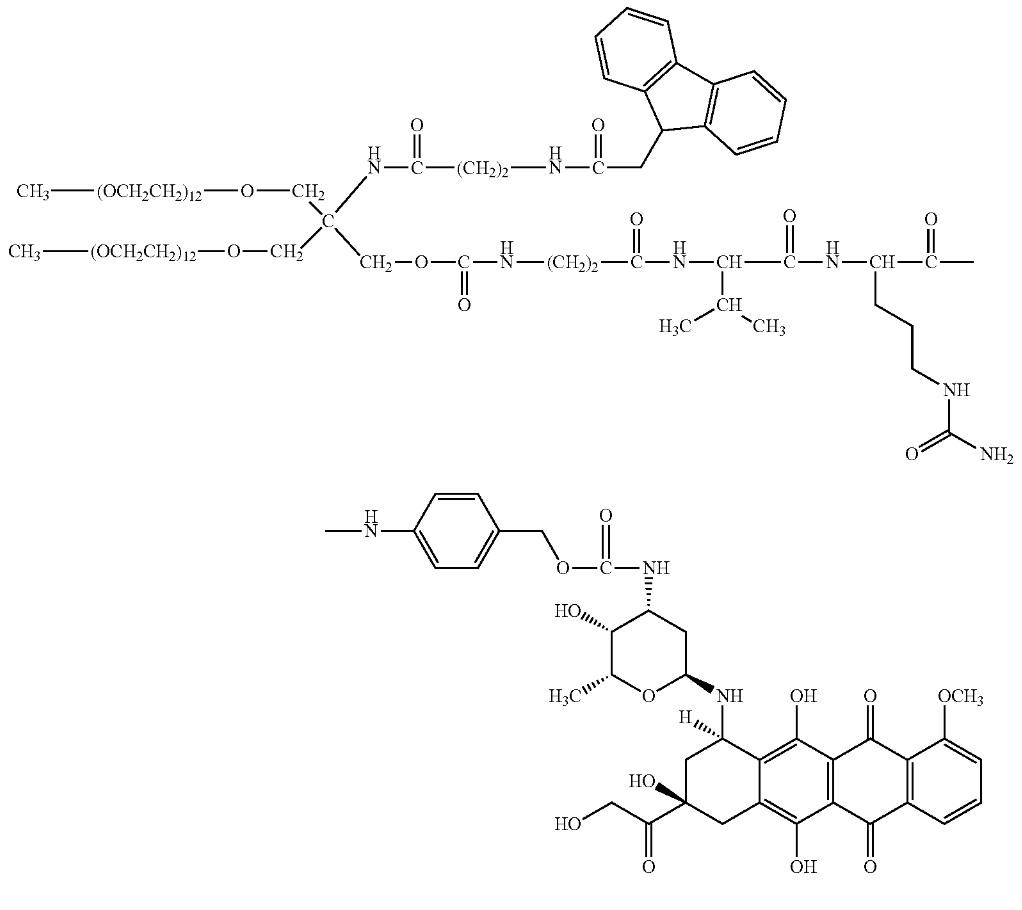

a 2.50 mM solution (0.007 mL; 53 equivalents to antibody) of the compound of the formula (39) in N,N-dimethylacetamide, and the mixture was further shaken at 20° C. for 1 hr. A 2.50 mM aqueous solution (0.007 mL; 53 equivalents to antibody) of N-acetylcysteine was added, and the obtained mixture was further shaken at 20° C. for 1 hr. The solution obtained above was filled in an NAP-5 column (GE Healthcare Life Science) equilibrated with PBS (10 mL), and eluted with PBS to separate antibody fractions.

Example 34 Preparation of ADC Using Compound 41

A monoclonal anti-interleukin-1β antibody (0.500 mg, Sigma-Aldrich) produced in mouse was dissolved in phosphate buffered brine (PBS, 0.500 mL). This solution (0.048 mL) was placed in a 0.5 mL polypropylene tube, 50.0 mM ethylenediaminetetraacetic acid (EDTA, 0.006 mL), and 0.800 mM aqueous tris(2-carboxymethyl)phosphine hydrochloride (TCEP) solution (0.006 mL; 15 equivalents to antibody) were added thereto, and the mixture was shaken at 37° C. for 1 hr. To the above-mentioned solution was added a 2.50 mM solution (0.007 mL; 53 equivalents to antibody) of the compound of the formula (41) in N,N-dimethylacetamide, and the mixture was further shaken at 20° C. for 1 hr. A 2.50 mM aqueous solution (0.007 mL; 53 equivalents to antibody) of N-acetylcysteine was added, and the obtained mixture was further shaken at 20° C. for 1 hr. The solution obtained above was filled in an NAP-5 column (GE Healthcare Life Science) equilibrated with PBS (10 mL), and eluted with PBS to separate antibody fractions.

Example 35 Calculation of Average Number of Drug Bonds Per Antibody of ADC Using Compound 39

The average number of bonds per antibody in an antibody-drug conjugate can be calculated by measuring the UV absorbance of an aqueous antibody-drug conjugate solution at two wavelengths of 280 nm and 495 nm, and then performing the following calculation.

Since the total absorbance at a certain wavelength is equal to the sum of the absorbances of all the absorbed chemical species existing in the system [absorbance additivity], assuming that there is no change in the molar absorption coefficients of the antibody and drug before and after the conjugation reaction of the antibody and the drug, the antibody concentration and the drug concentration in the antibody-drug conjugate are represented by the following relational formulas.

$$A280 = AD,280 + AA,280 = \varepsilon D,280 CD + \varepsilon A,280 CA \quad \text{formula (i)}$$

$$A495 = AD,495 + AA,495 = \varepsilon D,495 CD + \varepsilon A,495 CA \quad \text{formula (ii)}$$

As used herein, A280 indicates the absorbance of the aqueous antibody-drug conjugate solution at 280 nm, A495 indicates the absorbance of the aqueous antibody-drug conjugate solution at 495 nm, AA, 280 indicates the absorbance of the antibody at 280 nm, AA, 495 indicates the absorbance of the antibody at 495 nm, AD, 280 indicates the absorbance of the drug-linker compound at 280 nm, AD, 495 indicates the absorbance of the drug-linker compound at 495 nm, εA, 280 indicates the molar absorption coefficient of the antibody at 280 nm, εA, 495 indicates the molar absorption coefficient of the antibody at 495 nm, εD, 280 indicates the molar absorption coefficient of the drug-linker compound at 280 nm, εD, 495 indicates the molar absorption coefficient of the drug-linker compound at 495 nm, CA indicates the antibody concentration of the antibody-drug conjugate, and CD indicates the drug concentration of the antibody-drug conjugate.

Here, the values prepared in advance (assumed value or measured value obtained from UV measurement of the compound) are used for εA, 280, εA, 495, εD, 280, and εD, 495. εA, 495 is generally 0. εD, 280 and εD, 495 can be obtained by measuring the absorbance of a solution in which the linker-drug compound to be used was dissolved at a certain molar concentration, and using the Lambert-Beer law (absorbance=mol concentration×molar absorption coefficient×cell optical path length). CA and CD can be obtained by measuring A280 and A495 of an aqueous antibody-drug conjugate solution, substituting these values into the formulas (i) and (ii) to solve the simultaneous equations. Furthermore, the average number of drugs bound per antibody can be obtained by dividing CD by CA.

The above-mentioned simultaneous equations were solved using molar absorption coefficient εA, 280=206,999 (assumed value), εA, 495=0, εD, 280=10426 (measured value), εD, 495=10339 (measured value), and the average number of drug bonds per antibody was 7.8.

Example 36 Calculation of Average Number of Drug Bonds Per Antibody of ADC Using Compound 41

By a method similar to that in Example 35, calculations were performed using the molar absorption coefficients εA, 280=206,999 (assumed value), εA, 495=0, εD, 280=9837 (measured value), εD, 495=9785 (measured value), and the average number of drug bonds per antibody was 8.1.

Comparative Example 1 Synthesis of Compound 43

A compound of the formula (14) (0.800 g, 0.663 mmol), 6-maleimidohexanoic acid (0.161 g, 0.762 mmol), DMT-MM (0.263 g, 0.762 mmol), acetonitrile (8.00 g), and triethylamine (0.081 g, 0.796 mmol) were charged in a 50 mL three-necked flask equipped with a thermometer, a nitrogen inlet tube, a stirrer, a Dean-stark tube, and a cooling tube, and reacted at 25° C. for 7 hr. A pH 3.0 citrate phosphate buffer (pH 3.0) was added, and the mixture was washed with toluene. After extraction with chloroform, the organic layer was washed with 10% brine. The organic layer was dried over anhydrous magnesium sulfate and filtered. The solvent was evaporated under reduced pressure to give a compound of the formula (43).

$^1$H-NMR ($CDCl_3$, internal standard TMS); δ(ppm): 1.31 (2H, m, $-CH_2CH_2CH_2-CONH-$), 1.62 (4H, m, $-CH_2CH_2CH_2CH_2-CONH-$), 2.18 (2H, t, $-CH_2-CONH-$), 3.38 (6H, s, $-O-CH_3$), 3.40-3.85 (104H, m, $>C(CH_2O)_2-$, $-O-(CH_2CH_2O)_{12}-$, $>CNH-CH_2-OH$, $-CH_2$-maleimide), 4.62 (1H, t, $-OH$), 6.23 (1H, s, $-CH_2-CONH-$), 6.69 (2H, s, -maleimide)

(43)

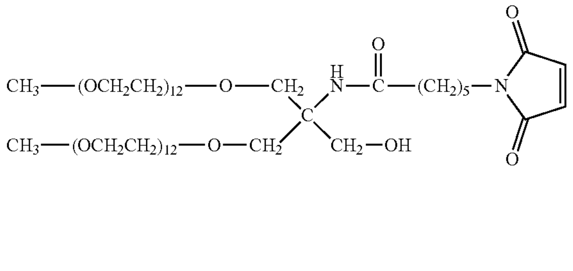

Comparative Example 2 Reaction of Compound 43 and Glutathione

A compound of the formula (43) (1 mg), and an aqueous 10 mM glutathione/25 mM sodium acetate/i mM disodium ethylenediaminetetraacetate dihydrate (EDTA) solution (1 ml) adjusted to pH 5 with acetic acid were charged in a 4 ml screw tube with a stirrer, and reacted at 25° C. for 3 hr under shading to give an aqueous solution containing a compound of the formula (44).

(44)

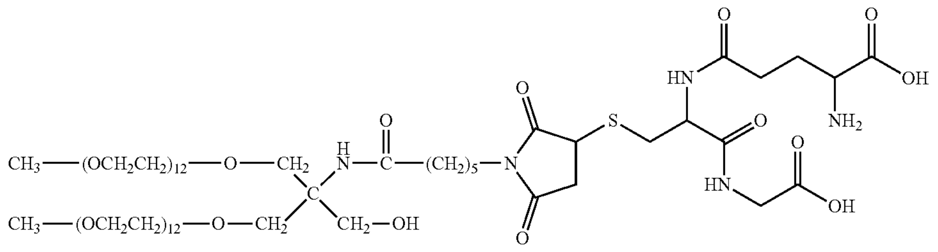

Comparative Example 3 Synthesis of Compound 45

A compound of the formula (27) (0.100 g, 0.062 mmol), N-hydroxysuccinimide (0.015 g, 0.133 mmol), dimethylaminopropylethylcarbodiimide hydrochloride (0.023 g, 0.121 mmol), and chloroform (0.574 g) were added to a 4 ml screw tube with a stirrer, and reacted at 25° C. for 4 hr. Thereafter, purification similar to that in Example 9 was performed to give a compound of the formula (45).

$^1$H-NMR ($CDCl_3$, internal standard TMS); δ(ppm): 2.28-2.43 (2H, m, —OC(O)—NH—$CH_2$—$CH_2$—COO—), 2.75-2.92 (6H, m, >$CCH_2$—NHCO—$CH_2$—$CH_2$—, —N-succinimidyl), 3.38 (6H, s, —O—$CH_3$), 3.35-3.90 (104H, m, >C($CH_2$O)$_2$—, —O—($CH_2CH_2O$)$_{12}$—, >$CCH_2$—NHCO—$CH_2$—$CH_2$—NHCO—, —OC(O)—NH—$CH_2$—$CH_2$—COO—), 4.19-4.23 (1H, m, —NH—C(O)O—$CH_2$—Fmoc (CH)), 4.35-4.50 (4H, m, >CNH—$CH_2$—OC(O)—NH—, —NH—C(O)O—$CH_2$-Fmoc), 5.62 (1H, brs, >CNH—$CH_2$—OC(O)—NH—), 5.88 (1H, brs, —NH—C(O)O—$CH_2$-Fmoc), 6.29 (1H, brs, >$CCH_2$—NHCO—$CH_2$—), 7.26-7.78 (8H, m, arom.H)

(45)

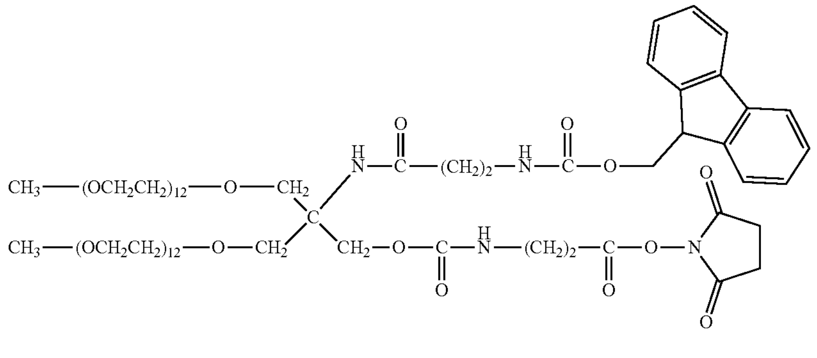

Comparative Example 4 Conjugate of Compound 45 and Doxorubicin

Doxorubicin hydrochloride (3.05 mg, 4.36 μmol), N,N-diisopropylamine (1.82 mg, 13.4 μmol), N,N-dimethylformamide, and a compound of the formula (45) (10.0 mg, 5.84 μmol) were charged in a 4 ml screw tube with a stirrer, and reacted at 25° C. for 4 hr. Thereafter, purification similar to that in Example 29 to give a drug-linker compound of the formula (46).

(46)

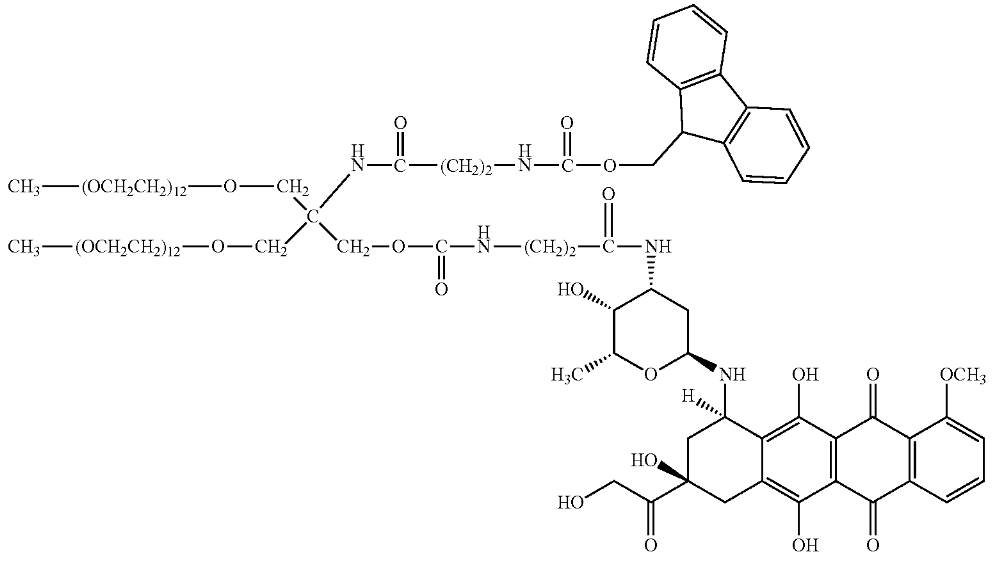

Example 37 Degradability Test of Compounds 20 and 44 Using Cathepsin B

Figure 2:
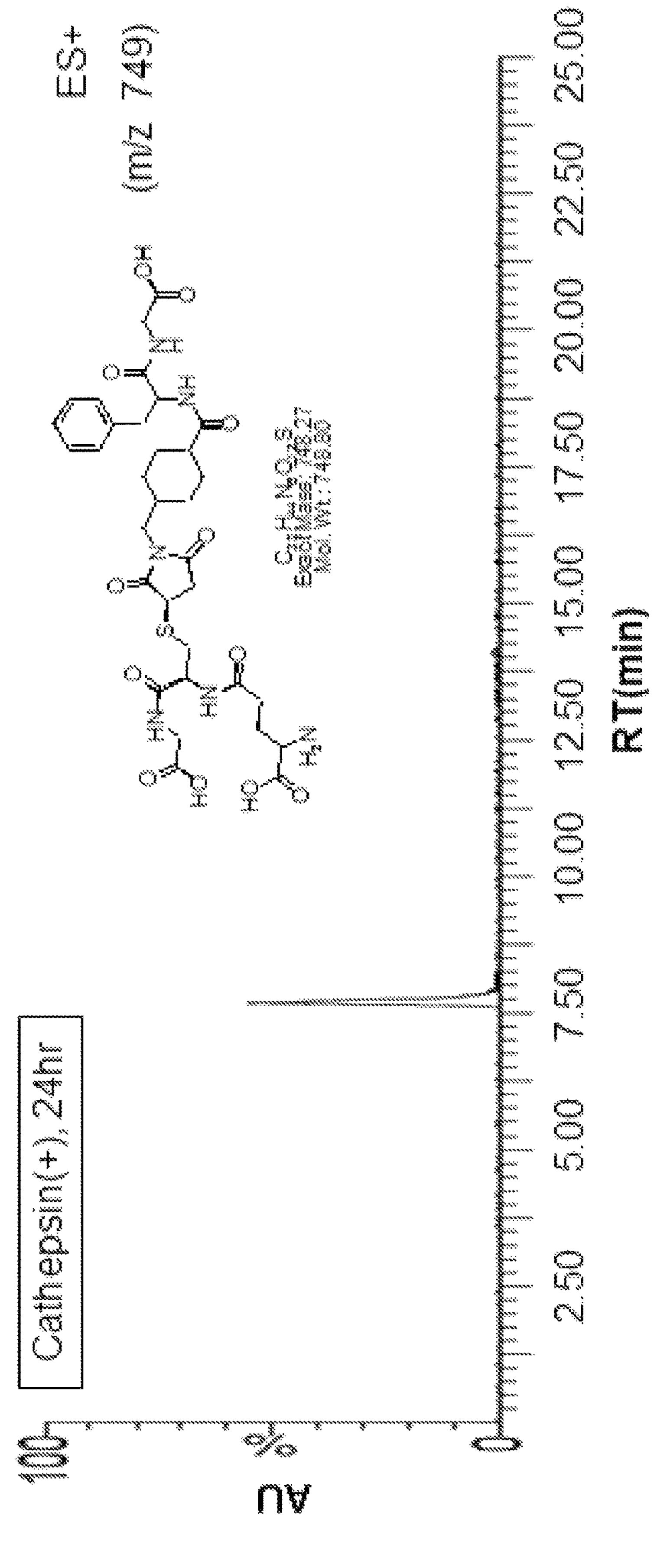
FIG. 2 shows a mass chromatogram of a degradation product derived from the compound of formula (20) after the degradability test in Example 37.
Figure 3:
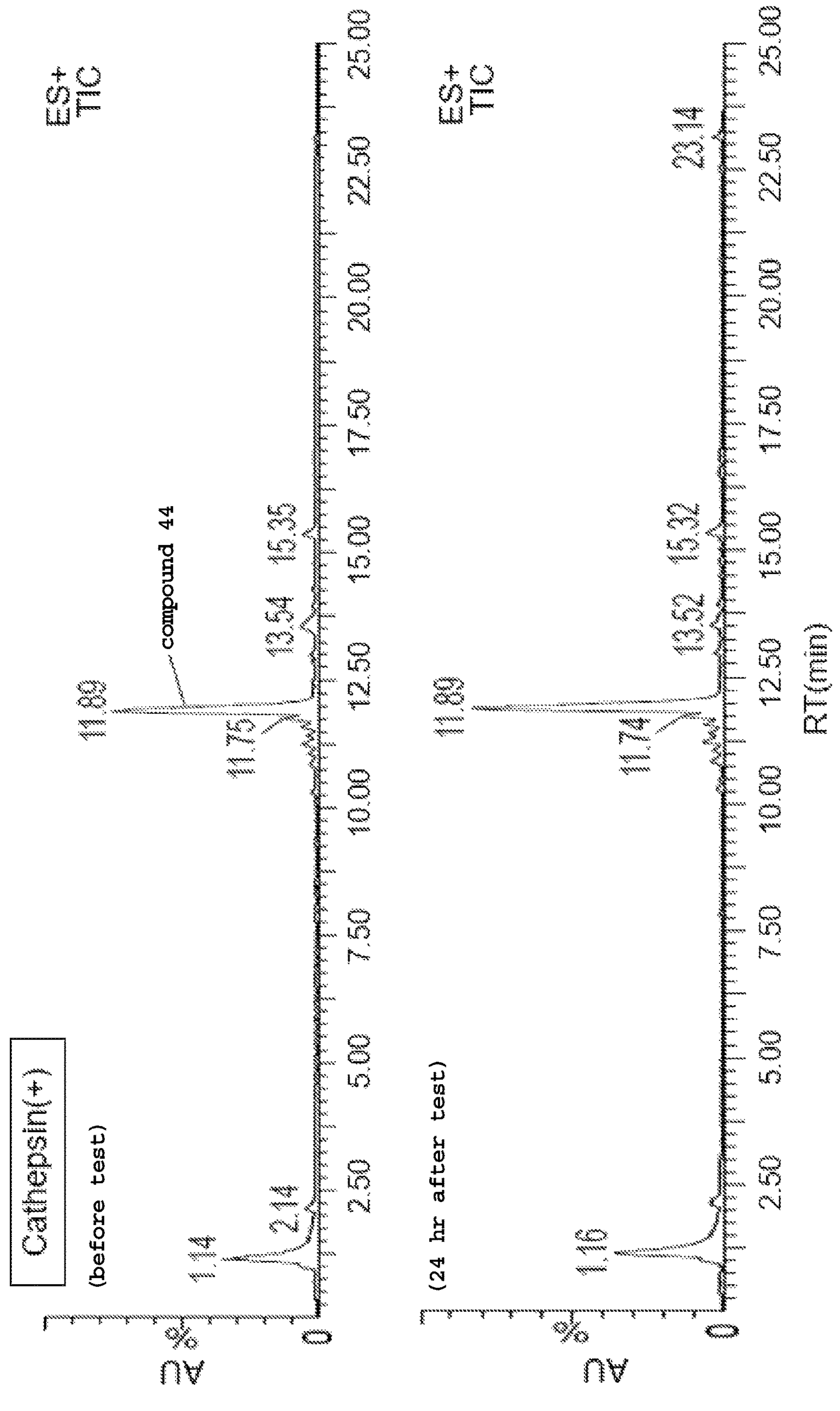
FIG. 3 shows the HPLC measurement results of the compound of the formula (44) of Comparative Example 2, before and after the degradability test in Example 37.

The compound of the formula (20) obtained in Example 10 and the compound of the formula (44) obtained in Comparative Example 2 were subjected to a peptide degradability test using cathepsin B, which is a protease in lysosomes. Human liver-derived cathepsin B buffer (25 μg, ≥1500 units/mg protein, manufactured by Sigma-Aldrich) and an aqueous 25 mM sodium acetate/1 mM EDTA solution (0.500 ml) adjusted to pH 5 with acetic acid were charged in a 4 ml screw tube to obtain a cathepsin B dilute solution. Furthermore, the cathepsin B dilute solution (0.160 ml), and an aqueous 30 mM DTT/25 mM sodium acetate/15 mM EDTA solution (0.320 ml) adjusted to pH 5 were charged in a 4 ml screw tube, stood at 25° C. for 15 min, and mixed with an aqueous 25 mM sodium acetate/1 mM EDTA solution (pH 5, 1.32 ml) heated in advance to 37° C., and an aqueous solution (0.200 ml) containing 0.1 mg/ml of the compound of the formula (20) or the formula (44). Simultaneously, an aqueous 25 mM sodium acetate/1 mM EDTA solution (pH 5, 1.80 ml) heated to 37° C., and an aqueous solution (0.200 ml) containing 0.1 mg/ml of the compound of the formula (20) or the formula (44) were mixed, and a control aqueous solution not containing cathepsin B and DTT was prepared. The prepared aqueous solution (containing/not containing cathepsin B) was incubated at 37° C., sampled, and HPLC measurement was performed under the following measurement conditions. The charts of the measurement results are shown in FIGS. 1-3.

As a result, the compound of the formula (20) of the present invention was detected at the retention time of 12.9 min in the chart of FIG. 1, but new peaks were detected at the retention times of 10.9 min and 7.7 min after the test with cathepsin B. From the results of the mass chromatogram of FIG. 2, the molecular weight of the new peak was consistent with that of the fragment degraded at the C-terminal of glycine in the compound of the formula (20). On the other hand, the compound of the formula (44), which is a comparative example, was detected at the retention time of 11.9 min in the chart of FIG. 3, and no new peak was detected even after the test with cathepsin B. Since only the compound of formula (20) having a peptide linker was specifically cleaved by cathepsin B, it was found that the peptide linker moiety was cleaved in an intracellular enzyme-dependent manner in the heterobifunctional monodisperse polyethylene glycol of the present invention.

HPLC apparatus: Alliance (Waters)
column: Sun Shell C18 (3.0×150 mm, 2.6 μm; ChromaNik Technologies Inc.)
flow rate: 0.6 mL/min
analysis time: 30 min
column temperature: 40° C.
injection volume: 5 μL
detector: mass spectrometer (ionization: ESI)
mobile phase A: 0.1 M formic acid/water
mobile phase B: 0.1 M formic acid/acetonitrile
gradient program: 10%-50% (0 min-20 min), 50%-95% (20 min-25 min), 95%-10% (25 min-30 min)

Example 38 Degradability Test of Compounds 21 and 26 Using Cathepsin B

Figure 5:
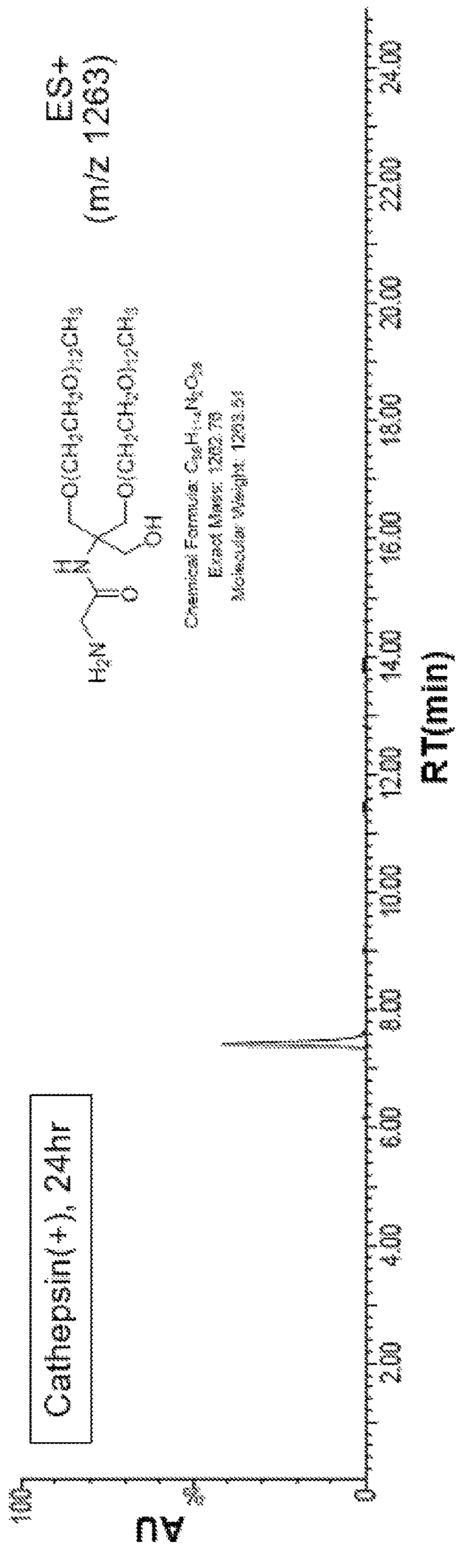
FIG. 5 shows a mass chromatogram of a degradation product derived from the compound of formula (21) after the degradability test in Example 38.
Figure 6:
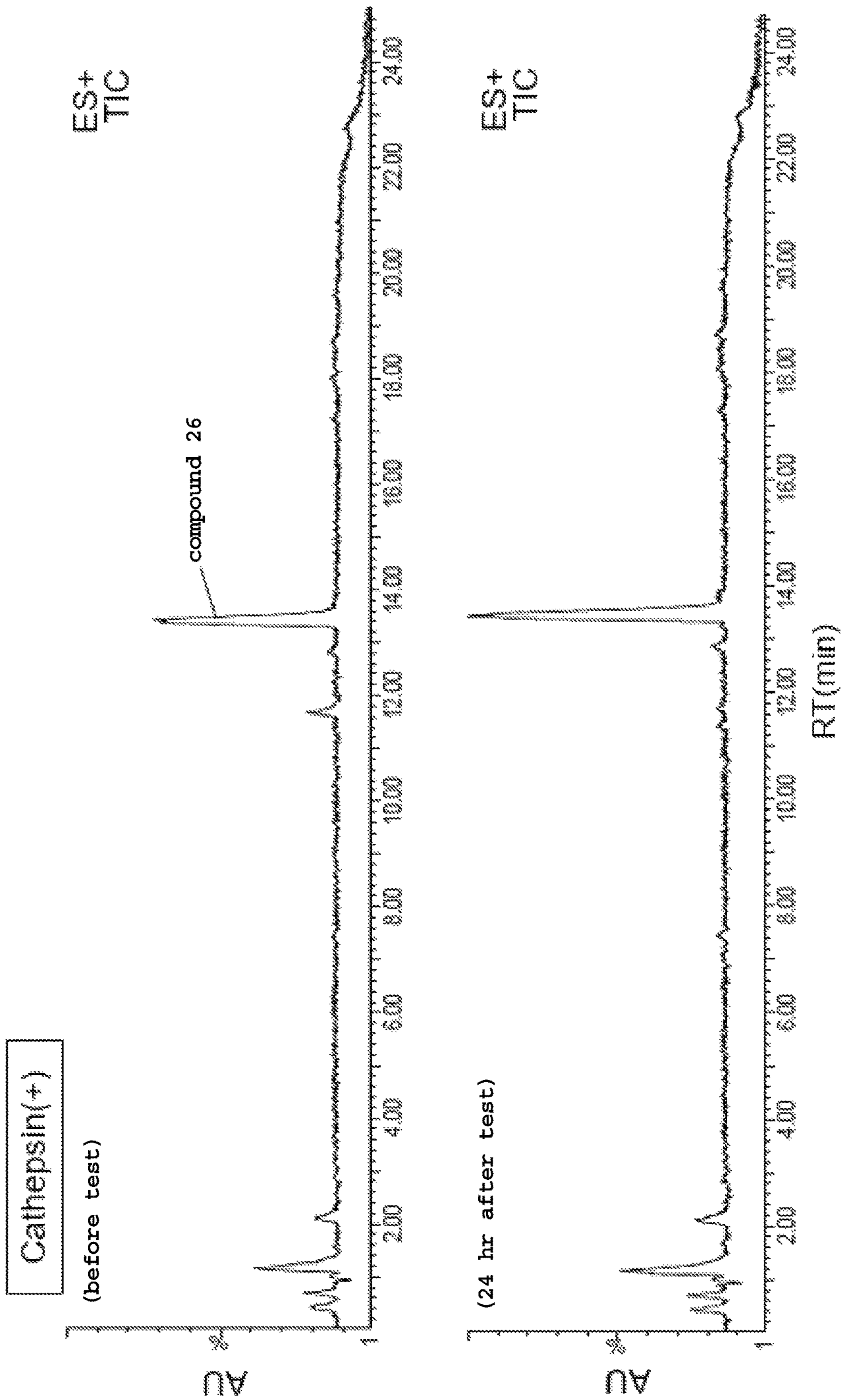
FIG. 6 shows the HPLC measurement results of the compound of the formula (26) of Example 16, before and after the degradability test in Example 38.

The compound of the formula (21) obtained in Example 11 and the compound of the formula (26) obtained in Example 16 were subjected to a peptide degradability test using cathepsin B, which is a protease in lysosomes. Thereafter, degradability test and HPLC measurement were performed under the same conditions as in Example 37. The charts of the measurement results are shown in FIGS. 4-6.

Figure 4:
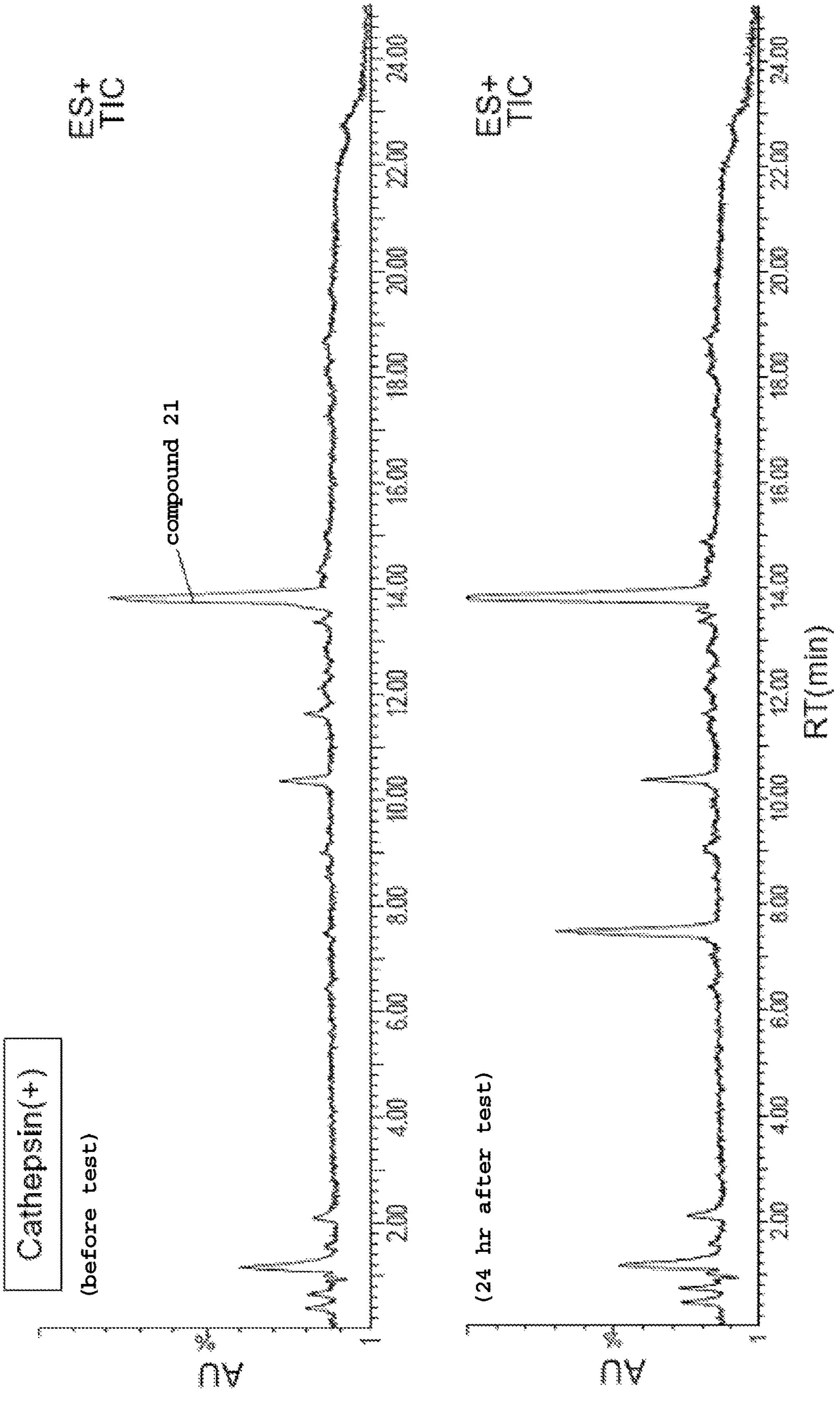
FIG. 4 shows the HPLC measurement results of the compound of the formula (21) of Example 11, before and after the degradability test in Example 38.

As a result, the compound of the formula (21) of the present invention was detected at the retention time of 13.8 min in the chart of FIG. 4, but new peaks were detected at the retention times of 13.6 min and 7.5 min after the test with cathepsin B. From the results of the mass chromatogram of FIG. 5, the molecular weight of the new peak was consistent with that of the fragment degraded at the C-terminal of glycine in the compound of the formula (21). On the other hand, the compound of the formula (26) was detected at the retention time of 13.5 min in the chart of FIG. 6, and no new peak was detected even after the test with cathepsin B. Since only the compound of formula (21) having a peptide linker was specifically cleaved by cathepsin B, it was found that the peptide linker moiety was cleaved in an intracellular enzyme-dependent manner in the heterobifunctional monodisperse polyethylene glycol of the present invention.

Figure 8:
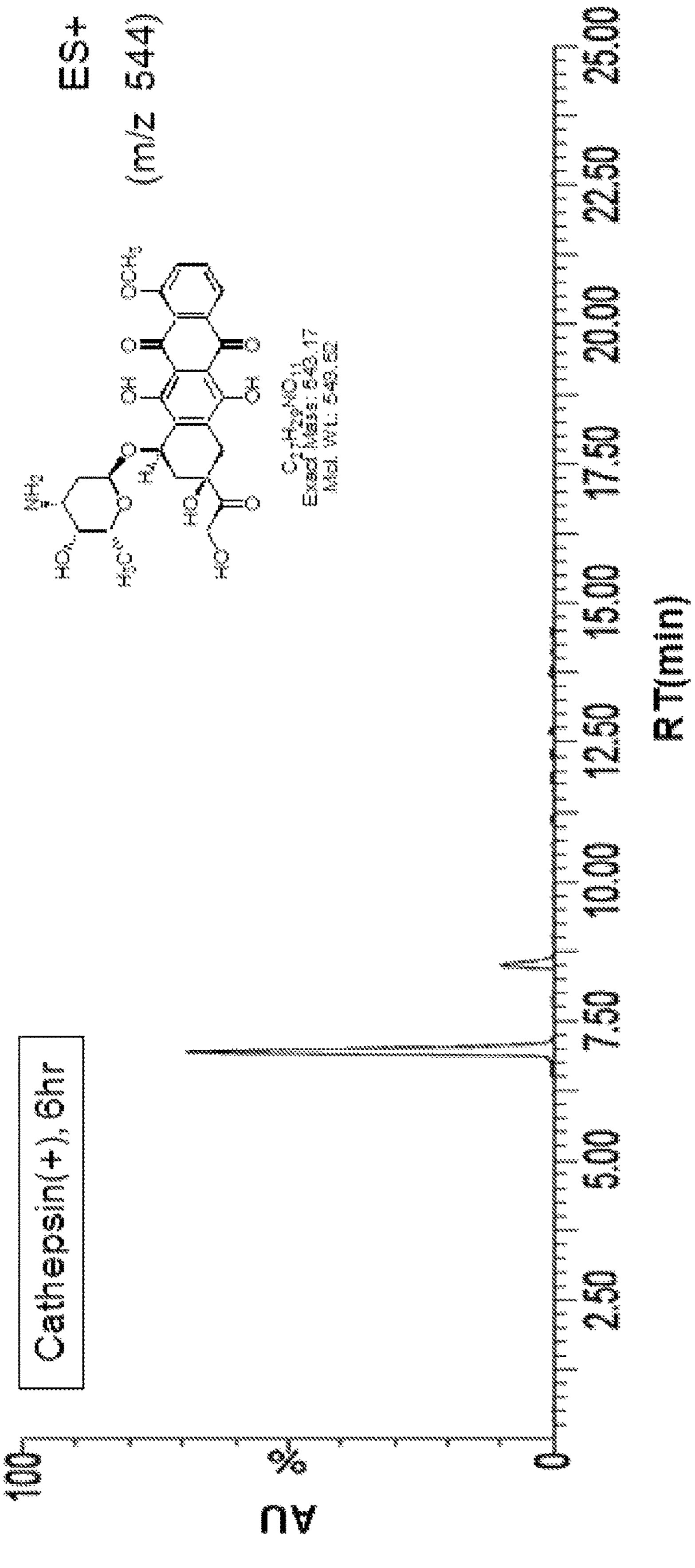
FIG. 8 shows a mass chromatogram of a degradation product derived from the compound of formula (40) after the degradability test in Example 39.
Figure 9:
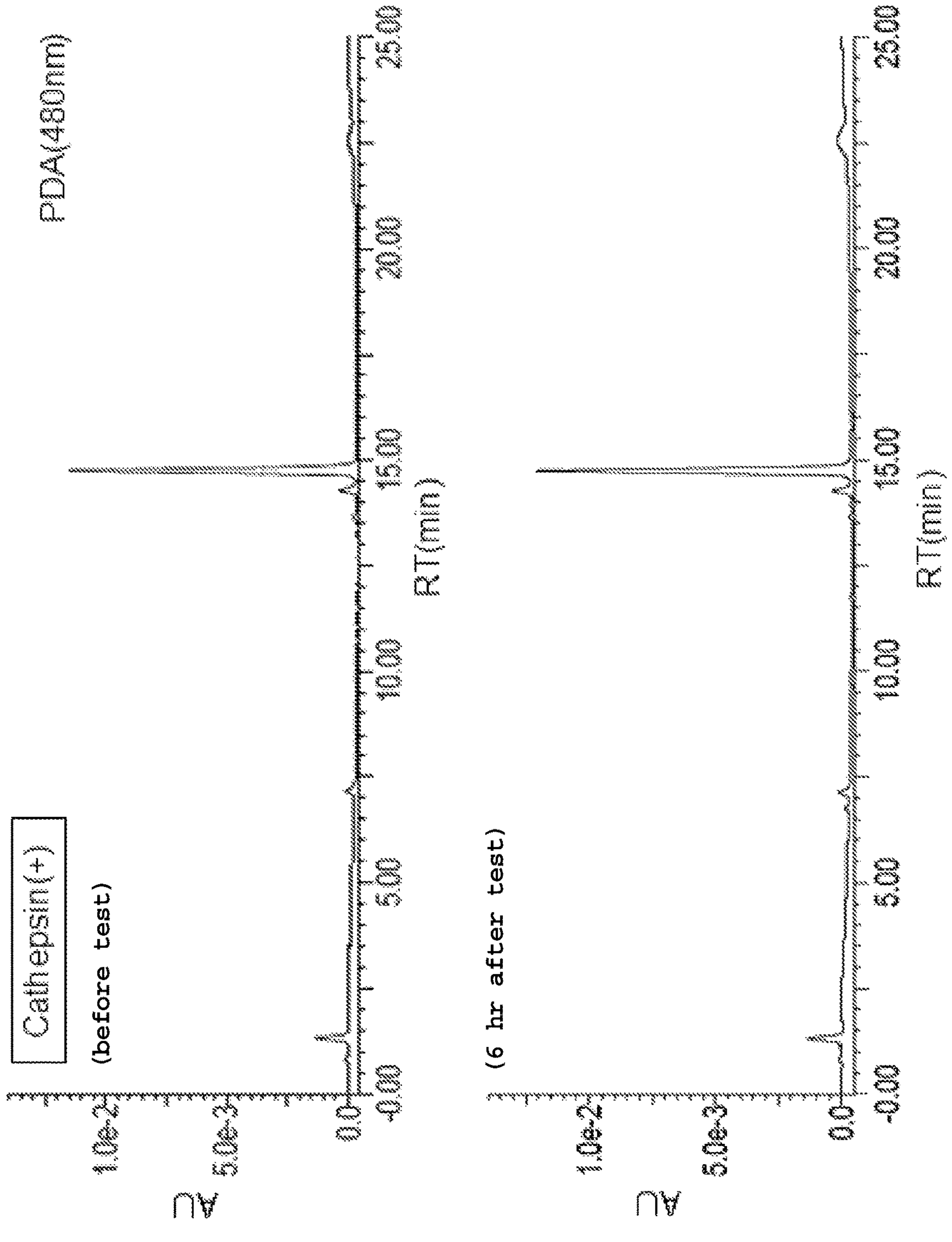
FIG. 9 shows the HPLC measurement results of the compound of the formula (46) of Comparative Example 4, before and after the degradability test in Example 39.

Example 39 Degradability Test of Drug-Linker Compounds 40 and 46 Using Cathepsin B The drug-linker compound of the formula (40) obtained in Example 30 and the drug-linker compound of the formula (46) obtained in Comparative Example 4 were subjected to a peptide degradability test using cathepsin B, which is a protease in lysosomes. Thereafter, the test was performed in the same manner as in Example 37 and HPLC measurement was performed under the following measurement conditions. The charts of the measurement results are shown in FIGS. 7-9.

Figure 7:
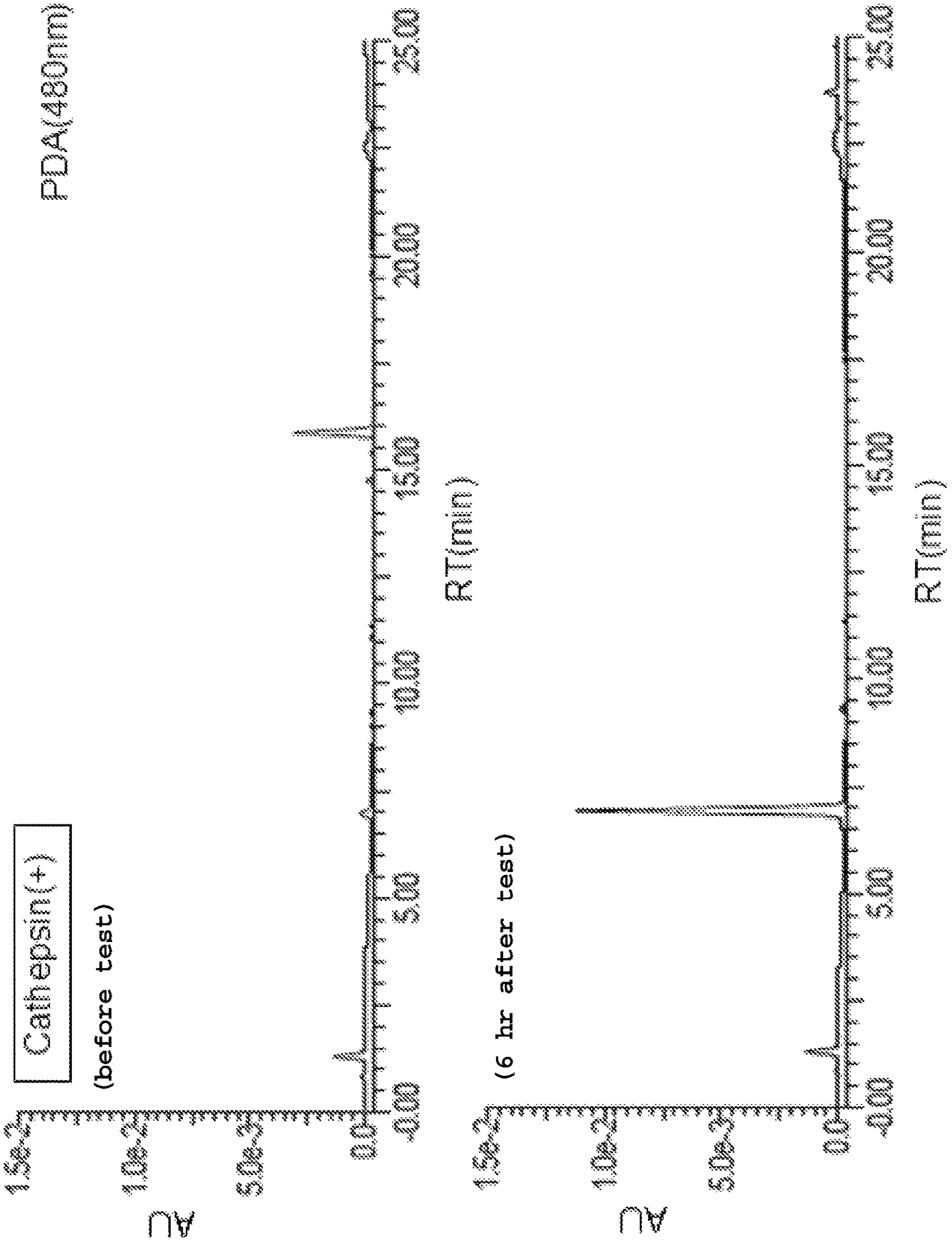
FIG. 7 shows the HPLC measurement results of the compound of the formula (40) of Example 30, before and after the degradability test in Example 39.

As a result, the drug-linker compound of the formula (40) of the present invention was detected at the retention time of 16.8 min in the chart of FIG. 7, but a new peak was detected at the retention time of 6.8 min after the test with cathepsin B. From the results of the mass chromatogram of FIG. 8, the new peak was consistent with that of doxorubicin. On the other hand, the drug-linker compound of the formula (46), which is a comparative example, was detected at the retention time of 14.7 min in the chart of FIG. 9, and no new peak was detected even after the test with cathepsin B. It was found that, when the heterobifunctional monodisperse polyethylene glycol of the present invention has a para-aminobenzyl alcohol group at the C-terminal of the peptide, it can release a drug in a chemically unmodified structure since the para-aminobenzyl alcohol group is also eliminated by the cleavage of a peptide linker.

HPLC apparatus: Alliance (Waters)
column: Sun Shell C18 (3.0×150 mm, 2.6 μm; ChromaNik Technologies Inc.)
flow rate: 0.6 mL/min
analysis time: 30 min
column temperature: 40° C.
injection volume: 5 μL
detector: mass spectrometer (ionization: ESI), photodiode array (PDA) (wavelength: 480 nm)
mobile phase A: 0.1 M formic acid/water
mobile phase B: 0.1 M formic acid/acetonitrile
gradient program: 10%-80% (0 min-20 min), 80%-95% (20 min-25 min), 95%-10% (25 min-30 min)

Figure 10:
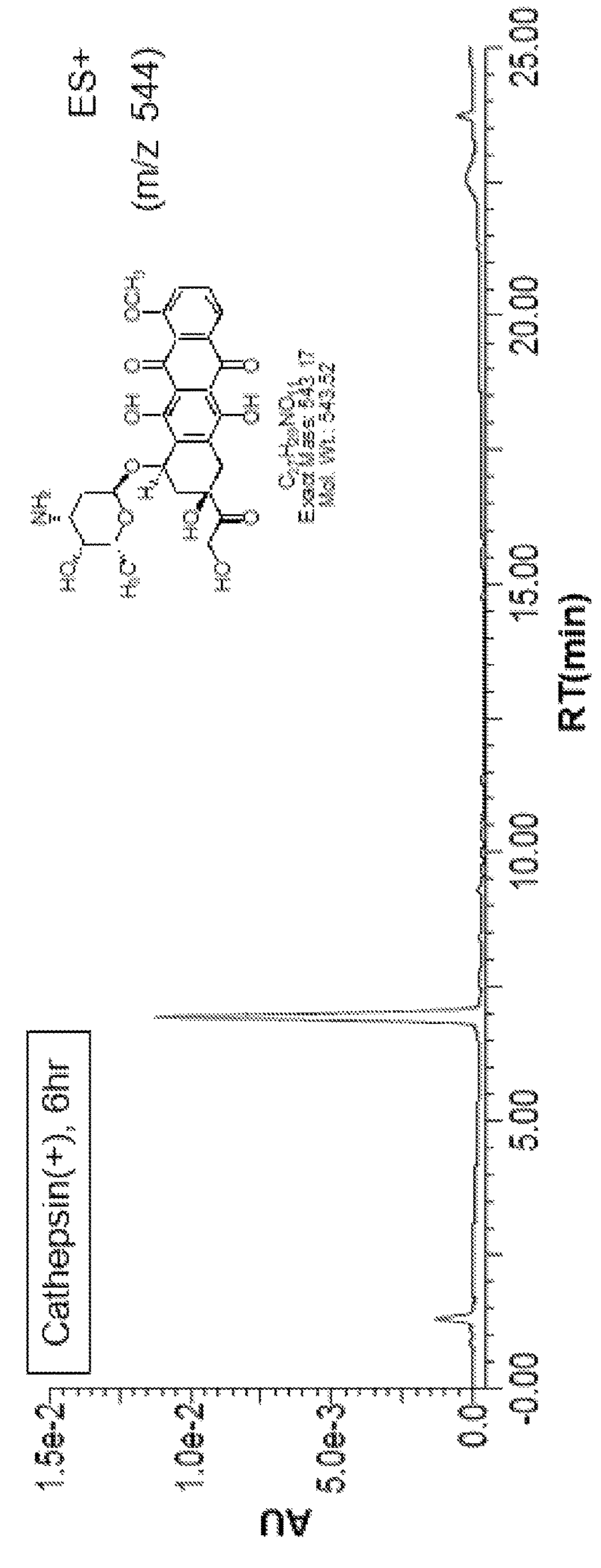
FIG. 10 shows a mass chromatogram of a degradation product derived from the compound of formula (42) after the degradability test in Example 40.

Example 40 Degradability Test of Drug-Linker Compounds 42 and 46 Using Cathepsin B The drug-linker compound of the formula (42) obtained in Example 32 and the drug-linker compound of the formula (46) obtained in Comparative Example 4 were subjected to a peptide degradability test using cathepsin B, which is a protease in lysosomes. Thereafter, degradability test and HPLC measurement were performed under the same conditions as in Example 39. The charts of the measurement results are shown in FIG. 10.

As a result, in the drug-linker compound of the formula (42) of the present invention, a new peak was detected at the retention time of 6.8 min after the test with cathepsin B as in Example 39. From the results of the mass chromatogram, the new peak was consistent with that of doxorubicin. On the other hand, in the drug-linker compound of the formula (46), which is a comparative example, no new peak was detected even after the test with cathepsin B. It was found that, when the heterobifunctional monodisperse polyethylene glycol of the present invention has a para-aminobenzyl alcohol group at the C-terminal of the peptide, it can release a drug in a chemically unmodified structure since the para-aminobenzyl alcohol group is also eliminated by the cleavage of a peptide linker.

Example 41 Cytotoxicity Test Using Drug-Linker Compounds 40 and 46

Figure 11:
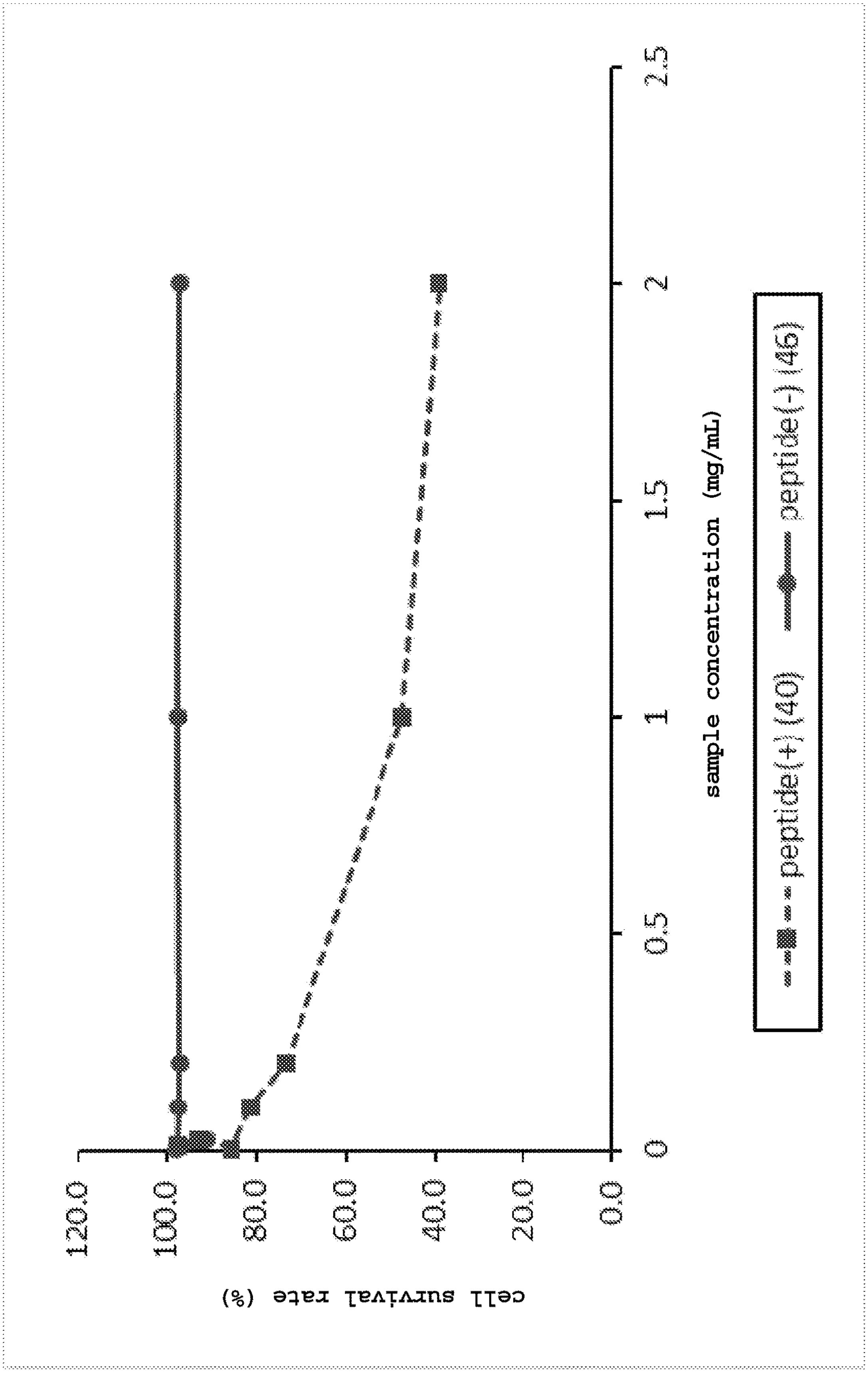
FIG. 11 shows a graph plotting cell viability per each sample concentration in the cytotoxicity test of Example 41 using the drug-linker compounds of the formula (40) and the formula (46).

Using 10 mL of medium RPMI-1640 (10% FBS Pn/St) and 80% confluent cells of HeLa cells, a cell suspension was prepared to 5000 cells/well, and the cell suspension was dispensed to each plate of a 96-well microplate. After culturing in a carbon dioxide gas incubator for 24 hr, the medium was exchanged, and a medium in which the drug-linker compound of the formula (40) obtained in Example 30 or the compound of the formula (46) obtained in Comparative Example 4 was dissolved at various concentrations was added and the cells were cultured at 37° C. for 24 hr. Cell Counting Kit-8 solution (manufactured by DOJINDO LABORATORIES) was added to each well of the microplate, and a color reaction was performed in a carbon dioxide gas incubator for 2 hr. The absorbance at 450 nm was measured with a microplate reader, the cell survival rate was calculated by the following formula, and the cytotoxicity of the drug was evaluated. The cell survival rate at each concentration is shown in FIG. 11.

$$\text{cell survival rate (\%)}=[(A_{sample}-A_{blank})/(A_{cell}-A_{blank})]\times 100$$

$A_{sample}$: absorbance of sample,
$A_{cell}$: absorbance of cells only without sample,
$A_{blank}$: absorbance of cell-free blank As a result, the drug-linker compound of the formula (40) of the present invention showed cytotoxicity because the cell survival rate decreased in a sample concentration-dependent manner. On the other hand, the compound of the formula (46), which is a comparative example, showed a high cell survival rate even under the condition of a high sample concentration and did not show cytotoxicity. Therefore, it was found that the drug-linker compound using the heterobifunctional monodisperse polyethylene glycol of the present invention has higher cytotoxicity as compared with the drug-linker compound of the comparative example without containing a peptide linker, and the drug can be released in cells.

Example 42 Cytotoxicity Test Using Drug-Linker Compounds 42 and 46

Figure 12:
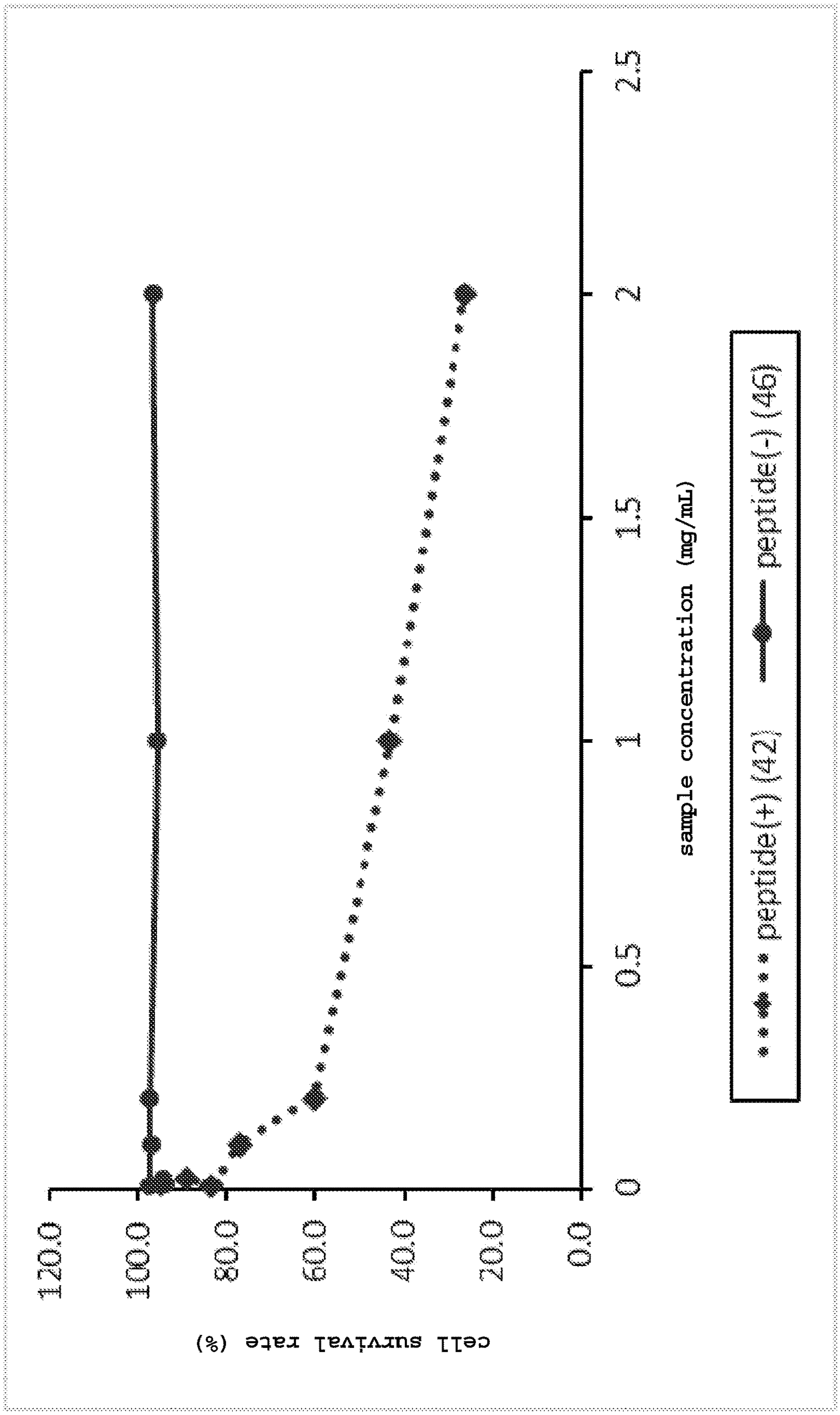
FIG. 12 shows a graph plotting cell viability per each sample concentration in the cytotoxicity test of Example 42 using the drug-linker compounds of the formula (42) and the formula (46).

Using 10 mL of medium RPMI-1640 (10% FBS Pn/St) and 80% confluent cells of HeLa cells, a cell suspension was prepared to 5000 cells/well, and the cell suspension was dispensed to each plate of a 96-well microplate. After culturing in a carbon dioxide gas incubator for 24 hr, the medium was exchanged, and a medium in which the drug-linker compound of the formula (42) obtained in Example 32 or the compound of the formula (46) obtained in Comparative Example 4 was dissolved at various concentrations was added and the cells were cultured at 37° C. for 24 hr. Cell Counting Kit-8 solution (manufactured by DOJINDO LABORATORIES) was added to each well of the microplate, and a color reaction was performed in a carbon dioxide gas incubator for 2 hr. The absorbance at 450 nm was measured with a microplate reader, the cell survival rate was calculated by the following formula, and the cytotoxicity of the drug was evaluated. The cell survival rate at each concentration is shown in FIG. 12.

$$\text{cell survival rate (\%)}=[(A_{sample}-A_{blank})/(A_{cell}-A_{blank})]\times 100$$

$A_{sample}$: absorbance of sample, $A_{cell}$: absorbance of cells only without sample, $A_{blank}$: absorbance of cell-free blank As a result, the tendency of the cell survival rate was the same as in Example 41, and it was found that the drug-linker compound using the heterobifunctional monodisperse polyethylene glycol of the present invention has higher cytotoxicity as compared with the drug-linker compound of the comparative example without containing a peptide linker, and the drug can be released in cells.

Example 43 Evaluation of Hydrophilicity of Various Linkers

The compounds of formulas (15), (21), (28) and (34) obtained in Examples 5, 11, 18 and 24 were subjected to HPLC measurement under the following measurement conditions, and the retention times of the peaks of various linkers are shown in the following Table.

As a result, the retention time of the linker containing valine-citrulline was the shortest, and the retention time was shorter in the order of the linker containing valine-alanine and the linker containing phenylalanine-glycine. Therefore, it was found that, among the heterobifunctional monodisperse polyethylene glycols of the present invention, the linker containing valine-citrulline can further enhance the hydrophilicity.

HPLC device: Thermo Fisher Ultimate3000 column: Sun Shell C18 (3.0×150 mm, 2.6 μm; ChromaNik Technologies Inc.)

flow rate: 0.6 mL/min analysis time: 80 min column temperature: 40° C.

injection volume: 10 μL detector: corona charged aerosol detector (CAD)

mobile phase A: 0.1 M formic acid/water mobile phase B: 0.1 M formic acid/acetonitrile gradient program: 20%-95% (0 min-75 min), 95%-95% (75 min-80 min)

TABLE 1

| compound No. (peptide) | retention time (min) |
|---|---|
| compound 15 (phenylalanine-glycine) | 29.8 |
| compound 21 (valine-alanine-glycine) | 26.4 |
| compound 28 (phenylalanine-glycine) | 27.3 |
| compound 34 (valine-citrulline) | 23.4 |

The heterobifunctional monodisperse polyethylene glycol of the present invention was released from the drug by being cleaved by an enzyme in the cell, and suppressed a decrease in the pharmacological activity due to the presence in a linker-bound state.

INDUSTRIAL APPLICABILITY

The heterobifunctional monodisperse polyethylene glycol of the present invention has two adjacent monodisperse polyethylene glycol side chains that permit release of a drug in a sustained manner by degradation of peptide linker by intracellular enzymes and effectively masks the hydrophobicity of the drug. Therefore, it is useful for modifying biofunctional molecules such as physiologically active proteins, peptides, antibodies, nucleic acids and small molecule drugs, drug carriers in drug delivery systems, or diagnostic materials and medical devices.

This application is based on patent application No. 2019-176066 filed in Japan, the contents of which are encompassed in full herein.

The invention claimed is:

1. A heterobifunctional monodisperse polyethylene glycol represented by the formula (1):

(1)

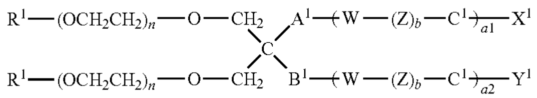

wherein $X^1$ and $Y^1$ are each an atomic group containing at least a functional group that reacts with a functional group present in a biofunctional molecule to form a covalent bond, and the aforementioned functional group contained in the atomic group $X^1$ and the aforementioned functional group contained in the atomic group $Y^1$ are different from each other;

$R^1$ is a hydrocarbon group having 1-7 carbon atoms or a hydrogen atom;

n is an integer of 3-72;

$A^1$ is $-L^1-(CH_2)_{m1}-L^2-$, $-L^1-(CH_2)_{m1}-L^2-(CH_2)_{m2}-$, an amide bond, a urethane bond, a secondary amino group, or a single bond, and m1 and m2 are each independently an integer of 1-5;

$B^1$ is $-CH_2-L^3-$, $-CH_2-L^3-(CH_2)_{m3}-L^4-$ or $-CH_2-L^3-(CH_2)_{m3}-L^4-(CH_2)_{m4}-$, and m3 and m4 are each independently an integer of 1-5;

W is an oligopeptide with 2 to 4 residues;

Z is a spacer with a bifunctional para-aminobenzyl alcohol group that binds to the C-terminal of peptide;

when a1=1, a2=0, and when a1=0, a2=1;

b is 0 or 1;

$C^1$ is $-L^5-(CH_2)_{m5}-$, $-L^5-(CH_2)_{m5}-L^6-(CH_2)_{m6}-$, an amide bond, or a single bond, and m5 and m6 are each independently an integer of 1-5; and $L^1$-$L^6$ are each independently an ether bond, a urethane bond, an amide bond, a secondary amino group, a carbonyl group, or a single bond.

2. The heterobifunctional monodisperse polyethylene glycol according to claim 1, wherein W is an oligopeptide with 2 to 4 residues and containing at least one of hydrophobic neutral amino acids of phenylalanine, leucine, valine, and isoleucine, and the other amino acids consist of neutral amino acids other than cysteine.

3. The heterobifunctional monodisperse polyethylene glycol according to claim 1, wherein W is an oligopeptide with 2 to 4 residues and containing at least one of hydrophobic neutral amino acids of phenylalanine, leucine, valine, and isoleucine, and the other amino acids contain at least one of alanine, glycine, citrulline, proline, serine, and asparagine.

4. The heterobifunctional monodisperse polyethylene glycol according to claim 1, wherein W is an oligopeptide whose C-terminal amino acid is glycine.

5. The heterobifunctional monodisperse polyethylene glycol according to claim 1, wherein W is dipeptide.

6. The heterobifunctional monodisperse polyethylene glycol according to claim 1, wherein $X^1$ and $Y^1$ in the formula (1) are each independently selected from the group consisting of the formula (a), the formula (b1), the formula (b2), the formula (c), the formula (d1), the formula (d2), the formula (e), the formula (f), the formula (g), the formula (h), the formula (i), the formula (j), the formula (k), the formula (l), the formula (m), the formula (n), and the formula (o):

(a)

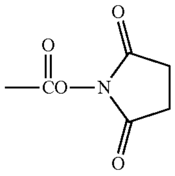

(b1)

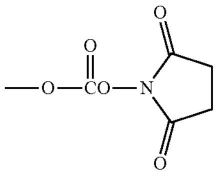

(b2)

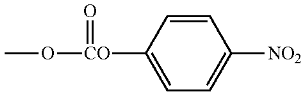

(c)

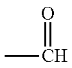

(d1)

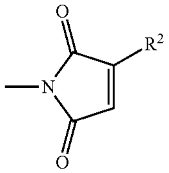

(d2)

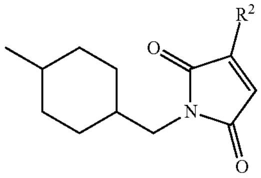

-continued (e)

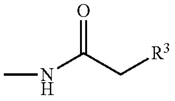

(f)

—COOH (g)

—SH (h)

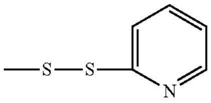

(i)

$—NH_2$ (j)

$—O—NH_2$ (k)

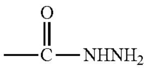

(l)

$—C{\equiv}C—R^4$ (m)

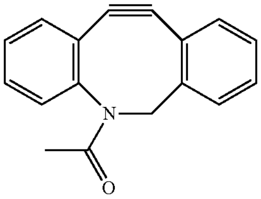

(n)

$—N_3$ (o)

—OH wherein $R^2$ is a hydrogen atom or a hydrocarbon group having 1-5 carbon atoms; $R^3$ is a halogen atom selected from a chlorine atom, a bromine atom, and an iodine atom; and $R^4$ is a hydrogen atom or a hydrocarbon group having 1-5 carbon atoms.

* * * * *